(12) United States Patent
Ishikawa et al.

(10) Patent No.: US 9,505,732 B2
(45) Date of Patent: Nov. 29, 2016

(54) AUTO MAGNETIC METAL SALEN COMPLEX COMPOUND

(75) Inventors: Yoshihiro Ishikawa, Tokyo (JP); Haruki Eguchi, Kawasaki (JP)

(73) Assignees: IHI CORPORATION, Tokyo (JP); Yoshihiro Ishikawa, Tokyo (JP)

( * ) Notice: Subject to any disclaimer, the term of this patent is extended or adjusted under 35 U.S.C. 154(b) by 1292 days.

(21) Appl. No.: 13/112,409

(22) Filed: May 20, 2011

(65) Prior Publication Data

US 2012/0029167 A1 Feb. 2, 2012

Related U.S. Application Data

(63) Continuation of application No. PCT/IB2009/007525, filed on Nov. 20, 2009.

(30) Foreign Application Priority Data

| Nov. 20, 2008 | (JP) | 2008-297065 |
| Nov. 25, 2008 | (JP) | 2008-299482 |
| Jul. 29, 2009 | (JP) | 2009-177112 |

(51) Int. Cl.

| C07F 5/00 | (2006.01) |
| C07D 305/14 | (2006.01) |
| A61K 31/135 | (2006.01) |
| A61K 31/167 | (2006.01) |
| A61K 31/295 | (2006.01) |
| A61K 31/337 | (2006.01) |
| C07C 251/24 | (2006.01) |

(52) U.S. Cl.
CPC ............ C07D 305/14 (2013.01); A61K 31/135 (2013.01); A61K 31/167 (2013.01); A61K 31/295 (2013.01); A61K 31/337 (2013.01); C07C 251/24 (2013.01)

(58) Field of Classification Search
CPC .. A61K 31/00; A61K 31/135; A61K 31/167; A61K 31/295; A61K 31/337; A61K 31/35; C07C 251/24; C07C 305/14; C07D 305/14; C07K 251/24
USPC ....... 424/1.11, 1.65, 9.1; 530/323, 328, 395; 536/6.4, 16.8, 17.1, 26.7, 26.8, 28.5, 536/28.55, 121; 540/145; 544/64, 181, 225; 546/6; 548/106, 402; 549/210; 552/504, 13, 32; 562/440; 564/273
See application file for complete search history.

(56) References Cited

U.S. PATENT DOCUMENTS

| 4,727,068 A | 2/1988 | Abrams et al. |
| 4,828,941 A | 5/1989 | Sterzel et al. |
| 4,871,716 A | 10/1989 | Longo et al. |
| 6,172,268 B1 | 1/2001 | Tohma et al. |
| 2005/0096260 A1 | 5/2005 | Ueno et al. |
| 2009/0169484 A1 | 7/2009 | Eguchi et al. |
| 2009/0311163 A1 | 12/2009 | Eguchi et al. |

FOREIGN PATENT DOCUMENTS

| EP | 0800829 | 10/1997 |
| EP | 1097711 | 5/2001 |
| EP | 1114836 | 7/2001 |
| EP | 1007533 | 6/2005 |
| JP | 1974-13316 | 2/1974 |
| JP | 1974-13317 | 2/1974 |
| JP | 62-174014 | 7/1987 |
| JP | 62-192383 | 8/1987 |
| JP | 3-21319 | 1/1991 |
| JP | 5-45932 | 2/1993 |
| JP | 5-23276 | 4/1993 |
| JP | 5-216967 | 8/1993 |
| JP | 07-149799 | 6/1995 |
| JP | 7-296045 | 11/1995 |
| JP | 9-291145 | 11/1997 |
| JP | 9-328438 | 12/1997 |
| JP | 9-329602 | 12/1997 |
| JP | 10-310796 | 11/1998 |
| JP | 11-6825 | 1/1999 |
| JP | 2930263 | 5/1999 |

(Continued)

OTHER PUBLICATIONS

Fanning et al, Inorganic Chemistry, 1985, vol. 24, No. 19, pp. 2884-2889.*
Chinese Office Action dated Dec. 9, 2013 in corresponding Chinese Patent Application No. 200980146570.9.
Chinese Office Action dated Apr. 27, 2013 in corresponding Chinese Patent Application No. 200980146570.9.
Russian Office Action issued Jun. 27, 2012 in corresponding Russian Patent Application No. 2011124913.
Extended European Search Report dated Jun. 4, 2012 in corresponding European Patent Application No. 09827243.8.

(Continued)

Primary Examiner — D L Jones

(57) ABSTRACT

A drug using the magnetic properties of a metal salen complex as represented by the following general formula in order to magnetize the intended drug by chemically binding the drug to a metal salen complex so that the drug can be delivered to the target diseased site. The drug can be delivered to the diseased site using the magnetic properties of the drug per se without using a carrier made of a magnetic substance as in the conventional methods.

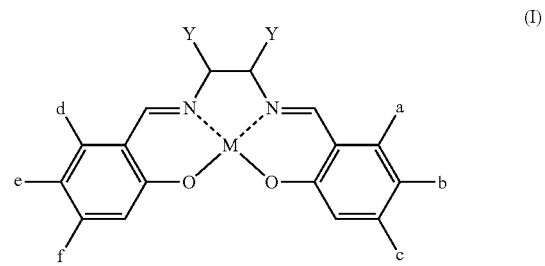

5 Claims, 16 Drawing Sheets

(56) References Cited

FOREIGN PATENT DOCUMENTS

| | | |
|---|---|---|
| JP | 11-507646 | 7/1999 |
| JP | 11-217385 | 8/1999 |
| JP | 2000-269013 | 9/2000 |
| JP | 2001-10978 | 1/2001 |
| JP | 2002-500177 | 1/2002 |
| JP | 2002-93606 | 3/2002 |
| JP | 2004-514724 | 5/2004 |
| JP | 2004-239685 | 8/2004 |
| JP | 2005-154402 | 6/2005 |
| JP | 2005-522495 | 7/2005 |
| JP | 2006-528506 | 12/2006 |
| JP | 2007-91710 | 4/2007 |
| JP | 2008-115129 | 5/2008 |
| JP | 2008-117969 | 5/2008 |
| JP | 2009-173631 | 8/2009 |
| WO | 94/13300 | 6/1994 |
| WO | 94/16683 | 8/1994 |
| WO | 96/40148 | 12/1996 |
| WO | 96/40149 | 12/1996 |
| WO | 99/34779 | 7/1999 |
| WO | 99/64004 | 12/1999 |
| WO | 02/44187 | 6/2002 |
| WO | 03/035078 | 5/2003 |
| WO | 03/086563 | 10/2003 |
| WO | 2005/011810 | 2/2005 |
| WO | 2006/133354 | 12/2006 |
| WO | 2007/026725 | 3/2007 |
| WO | 2008/001851 | 1/2008 |

OTHER PUBLICATIONS

"anti-Spin-Delocalization Effect in Co—C Bond Dissociation Enthalpies", Qi et al., Organometallics, vol. 27, No. 12, 2008, pp. 2688-2698.

Reactions of Fluorenylidene Nitrile Ylides with (Salen)metal Complexes, SriHari et al., Inorganic Chemistry, vol. 29, No. 17, 1990, pp. 3154-3157.

Electronic and Steric Effects on the Oxygenation of Organic Sulfides and Sulfoxides with Oxo(salen)chromium(V) Complexes, Venkataramanan et al., Journal of Organic Chemistry, vol. 68, No. 19, 2003, pp. 7460-7470.

International Search Report mailed Feb. 9, 2010 issued in corresponding International Patent Application No. PCT/IB2009/007525.

International Search Report mailed Sep. 11, 2007 issued in corresponding International Patent Application No. PCT/JP2007/063011.

European Search Report dated Jun. 23, 2008 issued in corresponding European Patent Application No. 06783129.7.

European Search Report dated Nov. 4, 2008 issued in corresponding European Patent Application No. 06783129.7.

European Search Report dated Jun. 9, 2010 issued in corresponding European Patent Application No. 06783129.7.

European Search Report dated Jun. 16, 2009 issued in corresponding European Patent Application No. 07767804.3.

Yong Zhang et al., "Surface modification of superparamagnetic magnetite nanoparticles and their intracellular uptake", Biomaterials, vol. 23, 2002, pp. 1553-1561.

Ajay Kumar Gupta et al., "Receptor-Mediated Targeting of Magnetic Nanoparticles using Insulin as a Surface Ligand to prevent Endocytosis", IEEE Transactions on Nanobioscience, vol. 2, No. 4, Dec. 2003, pp. 255-261.

Claude Sestier et al., "Surface modification of superparamagnetic nanoparticles (Ferrofluid) studied with particle electrophoresis: Application to the specific targeting of cells", Electrophoresis, vol. 19, 1998, pp. 1220-1226.

V.P. Torchilin et al., "Magnetic Sephadex as a carrier for enzyme immobilization and drug targeting", Journal of Biomedical Materials Research, vol. 19, 1985, pp. 461-466.

S.V. Bhat et al., "Structures and Stereochemistry of New Labdane Diterpenoids From Coleus Forskohlll Briq", Tetrahedron Letters, No. 19, 1977, pp. 1669-1672.

David P. Rotella et al., "Optimization of Substituted $N$-3-Benzylimidazoquinazolinone Sulfonamides as Potent and Selective PDE5 Inhibitors", J. Med. Chem. vol. 43, 2000, pp. 5037-5043.

David P. Rotella et al., "N-3-Substituted Imidazoquinazolines: Potent and Selective PDE5 Inhibitors as Potential Agents for Treatment of Erectile Dysfunction", J. Med. Chem. vol. 43, 2000, pp. 1257-1263.

M. Leclaire et al., "A Simple Access to a Forskolin Precursor", Tetrahedron Letters, vol. 30, No. 46, 1989, pp. 6331-6334.

Christopher Alexiou et al., "Locoregional Cancer Treatment with Magnetic Drug Targeting", Cancer Research, vol. 60, Dec. 2000, pp. 6641-6648.

Wilbur R. Leopold et al., "Carcinogenicity of Antitumor *cis*-Platinum(II) Coordination Complexes in the Mouse and Rat", Cancer Research, vol. 39, Mar. 1979, pp. 913-918.

Ikuo Takahashi et al., "Heat enhances the cytotoxicity of *cis*-diamminedichloro-platinum(II) and its analogues *cis*-1, 1-cyclobutane- dicarboxylato(2R)-2-methyl-1, 4-butanediammineplatinum(II) and *cis*-diammine(glycolato)platinum in vitro" Cancer Chemother Pharmacol, vol. 33, 1993, pp. 31-35.

Somu SriHari et al., "Reactions of Fluorenylidene Nitrile Ylides with (Salen)metal Complexes" Inorg. Chem. vol. 29, 1990, pp. 3154-3157.

Jens Kortus et al., "Electronic structure, magnetic ordering, and phonons in molecules and solids", Dec. 2003, pp. 1-146.

P.K. Gupta et al., "Magnetically Controlled Targeted Micro-Carrier Systems", Magnetically Controlled Drug Deliver, vol. 44, No. 3, 1989, pp. 175-186.

Urs O. Häfeli et al., "Effective Targeting of Magnetic Radioactive Y-microspheres to Tumor Cells by an Externally Applied Magnetic Field. Preliminary In Vitro and In Vivo Results", Nucl. Med. Biol., vol. 22, No. 2, 1995, pp. 147-155.

Jean-Paul Fortin-Ripoche et al., "Magnetic Targeting of Magnetoliposomes to Solid Tumors with MR Imaging Monitoring in Mice: Feasibility", Radiology, Vo. 239, No. 2, May 2006, pp. 415-424.

Sylvain Routier et al., "DNA cleavage by hyroxy-salicylidene-ethylendiamine-iron complexes", Nucleic Acids Research, vol. 27, No. 21, 1999, pp. 4160-4166.

J. Lewis et al., "The Preparation and Magnetic Properties of Some Oxy-bridged Binuclear Iron(III) Schiff-base Complexes", J. Chem. Soc., 1967, pp. 1014-1016.

\* cited by examiner

PHOTO WAS TAKEN FROM THIS END TO THE END ON THE OPPOSITE SIDE n=4, P<0.05

$*p<0.05$
$**p<0.01$

Sample mass 150mg, H=200 Oe (1)

AUTO MAGNETIC METAL SALEN COMPLEX COMPOUND

CROSS-REFERENCE TO RELATED APPLICATIONS

This application is a continuation application, filed under 35 U.S.C. §111(a), of International Application PCT/IB2009/007525, filed Nov. 20, 2009, which claimed priority to Japanese Application Nos. 2008-297065, filed Nov. 20, 2008, 2008-299482, filed Nov. 25, 2008 and 2009-177112, filed Jul. 29, 2009, the disclosures of which are hereby incorporated by reference.

BACKGROUND

1. Field

The present invention relates to an auto metal salen complex compound with auto magnetism.

2. Description of the Related Art

Generally speaking, a drug is administered into a living body and reaches the diseased site, and induces a therapeutic effect by locally exhibiting its pharmacological effect at the diseased site, but no medical treatment will be performed if the drug reaches tissues (that is, normal tissues) other than the diseased site.

Accordingly, what is important is how to efficiently deliver the drug to the diseased site. The technique of delivering the drug to the diseased site is referred to as drug delivery, and this is a field in which research and development have been actively conducted in recent years. There are at least two advantages with the foregoing drug delivery. One advantage is that sufficiently high drug concentration can be obtained in the diseased site tissues. A pharmacological effect is not yielded unless the drug concentration at the diseased site is of a given level or higher, and a therapeutic effect cannot be expected with a low concentration.

The second advantage is that the drug is delivered only to the diseased site tissues, whereby it is possible to inhibit side effects to the normal tissues.

This kind of drug delivery exhibits the greatest effect in cancer treatment as an anticancer agent. Since most anticancer agents inhibit the cell growth of cancer cells with active cell division, they also inhibit the cell growth of tissues with active cell division in normal tissues such as the bone marrow, hair roots, digestive tract linings and the like. Thus, a cancer patient that is given an anticancer agent is subject to side effects such as anemia, hair loss, and vomiting. Since these side effects impose a heavy burden on the patient, it is necessary to limit the dosage, and there is a problem in that the pharmacological effect of the anticancer agent cannot be sufficiently obtained.

Among these antineoplastic drugs, an alkyl-based antineoplastic drug is the collective designation of an anticancer agent with the capability of binding an alkyl group ($—CH_2—CH_2—$) to nucleic acid protein and the like which alkylates DNA to inhibit DNA replication, and thereby causes cell death. This effect works irrespective of the cell cycle and also works on the cells of the $G_0$ period, and works strongly on cells that are growing actively, and easily affect the bone marrow, digestive tract linings, germ cells, hair roots and the like.

Moreover, an antimetabolic antineoplastic drug is a compound with a structure that is similar to the metabolite of the nucleic acid and protein synthesis process, affects the cells by inhibiting nucleic acid synthesis, and works specifically on mitotic cells.

Moreover, an antineoplastic antibiotic is a chemical substance that is produced by microorganisms, yields the effects of DNA synthesis inhibition, DNA strand break and the like, and shows antitumor activity.

Moreover, an antimicrotubule agent exhibits an antitumor effect by directly working on the microtubule which plays an important role in maintaining the normal functions of cells by forming a spindle during the cell division or arranging or transporting subcellular organelle. A microtubule inhibitor works on cells and nerve cells with active cell division.

Moreover, a platinum-containing drug inhibits DNA synthesis by creating a DNA chain or interchain coupling or DNA protein coupling. Cisplatin is the representative drug, but it causes significant kidney damage and a large amount of rehydration is required.

Moreover, a hormone analogue-based antineoplastic drug is effective against a hormone dependent tumor. Female hormones or an antiandrogenic agent is administered against male hormone dependent prostatic cancer.

Moreover, a molecularly-targeted drug is a therapeutic method which targets molecules corresponding to molecular biological characteristics which are unique to the respective malignant tumors.

Moreover, a topoisomerase inhibitor is an enzyme that temporarily makes an incision in the DNA and changes the winding and unwinding of the DNA chain. Type I topoisomerase is an enzyme that cuts one strand of a circular DNA, and, after allowing the other strand to pass through, reanneals the cut strand, and the Type II topoisomerase inhibitor is an enzyme that cuts both strands of a double-strand circular DNA, allows a separate double-strand DNA to pass through during that time, and then reanneals the cut strands.

In addition, a nonspecific immune activator inhibits the growth of cancer cells by activating the immune system.

Since most anticancer agents inhibit the cell growth of cancer cells with active cell division, they also inhibit the cell growth of tissues with active cell division in normal tissues such as the bone marrow, hair roots, digestive tract linings and the like. Thus, a cancer patient that is given an anticancer agent is subject to side effects such as anemia, hair loss, and vomiting.

Since these side effects impose a heavy burden on the patient, it is necessary to limit the dosage, and there is a problem in that the pharmacological effect of the anticancer agent cannot be sufficiently obtained. Furthermore, in a worst case scenario, the side effects may kill the patient.

Thus, by delivering the anticancer agent to the cancel cells with drug delivery and exhibiting the pharmacological effect on the cancer cells in a concentrated matter, it is expected that cancer treatment can be performed effectively while inhibiting the side effects. Similar problems are also found in a local anesthetic. A local anesthetic is used for locally treating hemorrhoidal disease, stomatitis, periodontal disease, dental caries, tooth extraction, and itching or pain of the mucous membrane or skin based on surgery. Lidocaine (product name: Xylocaine) is known as a representative local anesthetic. Although Lidocaine is superior in terms of instantaneous effect, it also has an anti-arrhythmic effect.

Moreover, upon performing spinal anesthesia, if Lidocaine is injected as the anesthetic into the spinal fluid, it spreads within the spinal fluid, and, in a worst case scenario, there is a possibility that it will generate critical side effects by reaching the spinal cord in the cervical region and causing the respiratory function to stop.

Thus, by delivering the anticancer agent to the cancel cells with drug delivery and exhibiting the pharmacological effect on the cancer cells in a concentrated matter, it is expected that cancer treatment can be performed effectively while inhibiting the side effects.

Moreover, by preventing the spread of the local anesthetic based on drug delivery, it is expected that the maintenance of the medicinal effect and the alleviation of side effects can be achieved.

As the specific method of drug delivery, for example, there is a method that uses a carrier. With this method, a drug is mounted on a carrier which tends to become concentrated at the diseased site, and the drug is carried to the diseased site.

A magnetic substance is considered highly probable as the carrier, and proposed is a method of attaching a carrier as a magnetic substance to the drug and accumulating the drug at the diseased site based on a magnetic field (for example, refer to Japanese Published Unexamined Patent Application No. 2001-10978).

Nevertheless, when magnetic substance carrier is used as the carrier, there are technical problems in that oral administration is difficult, the carrier molecules are generally enormous, and problems in the binding intensity and affinity between the carrier and drug molecules, and the practical application thereof was difficult to begin with.

Thus, the present inventors proposed a local therapeutic drug in which a side chain for imparting a positive or negative spin/charge density is bound to the basic skeleton of an organic compound, and which has aptitude of a range for being magnetically and jointly delivered as a whole relative to the external magnetic field. When this local therapeutic drug is applied to a human body or an animal, it is retained in the area where a magnetic field is applied locally based on a magnetic field from outside the body, and exhibits its basic medicinal effect at the foregoing area (WO2008/001851). This publication describes an Fe-salen complex as the foregoing drug.

Patent Document 1: Japanese Published Unexamined Patent Application No. 2001-10978
Patent Document 2: WO2008/001851

SUMMARY

The present invention examined whether metal salen other than iron also has ferromagnetic properties, and further examined whether metal salen other than iron possesses useful pharmacological effects similar to the Fe-salen complex. Thus, an object of this invention is to provide a magnetic substance capable of exhibiting therapeutic effects by chemically binding the intended drug to the Fe-salen complex and a metal salen complex other than iron so as to provide magnetic properties to the molecular structure itself of the single magnetic substance compound in which the drug molecules and the metal salen complex containing iron are chemical bound, and consequently delivering the drug molecules to the target diseased site and localized at the diseased site by controlling the magnetic field upon administering this molecular structure to an animal.

MEANS FOR SOLVING THE PROBLEMS

The present invention is characterized as follows in order to achieve the foregoing target.

The present invention is an auto magnetic metal salen complex compound represented by following formula (I) or (II).

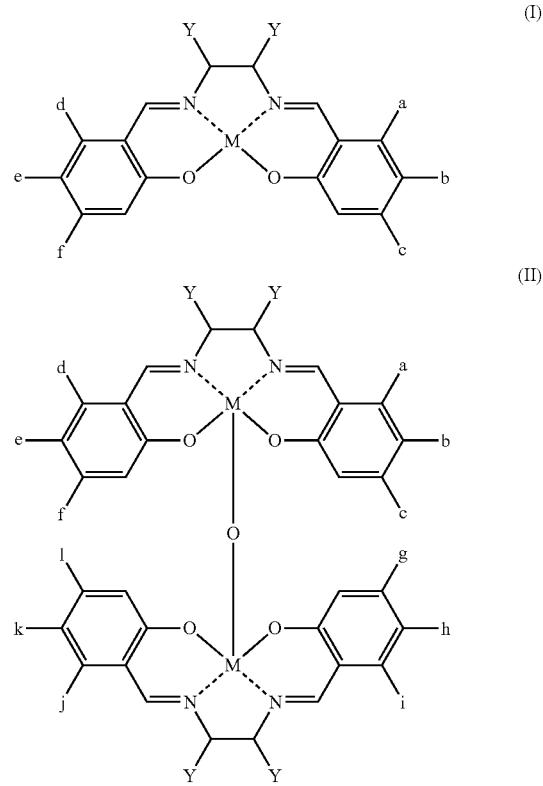

M is Fe, Cr, Mn, Co, Ni, Mo, Ru, Rh, Pd, W, Re, Os, Ir, Pt, Nd, Sm, Eu or Gd, and a to f and Y are respectively hydrogen (excluding the case where, if M is Fe, then a to f and Y are all hydrogen), or one of (A) to (G) below.

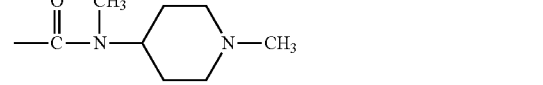

($R_2$ is formed by a plurality of nucleic acids made of adenine, guanine, thymine, cytosine or uracil being bound)

(E) —NHCOH, —$NH_2$, —$NHR_1$ or —$NR_1R_2$ ($R_1R_2$ are the same or alkyl or alkane with a carbon number of 1 to 6)

(F) —$NHR_3$—, —$NHCOR_3$ or —$R_3$ ($R_3$ is a substituent group in which hydrogen or a sensitive group of such as a hydroxyl group was desorbed and bound)

(G) halogen atoms of chlorine, bromine, fluorine or the like

Preferably, $R_3$ has a charge transfer of less than 0.5 electrons (e).

Moreover, $R_3$ is made of any one of the compounds of following formulas (1) to (27).

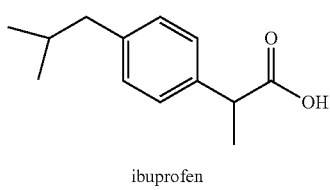

ibuprofen (1): Ibuprofenpiconol, phenylpropionic acid-based analgesic/antiphlogistic

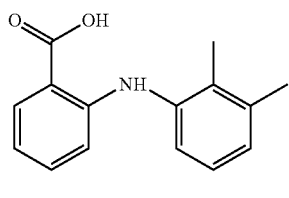

mefenamic acid (2): Mefenamic acid, anthranilic acid-based antiinflammatory agent

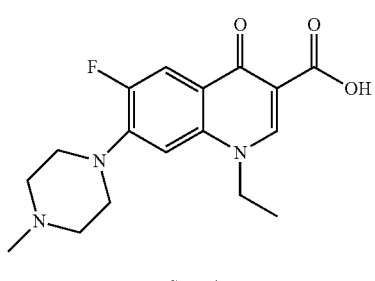

pefloxacin (3): Antihyperlipidemic drug

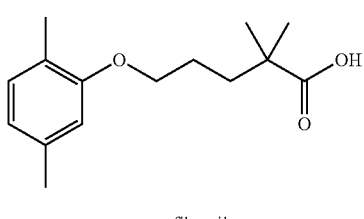

gemfibrozil (4): Antibacterial agent

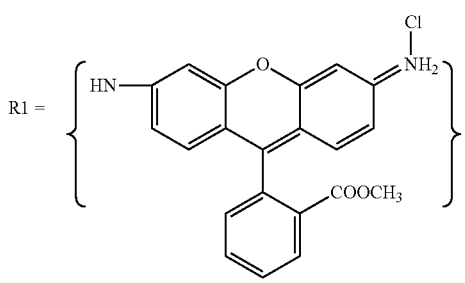

(5): Fluorochrome (Rhodamine)

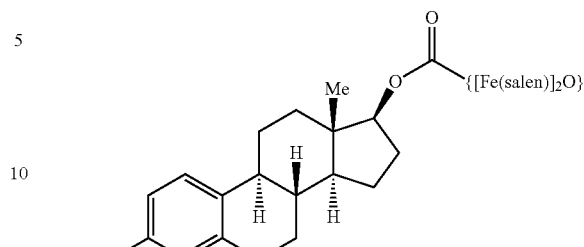

(6): Hormone (Estrogen)

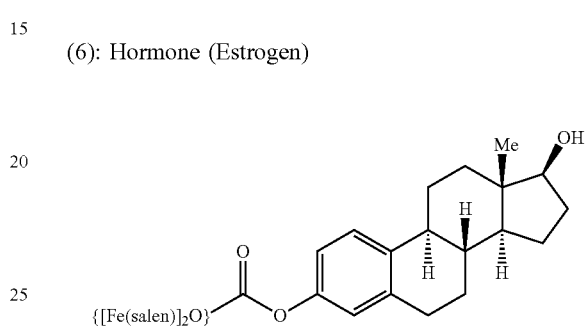

(7): Hormone (Estrogen)

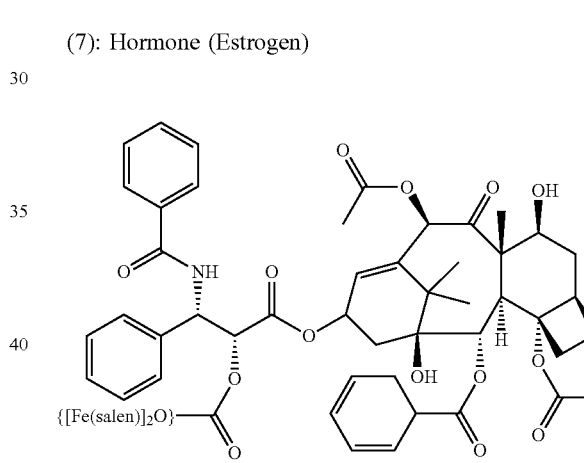

(8): Taxol (Paclitaxel)

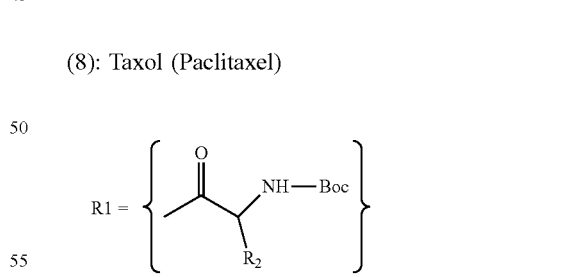

(9): Amino acid (Glycine)

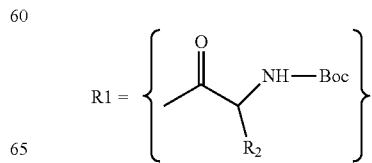

(10): Amino acid (Alanine)
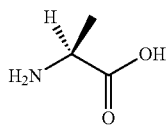
(11): Amino acid (Arginine)
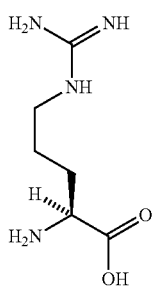
(12): Amino acid (Asparagine)
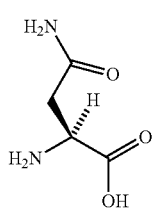
(13): Amino acid (Aspartic Acid)
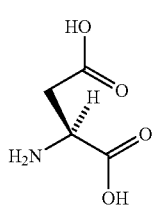
(14): Amino acid (Cysteine)
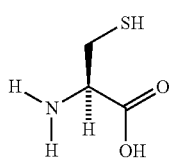
(15): Amino acid (Glutamic Acid)
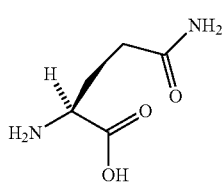
(16): Amino acid (Histidine)
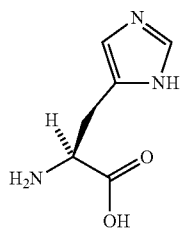 [SMILES: N[C@@H](Cc1cnc[nH]1)C(=O)O]
(17): Amino acid (Isoleucine)
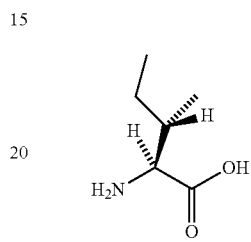
(18): Amino acid (Leucine)
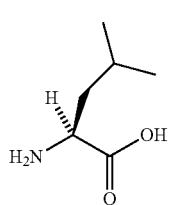
(19): Amino acid (Lysine)
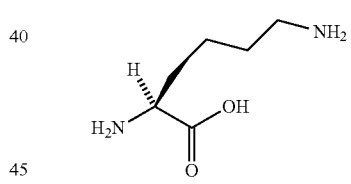
(20): Amino acid (Methionine)
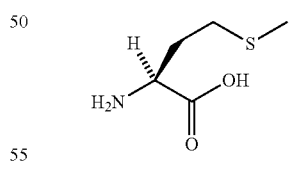
(21): Amino acid (Phenyl Alanine)
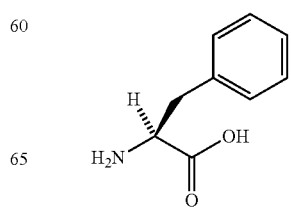

(22): Amino acid (Proline)

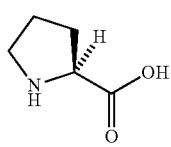

(23): Amino acid (Serine)

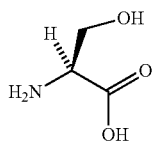

(24): Amino acid (Threonine)

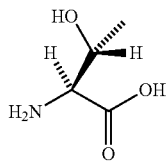

(25): Amino acid (Tryptophan)

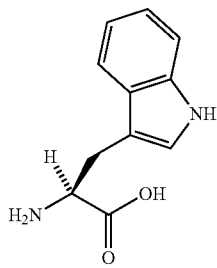 [SMILES: N[C@@H](Cc1c[nH]c2ccccc12)C(=O)O]

(26): Amino acid (Tyrosine)

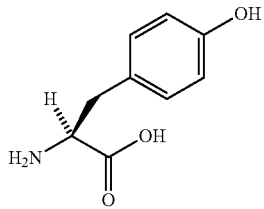 [SMILES: N[C@@H](Cc1ccc(O)cc1)C(=O)O]

(27): Amino acid (Valine)

The present invention is also a local anesthetic containing the foregoing auto magnetic metal salen complex compound, wherein $R_3$ is made of a compound which is any one of the substituent groups of following formulas (28) to (38) including a methyl group and in which hydrogen was desorbed from a compound having a charge transfer of less than 0.5 electrons (e).

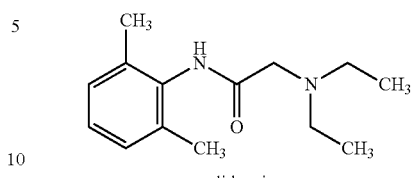

(28) General name: Lidocaine

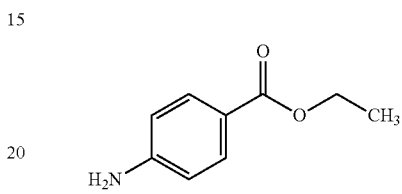

(29) General name: Ethyl aminobenzoate

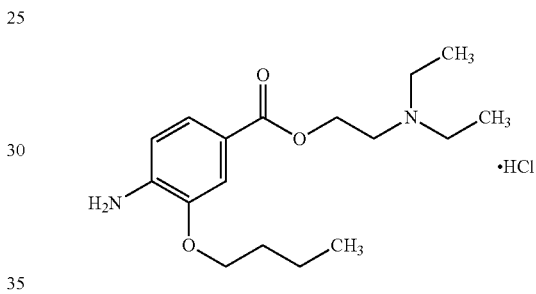

(30) General name: Oxybuprocaine hydrochloride

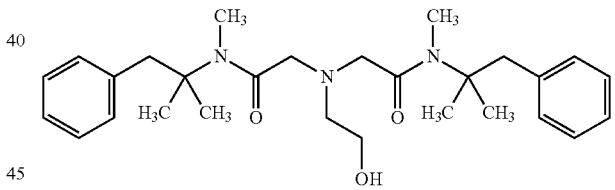

(31) General name: Oxethazaine

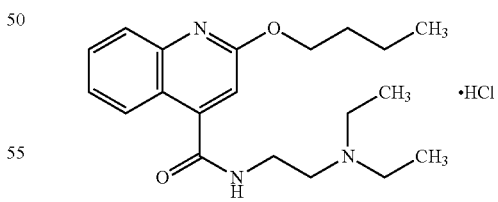

(32) General name: Dibucaine

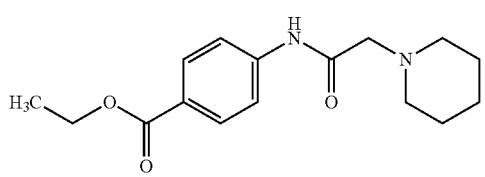 [SMILES: CCOC(=O)c1ccc(NC(=O)CN2CCCCC2)cc1]

(33) General name: Ethyl p-Piperidinoacetylaminobenzoate

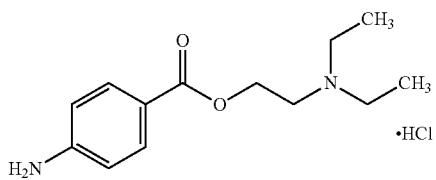

(34) General name: Procaine

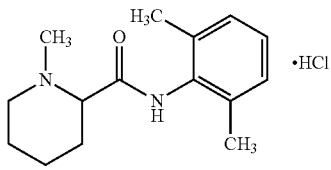 [SMILES: Cc1cccc(C)c1NC(=O)C1CCCCN1C ; Cl]

(35) General name: Mepivacaine

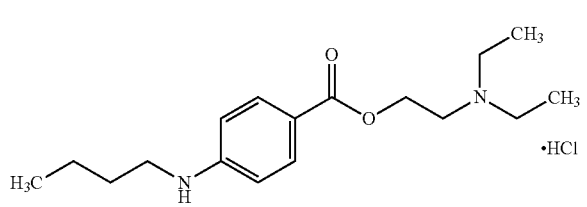 [SMILES: CCCCNc1ccc(C(=O)OCCN(CC)CC)cc1 ; Cl]

(36) General name: Diethylaminoethyl p-Butylaminobenzoate hydrochloride

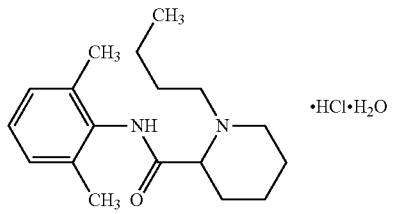 [SMILES: CCCCN1CCCCC1C(=O)Nc1c(C)cccc1C]

(37) General name: Bupivacaine hydrochloride

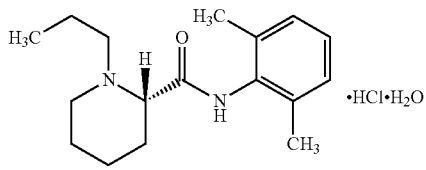 [SMILES: CCCN1CCCC[C@H]1C(=O)Nc1c(C)cccc1C]

(38) General name: Ropivacaine hydrochloride hydrate

The present invention is also an antineoplastic drug containing the foregoing auto magnetic metal salen complex compound, wherein $R_3$ is any one of the compounds of following formulas (39) to (103), which is formed by being bound to a host framework of the compound of foregoing formula I or II at a portion of the binding group formed based on the desorption of hydrogen (provided, however, that is the compound of (83), a cyano group (—CN) is the binding group).

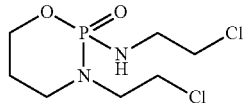 [SMILES: O=P1(NCCCl)OCCCN1CCCl]

(39) General name: Ifosfamide, alkyl-based antineoplastic drug

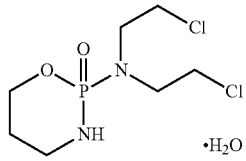 [SMILES: O=P1(N(CCCl)CCCl)NCCCO1 ; O]

(40) General name: Cyclophosphamide, alkyl-based antineoplastic drug

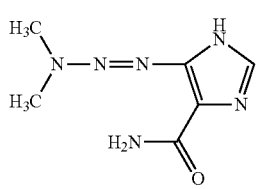

(41) General name: Dacarbazine, alkyl-based antineoplastic drug

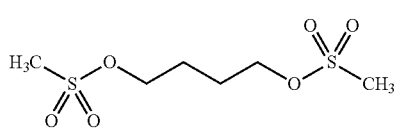

(42) General name: Busulfan, alkyl-based antineoplastic drug

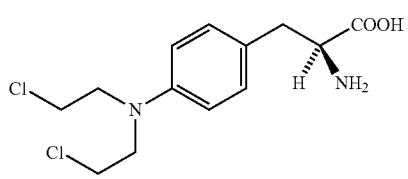 [SMILES: N[C@@H](Cc1ccc(N(CCCl)CCCl)cc1)C(=O)O]

(43) General name: Melphalan, alkyl-based antineoplastic drug

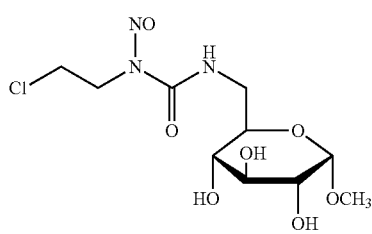

(44) General name: Ranimustine, alkyl-based antineoplastic drug

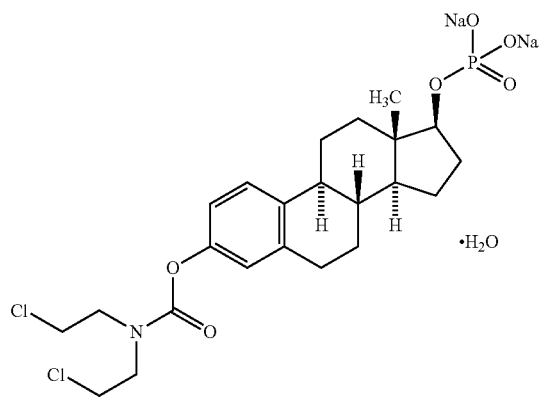

(45) General name: Estramustine sodium phosphate, alkyl-based antineoplastic drug

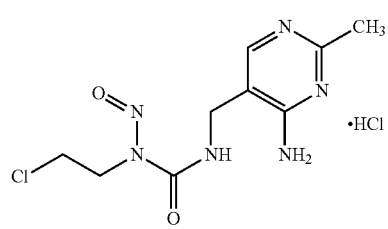 [SMILES: Cc1ncc(CNC(=O)N(CCCl)N=O)c(N)n1 ; Cl]

(46) General name: Nimustine hydrochloride, alkyl-based antineoplastic drug

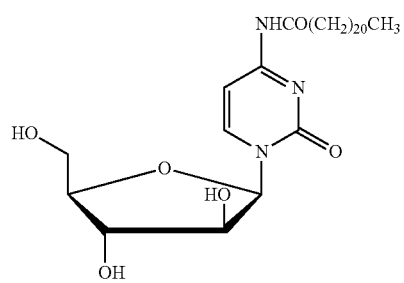

(47) General name: Enocitabin, antimetabolic antineoplastic drug

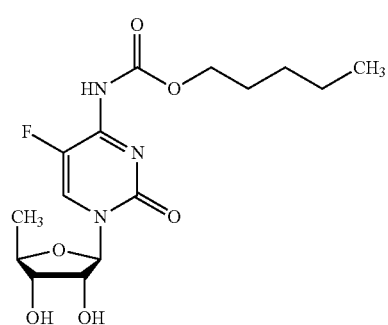

(48) General name: Capecitabine, antimetabolic antineoplastic drug

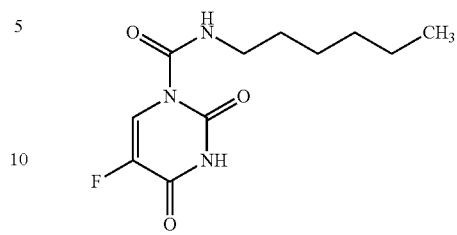

(49) General name: Camofur, antimetabolic antineoplastic drug

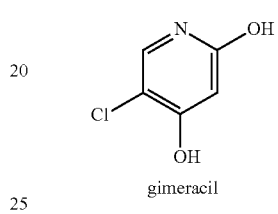

gimeracil

(50) General name: Gimeracil, antimetabolic antineoplastic drug

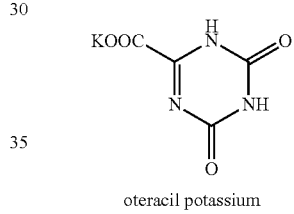

oteracil potassium

(51) General name: Oteracil potassium, antimetabolic antineoplastic drug

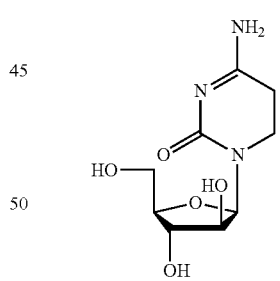

(52) General name: Cytarabine, antimetabolic antineoplastic drug

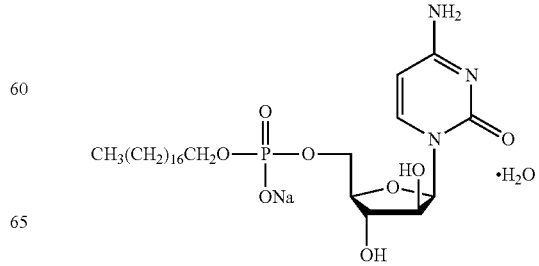

(53) General name: Cytarabine ocfosfate, antimetabolic antineoplastic drug

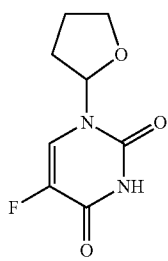 [SMILES: O=c1[nH]c(=O)n(C2CCCO2)cc1F]

(54) General name: Tegafur, antimetabolic antineoplastic drug

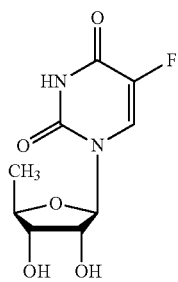

(55) General name: Doxifluridine, antimetabolic antineoplastic drug

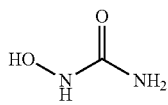

(56) General name: Hydroxycarbamide, antimetabolic antineoplastic drug

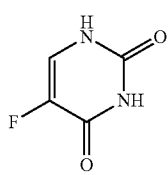

(57) General name: Fluorouracil, antimetabolic antineoplastic drug

(58) General name: Mercaptopurine hydrate, antimetabolic antineoplastic drug

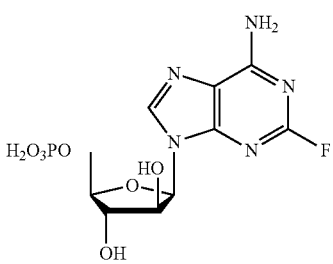

(59) General name: Fludarabine phosphate, antimetabolic antineoplastic drug

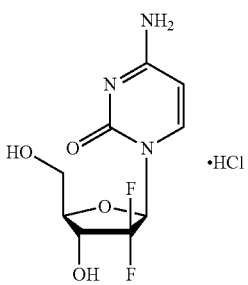

(60) General name: Gemcitabine hydrochloride, antimetabolic antineoplastic drug

(61) General name: Actinomycin D, antineoplastic antibiotic

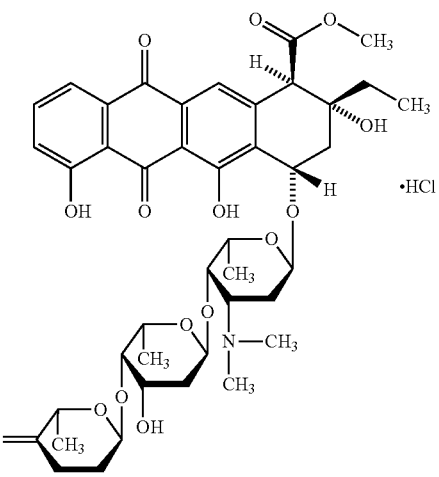

(62) General name: Aclarubicin hydrochloride, antineoplastic antibiotic

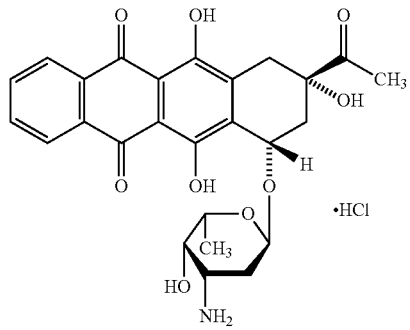

(63) General name: Idarubicin hydrochloride, antineoplastic antibiotic

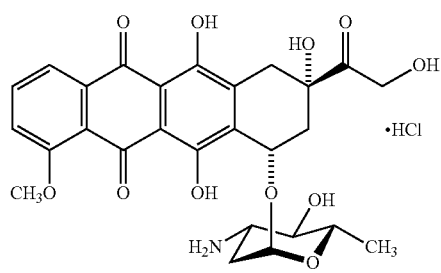

(64) General name: Epirubicin hydrochloride, antineoplastic antibiotic

(65) General name: Zinostatin stimalamer, antineoplastic antibiotic

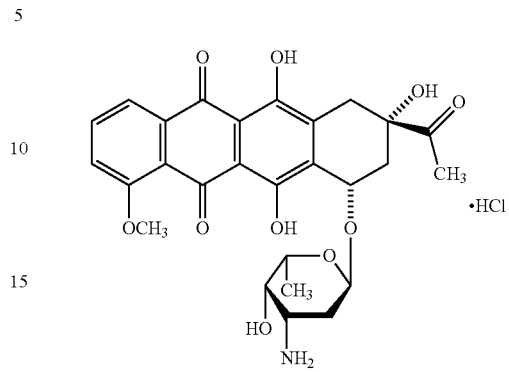

(66) General name: Daunorubicin hydrochloride, antineoplastic antibiotic

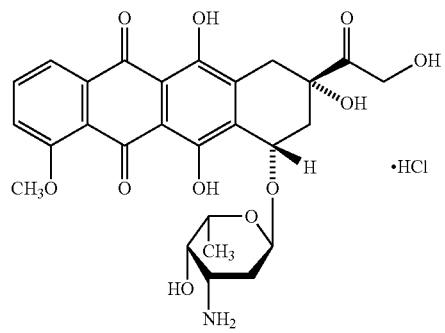

(67) General name: Doxorubicin hydrochloride, antineoplastic antibiotic

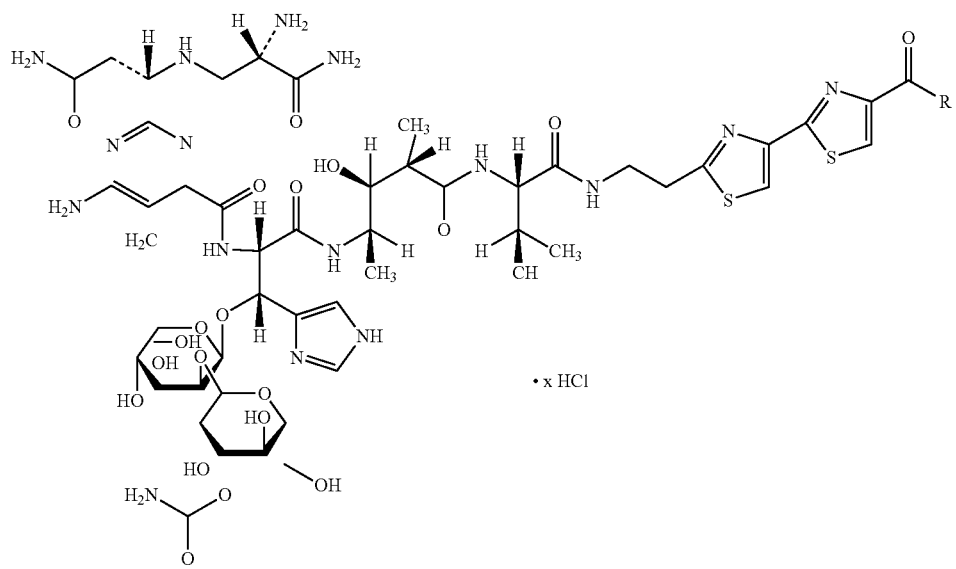

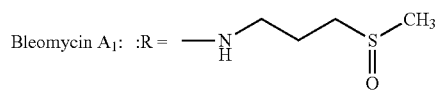

-continued
Bleomycin demthyl-A₂ :R = 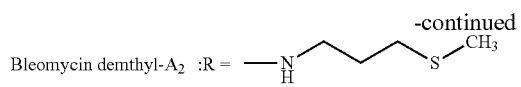
Bleomycin A₂: :R = 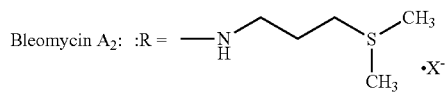 ·X⁻
Bleomycin A₂₋ₐ: :R = 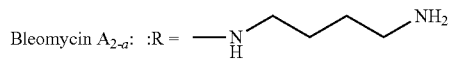
Bleomycin A₂₋ᵦ: :R = 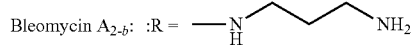
Bleomycin A₅: :R = 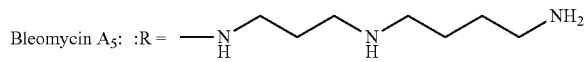
Bleomycin B₁: :R = —NH₂
Bleomycin B₂: :R = 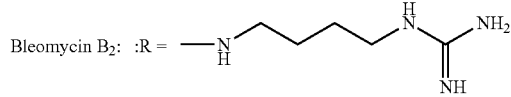
Bleomycin B₄: :R = 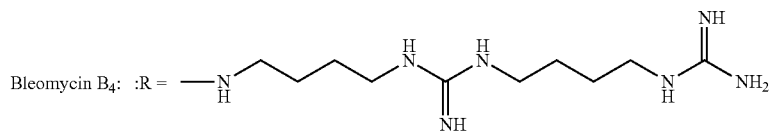
(68) General name: Bleomycin hydrochloride, antineoplastic antibiotic
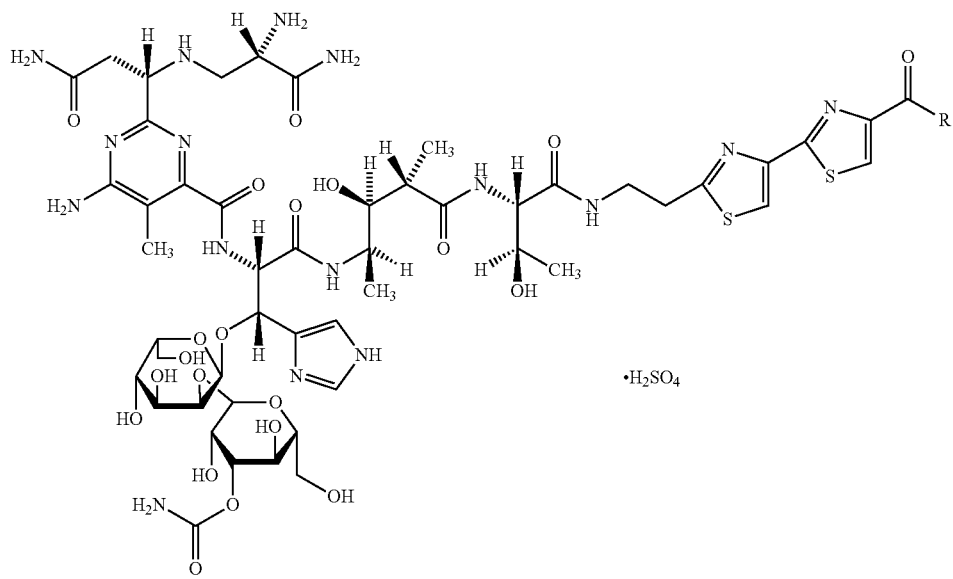
·H₂SO₄
R = 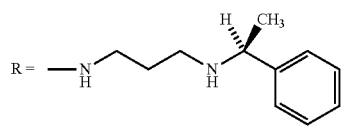

(69) General name: Peplomycin hydrochloride, antineoplastic antibiotic

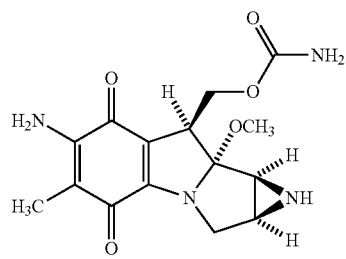 [SMILES: CO[C@@]12[C@H](COC(N)=O)C3=C(C(=O)C(C)=C(N)C3=O)N1C[C@@H]1N[C@@H]12]

(70) General name: Mitomycin C, antineoplastic antibiotic

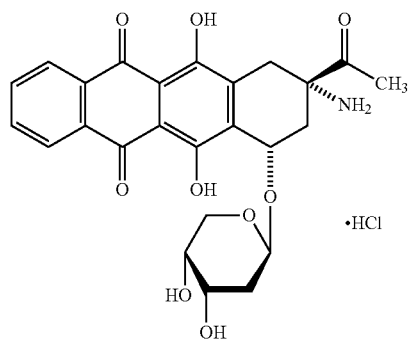 [SMILES: CC(=O)[C@]1(N)Cc2c(O)c3c(c(O)c2[C@@H](O[C@H]2C[C@@H](O)[C@H](O)CO2)C1)C(=O)c1ccccc1C3=O ; Cl]

(71) General name: Amrubicin hydrochloride, antineoplastic antibiotic

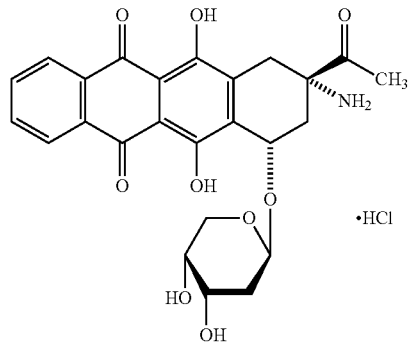 [SMILES: CC(=O)[C@]1(N)Cc2c(O)c3c(c(O)c2[C@@H](O[C@H]2C[C@@H](O)[C@H](O)CO2)C1)C(=O)c1ccccc1C3=O ; Cl]

(72) General name: Pirarubicine hydrochloride, antineoplastic antibiotic

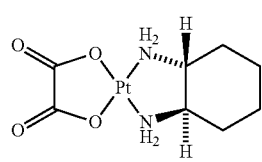

(73) General name: Pirarubicine hydrochloride, antineoplastic antibiotic

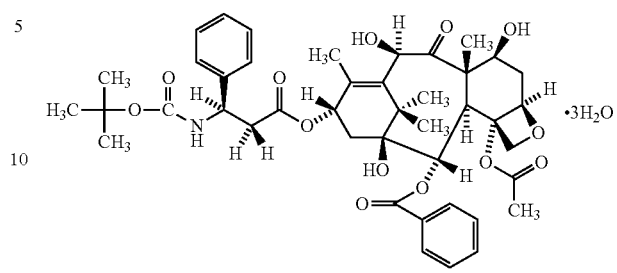

(74) General name: Docetaxel hydrate, antimicrotubule agent

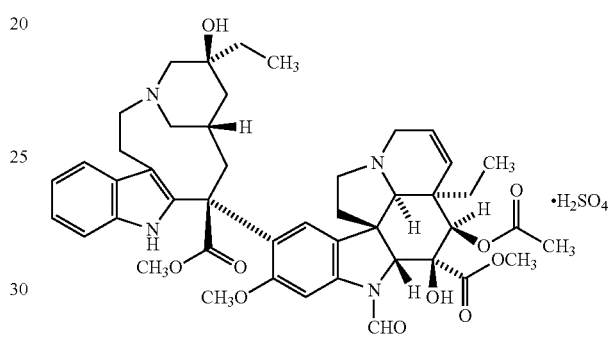

(75) General name: Vincristine sulfate, antimicrotubule agent

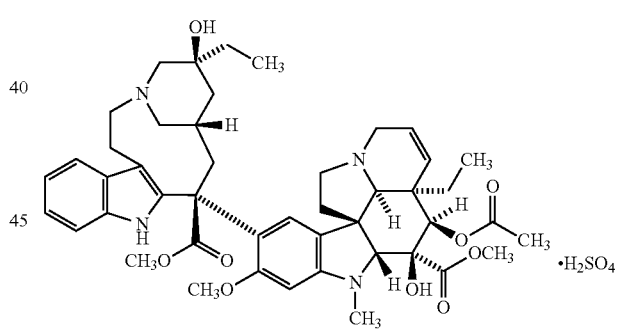

(76) General name: Vinblastine sulfate, antimicrotubule agent

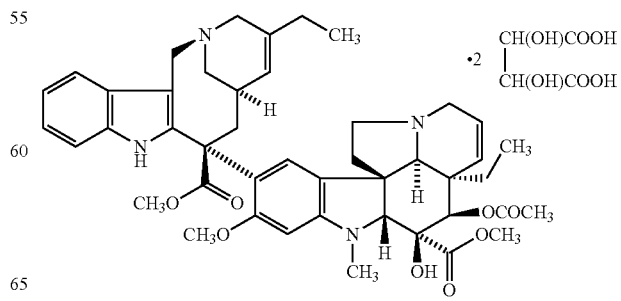

(77) General name: Vinorelbine ditartrate, antimicrotubule agent

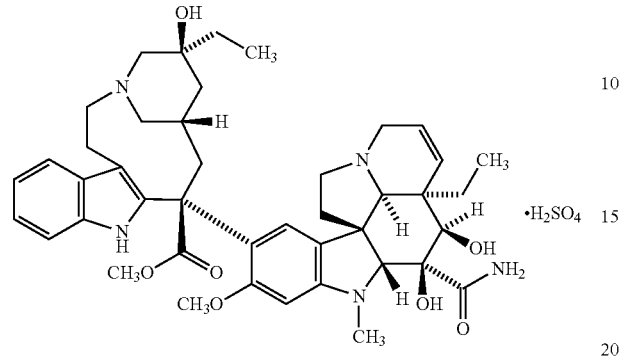

(78) General name: Vindesine sulfate, antimicrotubule agent

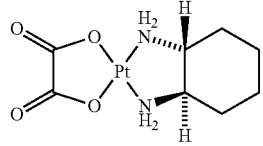

(79) General name: Oxaliplatin, platinum-containing drug

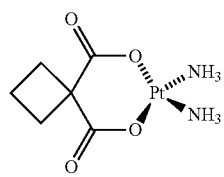

(80) General name: Carboplatin, platinum-containing drug

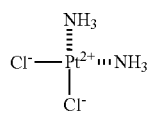

(81) General name: Cisplatin, platinum-containing drug

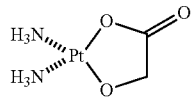

(82) General name: Nedaplatin, platinum-containing drug

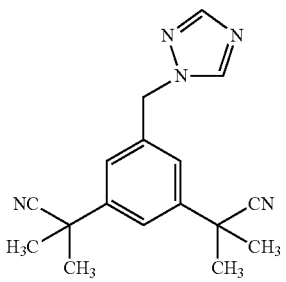 [SMILES: CC(C)(C#N)c1cc(Cn2cncn2)cc(C(C)(C)C#N)c1]

(83) General name: Anastorozole, hormone analogue

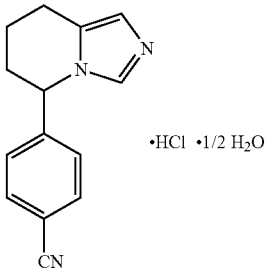 [SMILES: N#Cc1ccc(C2CCCc3cncn32)cc1]

(84) General name: Afema, hormone analogue

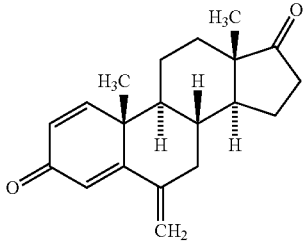

(85) General name: Exemestane, hormone analogue

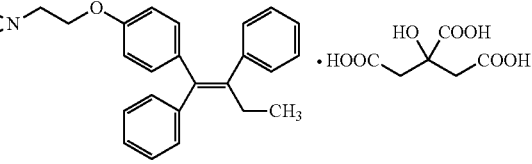

(86) General name: Toremifene citrate, hormone analogue

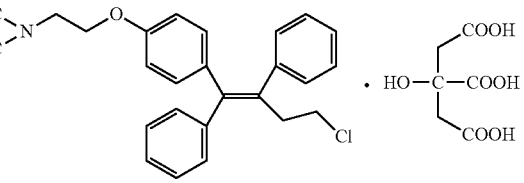

(87) General name: Toremifene citrate, hormone analogue

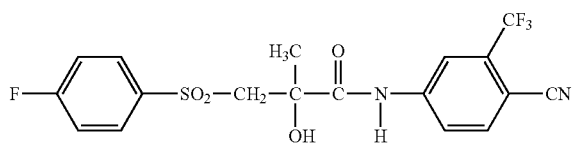

(88) General name: Bicalutamide, hormone analogue

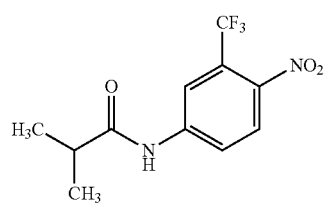 [SMILES: CC(C)C(=O)Nc1ccc([N+](=O)[O-])c(C(F)(F)F)c1]

(89) General name: Flutamide, hormone analogue

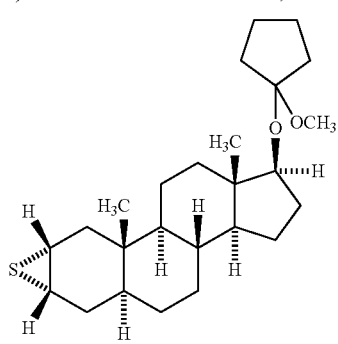

(90) General name: Mepitiostane, hormone analogue

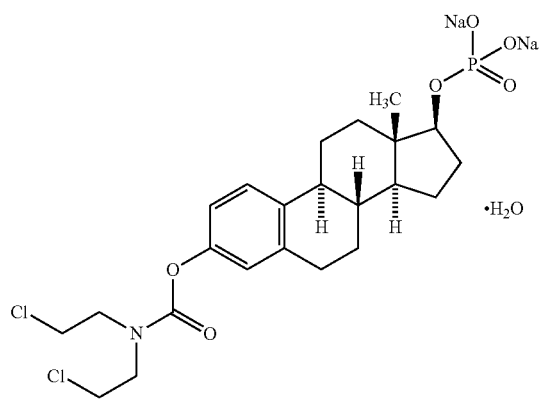

(91) General name: Estramustine sodium phosphate, hormone analogue

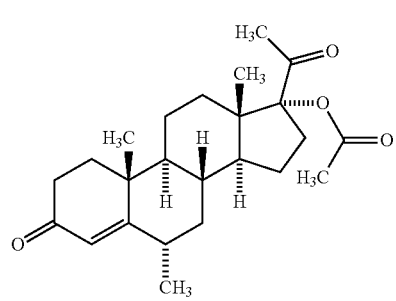

(92) General name: Medroxyprogesterone acetate, hormone analogue

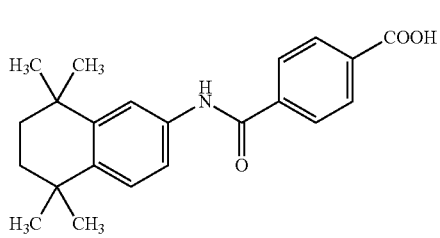 [SMILES: CC1(C)CCC(C)(C)c2cc(NC(=O)c3ccc(C(=O)O)cc3)ccc21]

(93) General name: Tamibarotene, molecular target drug

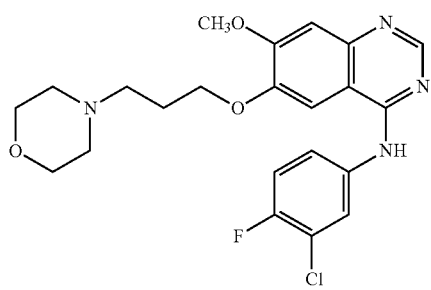

(94) General name: Gefitinib, molecular target drug

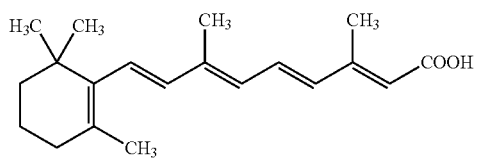 [SMILES: CC1=C(/C=C/C(C)=C/C=C/C(C)=C/C(=O)O)C(C)(C)CCC1]

(95) General name: Tretinoin, molecular target drug

(96) General name: Imatinib mesylate, molecular target drug

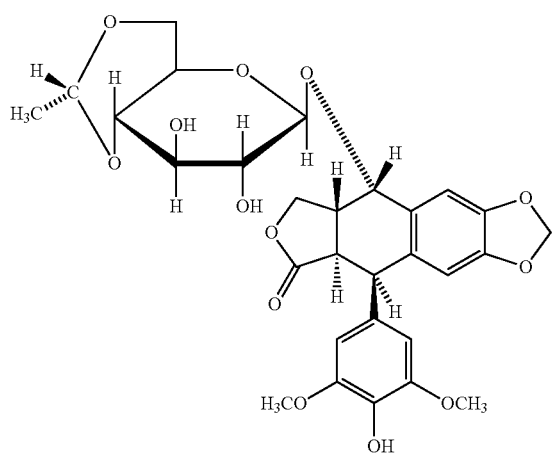

(97) General name: Etoposide, topoisomerase inhibitor
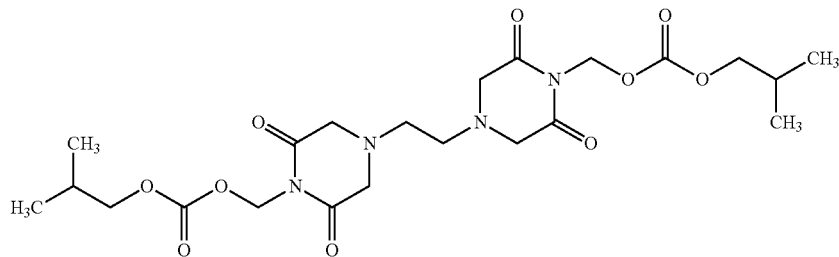 [SMILES: CC(C)COC(=O)OCN1C(=O)CN(CCN2CC(=O)N(COC(=O)OCC(C)C)C(=O)C2)CC1=O]
(98) General name: Sobuzoxane, topoisomerase inhibitor
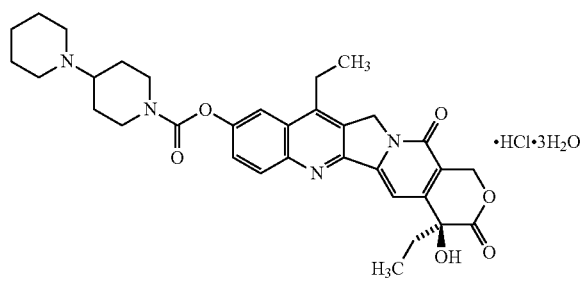 [SMILES: CCc1c2c(nc3ccc(OC(=O)N4CCC(N5CCCCC5)CC4)cc13)-c1cc3c(c(=O)n1C2)COC(=O)[C@]3(O)CC]
(99) General name: Irinotecan hydrochloride, topoisomerase inhibitor
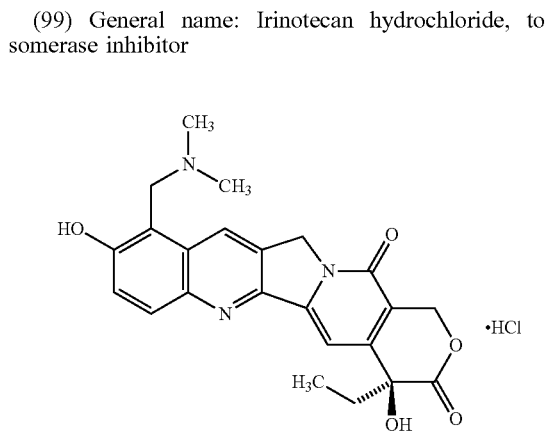
(100) General name: Nogitecan hydrochloride, topoisomerase inhibitor
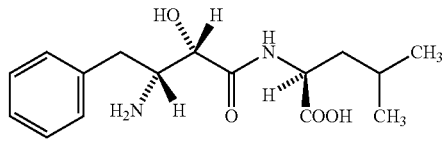 [SMILES: CC(C)C[C@H](NC(=O)[C@@H](O)[C@H](N)Cc1ccccc1)C(=O)O]
(101) General name: Ubenimex, nonspecific immune activator
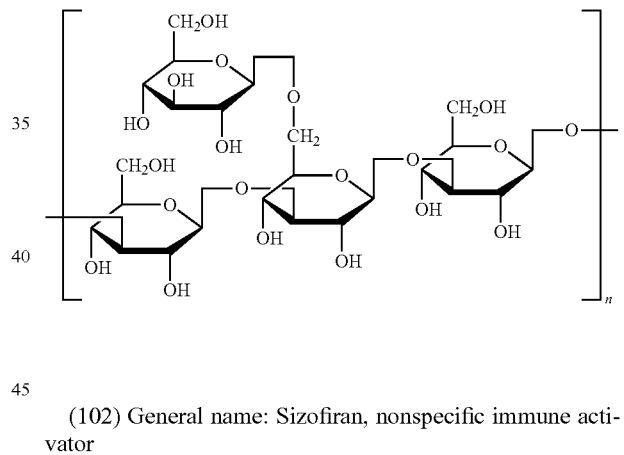
(102) General name: Sizofiran, nonspecific immune activator
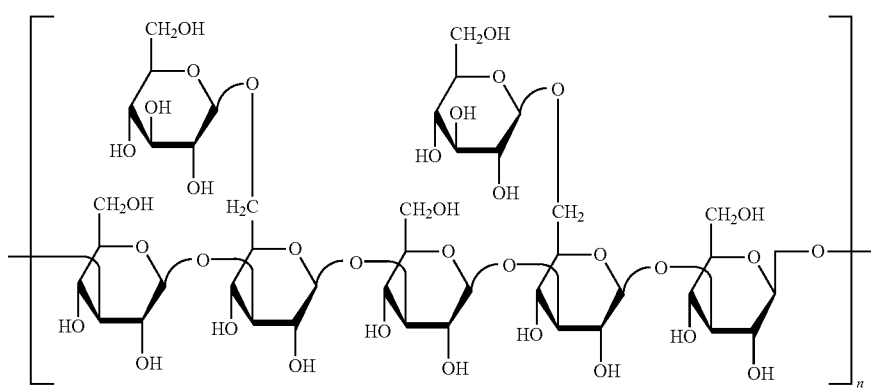

(103) General name: Lentinan, nonspecific immune activator

The present invention is also an antineoplastic drug containing the auto magnetic metal salen complex compound according to claim 1 or claim 2, wherein $R_3$ is made of any one of the compounds of following formulas (104) to (109).

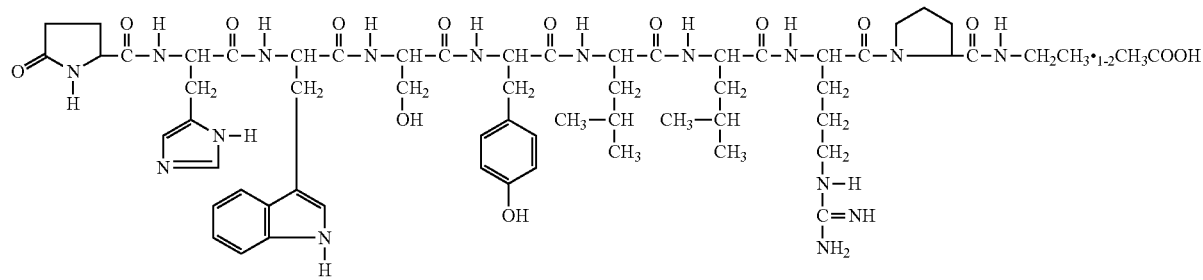

(104) (Product name: Leuprorelin; General name: Leuprorelin acetate, anticancer drug)

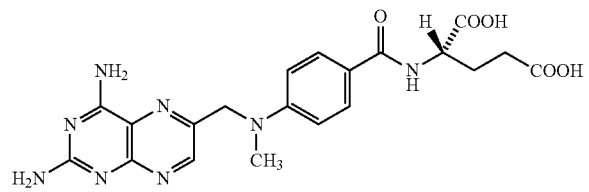 [SMILES: CN(Cc1cnc2nc(N)nc(N)c2n1)c1ccc(C(=O)N[C@@H](CCC(=O)O)C(=O)O)cc1]

(105) (Product name: Methotrexate; General name: Methotrexate, anticancer drug)

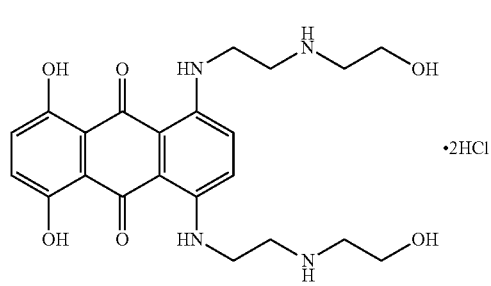 [SMILES: O=C1c2c(O)ccc(O)c2C(=O)c2c(NCCNCCO)ccc(NCCNCCO)c21]

(106) (Product name: Novantrone; General name: Mitoxantrone hydrochloride, anticancer drug)

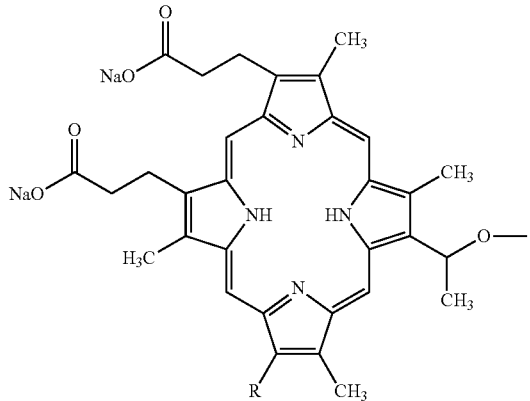

(107) (Product name: Photofrin; General name: Porfimer sodium, anticancer drug)

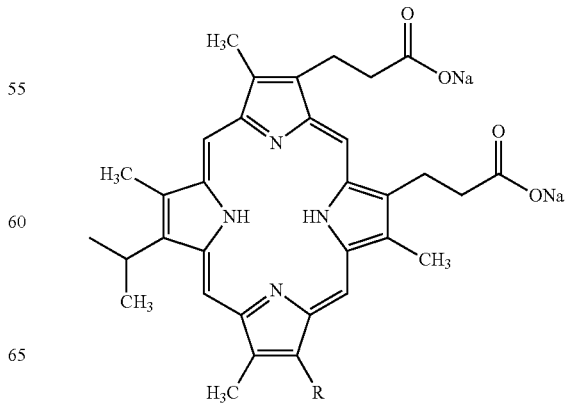

(108) (Product name: Photofrin; General name: Porfimer sodium, anticancer drug)

(109) (Product name: Mylotarg; General name: Gemtuzumab ozogamicin, anticancer drug)

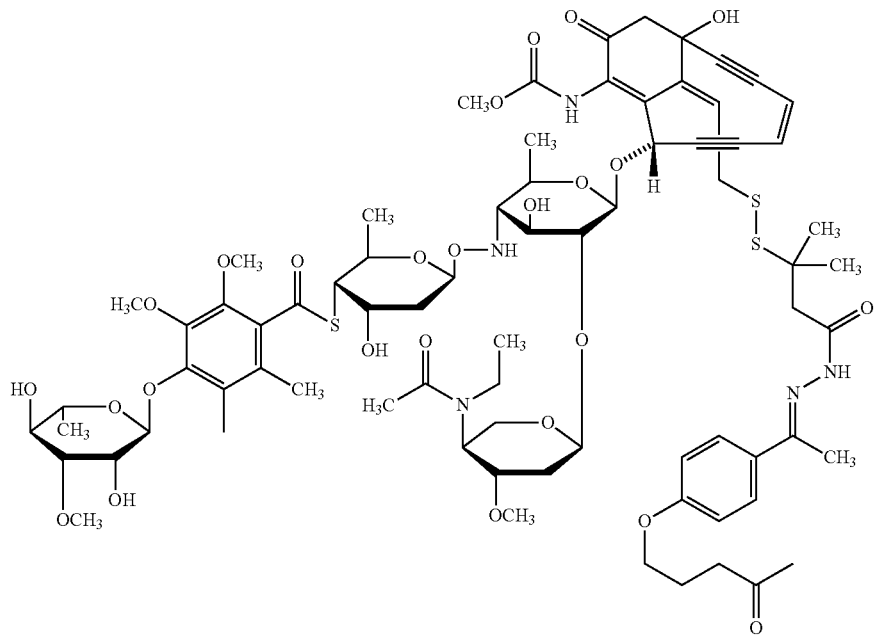

The present invention is also an auto magnetism-imparting metal salen complex molecule, wherein at least one location of 1 to 8 of following compound III bonds with another compound and imparts magnetic properties to the other compound.

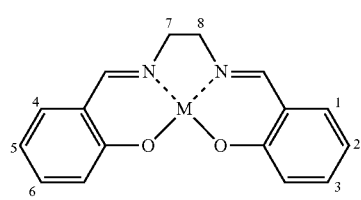

(III)

M is Fe, Cr, Mn, Co, Ni, Mo, Ru, Rh, Pd, W, Re, Os, Ir, Pt, Nd, Sm, Eu or Gd.

The present invention is also an auto magnetism-imparting metal salen complex molecule, wherein at least one location of 1 to 8 and at least one location of 9 to 16 of following compound IV bond with another compound and impart magnetic properties to the other compound.

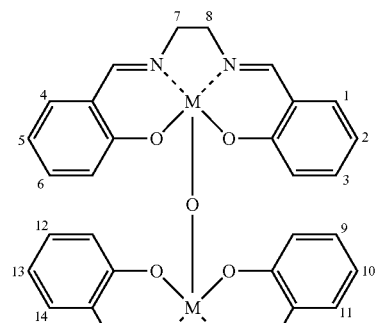

(IV)

M is Fe, Cr, Mn, Co, Ni, Mo, Ru, Rh, Pd, W, Re, Os, Ir, Pt, Nd, Sm, Eu or Gd.

The present invention is also an intermediate made of the following compound for manufacturing a magnetic metal complex.

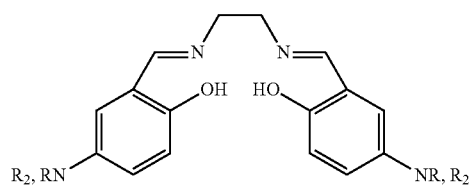

$R_1$ and $R_2$ are respectively hydrogen or one is hydrogen and the other is —COX (X is —OH or a halogen atom).

The present invention is also a method of manufacturing a magnetic substance made by binding medicinal molecules via an amide group at the location(s) of 2 and/or 5 of following compound III.

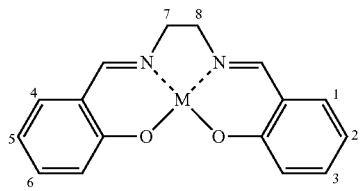
(III)

M is Fe, Cr, Mn, Co, Ni, Mo, Ru, Rh, Pd, W, Re, Os, Ir, Pt, Nd, Sm, Eu or Gd.

The present invention is a method of manufacturing a magnetic substance made by binding medicinal molecules via an amide group at the locations of 5 and 10 or the locations of 2 and 13 or the locations of 2, 5, 10, and 13 of following compound IV.

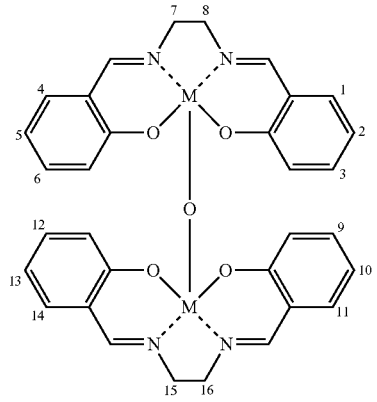
(IV)

M is Fe, Cr, Mn, Co, Ni, Mo, Ru, Rh, Pd, W, Re, Os, Ir, Pt, Nd, Sm, Eu or Gd.

The present invention is also a method of manufacturing an auto magnetic compound, wherein a medicinal component having a medicinal molecular structure (X) is reacted with

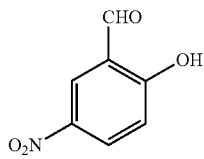

to generate

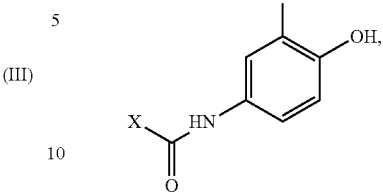

this is further reacted with ethylenediamine to generate

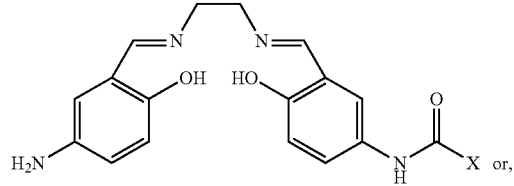
or,

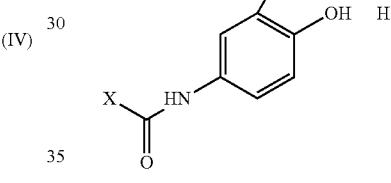

and this is further reacted with metal halide to obtain

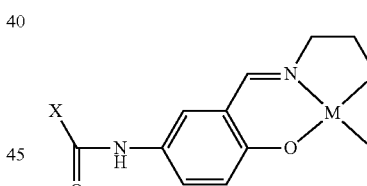
or,

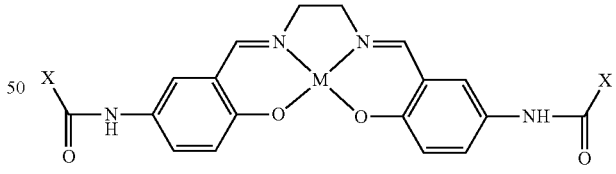

The present invention is also a method of manufacturing an auto magnetic compound, wherein ethylenediamine is reacted with

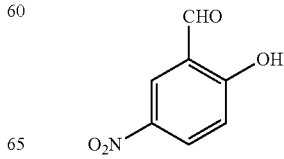

to generate

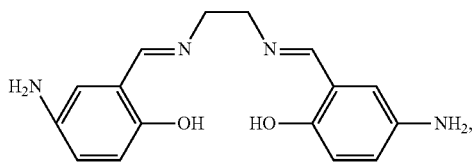 [SMILES: Nc1ccc(O)c(/C=N/CC/N=C/c2cc(N)ccc2O)c1]

this is reacted with a medicinal component having a medicinal molecular structure (X), and further reacted with metal halide to obtain

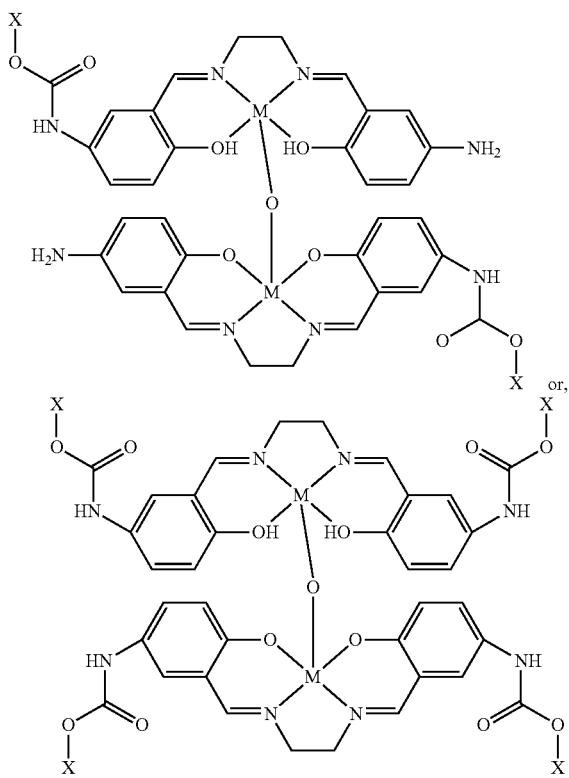

The present invention is also a method of manufacturing an auto magnetic compound, wherein

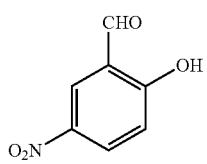

is reacted with a medicinal molecular structure (X) to generate

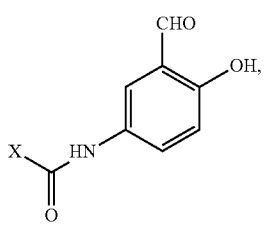

and this is reacted with ethylenediamine to generate

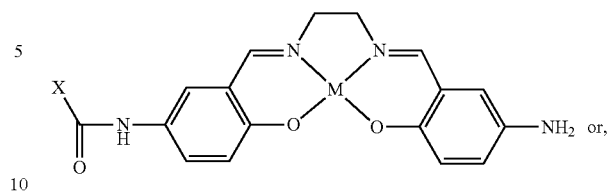

and this is reacted with metal halide to obtain

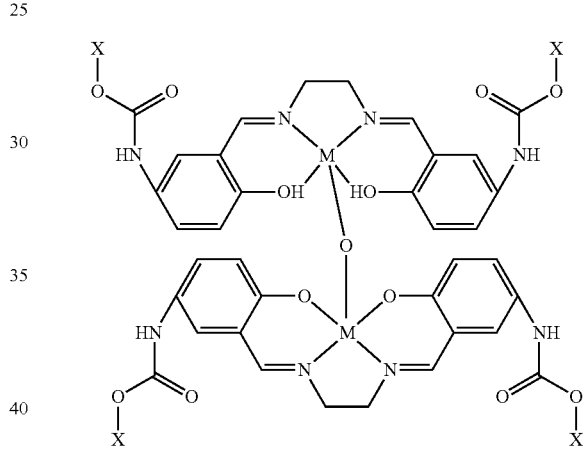

EFFECT

According to the present invention, it was confirmed that the metal salen other than iron also possesses magnetic properties, and it was further confirmed that the metal salen other than iron possesses useful pharmacological effects similar to the Fe-salen complex. Thus, it was possible to provide a magnetic substance capable of exhibiting therapeutic effects by chemically binding the intended drug to the Fe-salen complex and a metal salen complex other than iron so as to provide magnetic properties to the molecular structure itself of the single magnetic substance compound in which the drug molecules and the metal salen complex containing iron are chemical bound, and consequently delivering the drug molecules to the target diseased site and localized at the diseased site by controlling the magnetic field upon administering this molecular structure to an animal.

BRIEF DESCRIPTION OF THE DRAWINGS

FIG. 14 is a graph showing the NMR peak of the Cr-salen.

DESCRIPTION OF EMBODIMENTS

Figure 1:
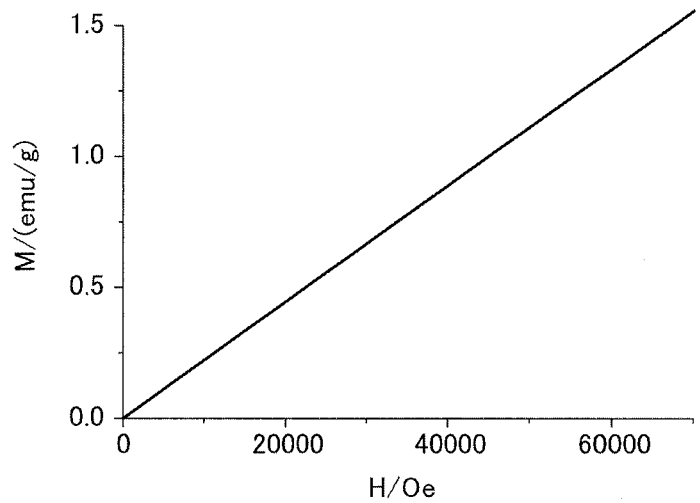
FIG. 1 is a 37° C. (310K) magnetic field-magnetization curve of the Mn-salen complex.

Embodiments of the present invention are now explained. The following embodiments are illustrated for explaining the present invention, and are not intended to limit this invention to these embodiments. The present invention can be implemented in various modes so as long as they do not deviate from the gist thereof.

The magnetic metal complex of the present invention itself possesses a pharmacological effect (for example, anti-cancer effect), and has properties of chemically bonding with other drugs and imparting magnetic properties to those drugs.

Example 1

The metal salen complex of the present invention was manufactured as follows.

Step 1:

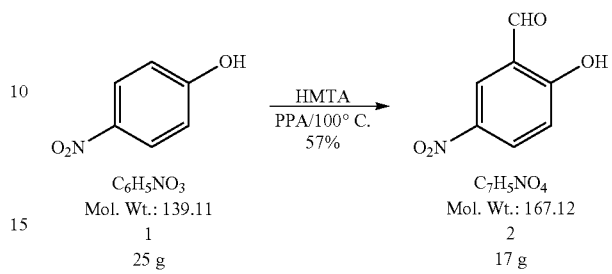

A mixture of 4-nitrophenol (25 g, 0.18 mol), hexamethylene tetramine (25 g, 0.18 mol), and polyphosphoric acid (200 ml) was agitated for 1 hour at 100° C. Subsequently, the mixture was placed in 500 ml of ethyl acetate and 1 L of water, and agitated until the mixture became completely dissolved. In addition, as a result of additionally adding 400 ml of ethyl acetate to the foregoing solution, the solution separated into 2 phases. The water phase was removed and the remaining compound was washed twice with a saline solvent, and, as a result of drying with anhydrous $MgSO_4$, it was possible to synthesize a compound 2 of 17 g (yield 57%).

Step 2:

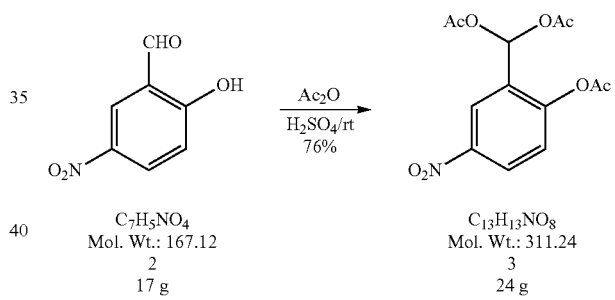

The compound 2 (17 g, 0.10 mol), acetic anhydride (200 ml), and $H_2SO_4$ (small amount) were agitated for 1 hour at room temperature. The obtained solution was mixed in ice water (2 L) for 0.5 hours, and hydrolysis was performed. When the obtained solution was filtered and dried in the atmosphere, a white powdery substance was obtained. As a result of recrystallizing the powder with a solution containing ethyl acetate, 24 g of compound 3 (yield 76%) was obtained as white crystals.

Step 3:

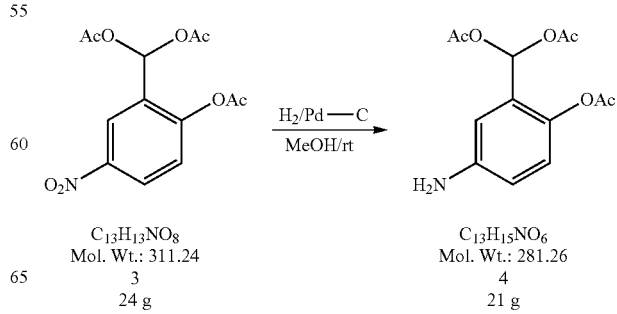

A mixture of carbon (2.4 g) carrying 10% of palladium was reduced to the compound 3 (24 g, 77 mmol) and methanol (500 ml) in a hydrogen reduction atmosphere overnight at 1.5 atmospheric pressure. After completion, the product was filtered with a filter, and it was possible to synthesize a brown oily compound 4 (21 g).

Steps 4, 5:

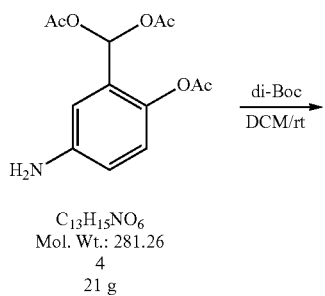

C$_{13}$H$_{15}$NO$_6$
Mol. Wt.: 281.26
4
21 g

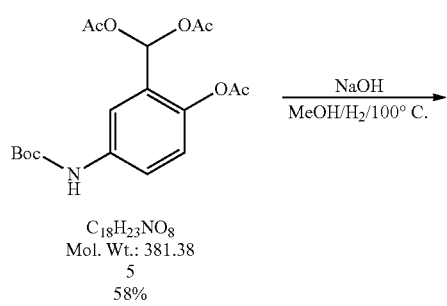

C$_{18}$H$_{23}$NO$_8$
Mol. Wt.: 381.38
5
58%

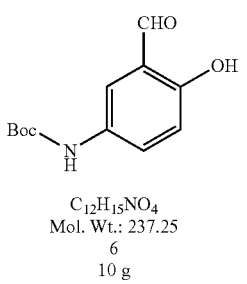

C$_{12}$H$_{15}$NO$_4$
Mol. Wt.: 237.25
6
10 g

The compound 4 (21 g, 75 mmol) and di(tert-butyl) dicarbonate (18 g, 82 mmol) were agitated with dichloromethane (DCM) (200 ml) overnight in a nitrogen atmosphere. The obtained solution was vaporized in a vacuum and thereafter dissolved in methanol (100 ml). Subsequently, sodium hydroxide (15 g, 374 mmol) and water (50 ml) were added and refluxed for 5 hours.

The product was thereafter cooled, filtered with a filter, washed with water, and dried in a vacuum, and a brown compound was thereby obtained. The obtained compound was twice subject to flash chromatography using silica gel, whereby 10 g of a compound 6 (yield 58%) was obtained.

Step 6:

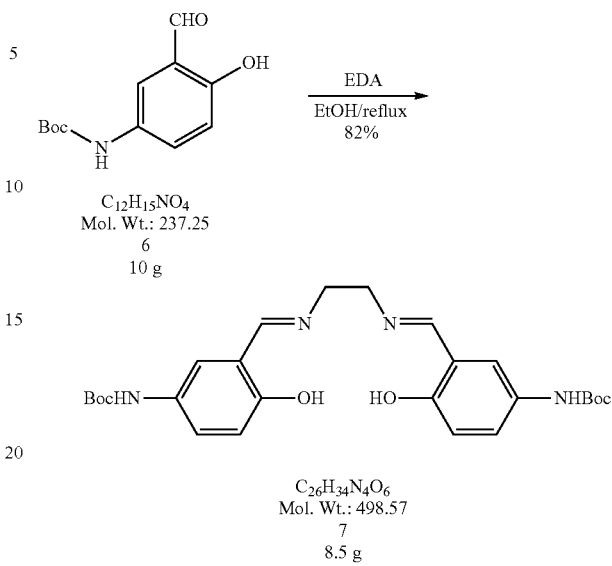

C$_{12}$H$_{15}$NO$_4$
Mol. Wt.: 237.25
6
10 g

C$_{26}$H$_{34}$N$_4$O$_6$
Mol. Wt.: 498.57
7
8.5 g

The compound 6 (10 g, 42 mmol) was placed in 400 ml of dehydrated ethanol, refluxed while being heated, and several drops of ethylenediamine (1.3 g, 21 mmol) was added to 20 ml of dehydrated ethanol and agitated for 0.5 hours. The mixed solution was cooled in a vessel made of ice and mixed for 15 minutes.

Subsequently, the product was washed with 200 ml of ethanol and filtered and dried in a vacuum, and it was possible to synthesize a compound 7 of 8.5 g (yield 82%).

Step 7:

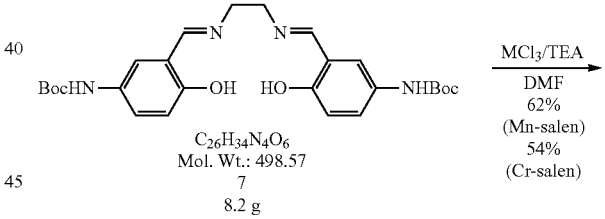

C$_{26}$H$_{34}$N$_4$O$_6$
Mol. Wt.: 498.57
7
8.2 g

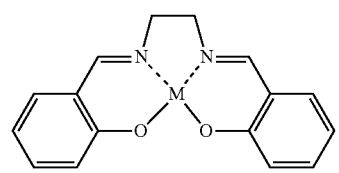

Complex A
5.7 g (Mn-salen)
5.0 g (Cr-salen)

The compound 7 (8.2 g, 16 mmol) and triethylamine (22 ml, 160 mmol) were placed in N, N-dimethylformamide (abbreviated as DMF) (50 ml), and a solution obtained by adding FeCl$_3$(.4H$_2$O) (2.7 g, 16 mmol) to 10 ml of methanol in the case of Fe-salen, adding MnCl$_3$.4H$_2$O (2.7 g, 16 mmol) in the case of Mn-salen, and adding CrCl$_3$.4H$_2$O (2.7 g, 16 mmol) in the case of Cr-salen was mixed under a nitrogen atmosphere.

As a result of mixing the product at room temperature under a nitrogen atmosphere for 30 minutes at 40° C., a brown compound was obtained. The product was thereafter dried in a vacuum. The obtained compound was diluted in 400 ml of dichloromethane, washed twice with a saline solution, dried with $Na_2SO_4$ and dried in a vacuum, and a metal salen complex was obtained.

The obtained compound was recrystallized in a solution of diethyl ether and paraffin and measured with high performance liquid chromatography, and obtained was a Mn-salen complex (5.7 g, yield 62%), a Cr-salen complex (5.0 g, yield 54%), and an Fe-salen complex (5.7 g, yield 62%) with a purity of 95% or higher. Meanwhile, the compound 7 (8.2 g, 16 mmol) and triethylamine (22 ml, 160 mmol) were placed in anhydrous methanol (50 ml), and a solution obtained by adding $FeCl_3(.4H_2O)$ (2.7 g, 16 mmol) to 10 ml of methanol in the case of Fe-salen, adding $MnCl_3.4H_2O$ (2.7 g, 16 mmol) in the case of Mn-salen, and adding $CrCl_3.4H_2O$ (2.7 g, 16 mmol) in the case of Cr-salen was mixed under a nitrogen atmosphere.

As a result of mixing the product at room temperature under a nitrogen atmosphere for 1 hour, a brown compound was obtained. The product was thereafter dried in a vacuum. The obtained compound was diluted in 400 ml of dichloromethane, washed twice with a saline solution, dried with $Na_2SO_4$ and dried in a vacuum, and a dimeric metal salen complex compound was obtained.

The obtained compound was recrystallized in a solution of diethyl ether and paraffin and measured with high performance liquid chromatography, and obtained was a dimeric metal salen complex with a purity of 95% or higher. As a result of measurement based on mass spectrometry, the Mn-salen was m/z (El-Mass) M+322.4 (error+1.17 mu) $C_{16}H_{14}MnN_2O_2$ requires m/z 321.23, and the Cr-salen was m/z (El-Mass) M+318.4 (error+0.11 mu) $C_{16}H_{14}CrN_2O_2$ requires m/z 318.29. However, the Co-salen complex was purchased from Tokyo Chemical Industry (TCI product code: S0318, CAS number: 14167-18-1).

Example 2

As a result of measuring the 37° C. (310K) magnetic field-magnetization curve of the Mn-salen complex using MPMS7 manufactured by Quantum Design, paramagnetic properties were observed. The results are shown in FIG. 1.

Example 3

Figure 2:
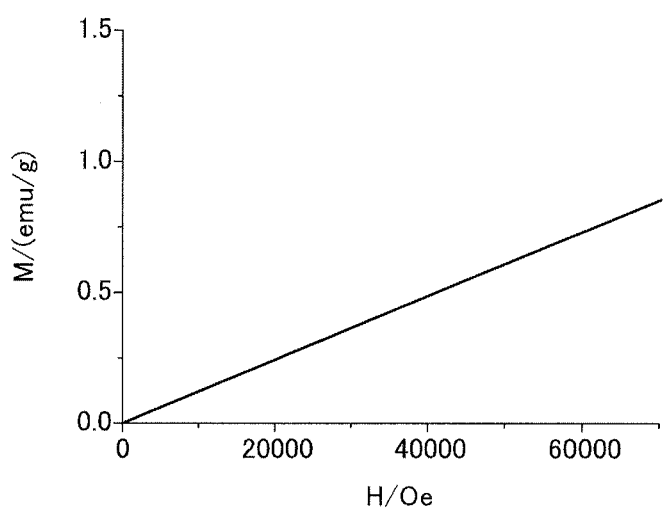
FIG. 2 is a 37° C. (310K) magnetic field-magnetization curve of the Cr-salen complex.

As a result of measuring the 37° C. (310K) magnetic field-magnetization curve of the Cr-salen complex using MPMS7 manufactured by Quantum Design, paramagnetic properties were observed. The results are shown in FIG. 2.

Example 4

Figure 3:
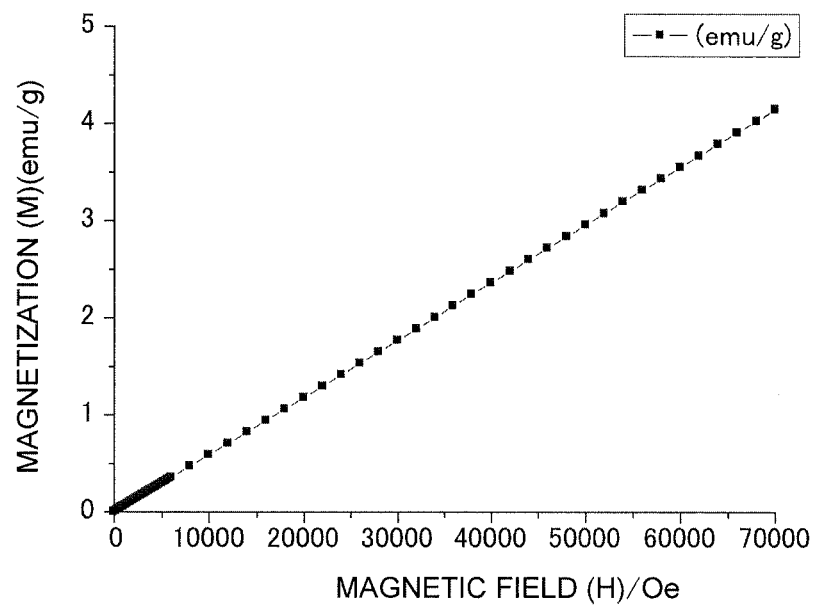
FIG. 3 is a 37° C. (310K) magnetic field-magnetization curve of the Co-salen complex.

As a result of measuring the 37° C. (310K) magnetic field-magnetization curve of the Co-salen complex using MPMS7 manufactured by Quantum Design, paramagnetic properties were observed. The results are shown in FIG. 3.

Example 5

Figure 4:
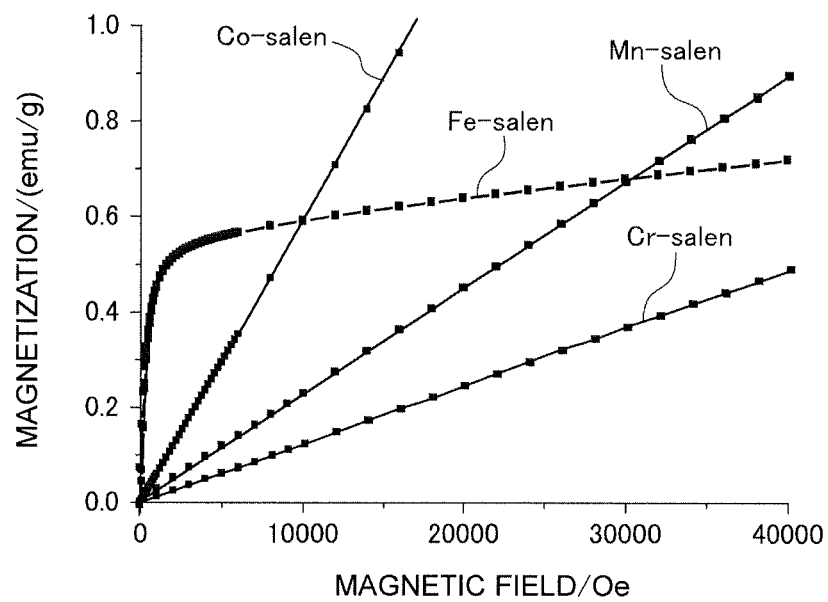
FIG. 4 is a 37° C. (310K) magnetic field-magnetization curve of the Fe-salen complex, the Mn-salen complex, the Cr-salen complex, and the Co-salen complex.

The summary of the results of the 37° C. (310K) magnetic field-magnetization curve of the Fe-salen complex, the Mn-salen complex, the Cr-salen complex, and the Co-salen complex is shown in FIG. 4.

In comparison to the Fe-salen, the Co-salen yields greater magnetization at a magnetic field of 10000 Oe (1T (tesla)) or more. In comparison to the Fe-salen, the Mn-salen yields greater magnetization at a magnetic field of 30000 Oe (3T (tesla)) or more.

Accordingly, the Fe-salen yields the greatest magnetization at a magnetic field of 10000 Oe (1T (tesla)) or less and is suitable for a magnetic field drug delivery system which uses a neodymium permanent magnet or the like. Nevertheless, if the magnetic field is 10000 Oe (1T (tesla)) or more, the magnetization of the Co-salen and Mn-salen complex is the greatest and is optimal for a magnetic field drug delivery system which uses a superconducting magnet.

Example 6

The respective metal salen complex powders of the Fe-salen complex, the Mn-salen complex, the Cr-salen complex, and the Co-salen complex obtained with the foregoing method were sprinkled on a culture medium in an amount that where such powder can be visually confirmed to be drawn to the magnet in a state where the rat L6 cells are confluent at 30%, and a photograph of the state of the culture medium after 48 hours was taken.

Figure 5:
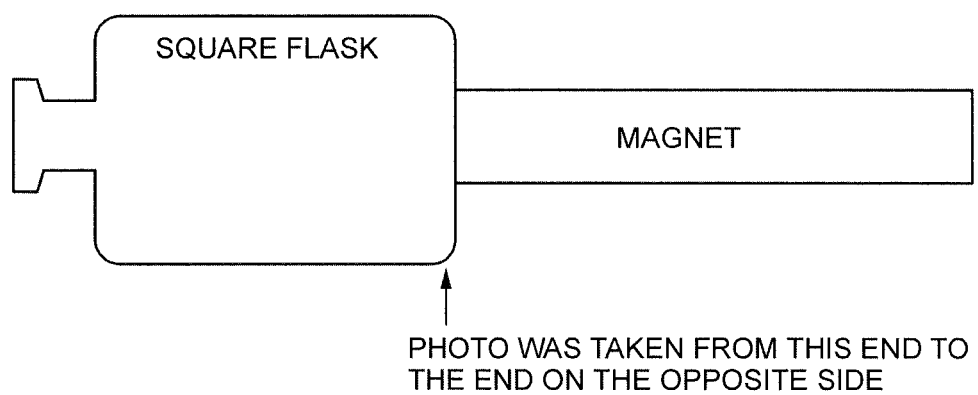
FIG. 5 is a side view showing the outline of a state of causing a bar magnet to come in contact with a square flask as the culture medium of the rat L6 cells.

FIG. 5 shows a state where the bar magnet was caused to come in contact with a square flask as the culture medium of the rat L6 cells. Subsequently, a photograph was taken from one end to the other end of the bottom face of the square flask after 48 hours, and the results of calculating the number of cells are shown in FIG. 6.

Figure 6:
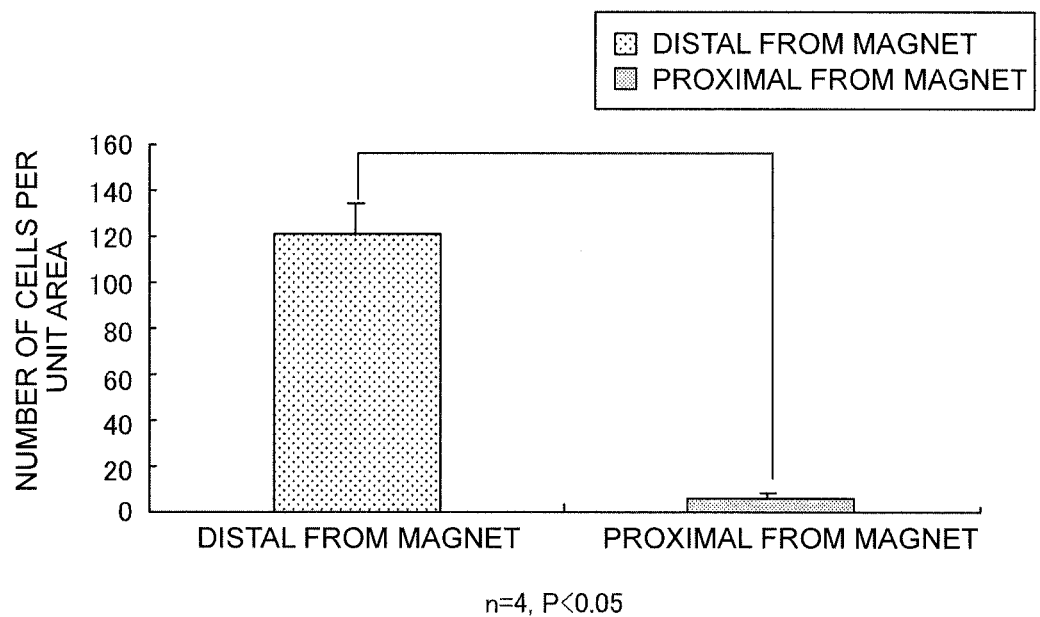
FIG. 6 is a characteristic diagram showing the results of taking a photograph from one end to the other end of the bottom face of the square flask after 48 hours and calculating the number of cells.

In FIG. 6, proximal from the magnet shows the inside of the projected area of the magnet end face in the bottom face of the square flask, and distal from the magnet shows the area that is on the side that is opposite to the magnet end face in the bottom face of the square flask. As shown in FIG. 6, at the proximal from the magnet, the Mn-salen complex is gravitated and increases the concentration of the iron complex, and it is evident that the number of cells is extremely lower than the distal based on the DNA inhibition effect of the iron complex. Consequently, the drug can be concentrated at the diseased site or tissues as the individual target based on the system of the present invention comprising the drug with magnetic properties and a magnetism generating means.

Figure 7:
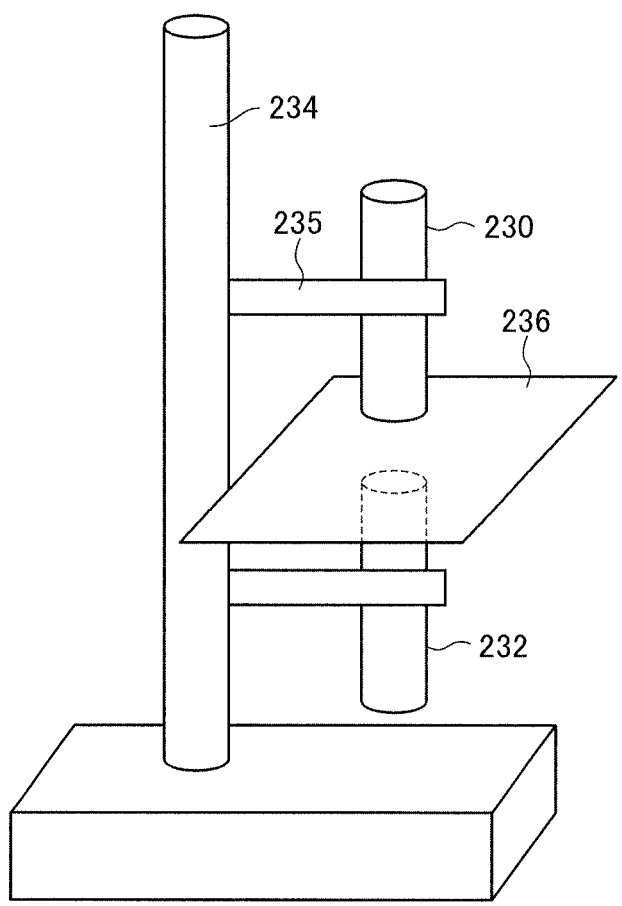
FIG. 7 is a perspective view showing the outline of a magnetic delivery device.

A delivery example using the delivery device is now explained. With this delivery device, as shown in FIG. 7, a pair of magnets 230, 232 facing each other in the direction of gravitational force are supported by a stand 234 and a clamp 235, and a metal plate 236 is disposed between the magnets. By placing a metal plate, specifically an iron plate between the pair of magnets, it is possible to create a strong magnetic field that is uniform locally. This delivery device can cause the generated magnetic force to be variable by using electromagnets in substitute for the magnets. Moreover, by enabling a pair of magnetic force generating means to move in the XYZ direction, the magnetic force generating means can be moved to the location as the solid target on a table.

By placing a solid tissue on the area of this magnetic field, the drug can be concentrated of that tissue. The foregoing metal complex (drug concentration 5 mg/ml (15 mM)) was administered intravenously to a mouse weighing approximately 30 grams and laparotomy was performed, and the mouse was placed on the iron plate so that its right kidney is positioned between the pair of magnets.

The magnets that were used were manufactured by Shin-Etsu Chemical Co., Ltd., and the product number is N50 (neodymium-based permanent magnet) and the residual magnetic flux density is 1.39 to 1.44 T. Here, the magnetic field that was applied to the right kidney was approximately 0.3 (T) and the magnetic field that was applied to the left kidney was approximately ⅒ thereof.

Together with the left kidney and the kidney (control) to which the magnetic field is not applied, a magnetic field was added to the right kidney of the mouse and SNR was measured with MRI 10 minutes later with the T1 mode and the T2 mode.

Figure 8:
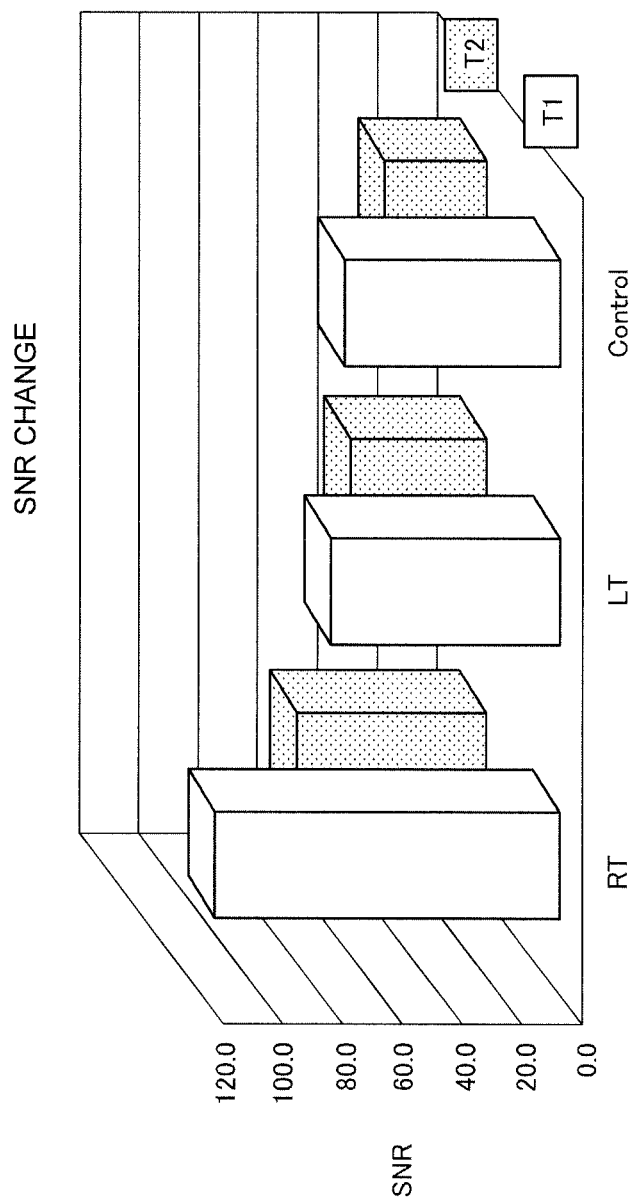
FIG. 8 is a graph of the MRI measurement results (T1 enhanced signal) of the kidney of a mouse.

Consequently, as shown in FIG. 8, it was confirmed that the right kidney (RT) to which the magnetic field was applied was able to retain the drug within the tissue in comparison to the left kidney (LT) and the control.

Figure 9:
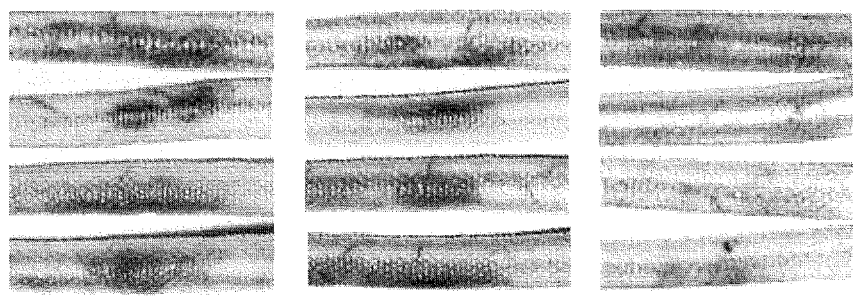
FIG. 9 is a photograph showing the effect of the salen complex relative to the melanoma growth in the mouse.

FIG. 9 shows the effect of the salen complex relative to the melanoma growth in the mouse. The melanoma was formed in vivo in the mouse tail tendon by locally transplanting the cultured melanoma cells (clone M3 melanoma cells).

The salen complex was administered parenternally from the vein of the tail tendon (50 mg/kg), and a commercially available bar magnet (630 mT, cylindrical neodymium magnet with a length of 150 mm and diameter of 20 mm) was used to locally apply a magnetic field. The application of the bar magnet was performed by causing it to come in mild contact with the melanoma site for 3 hours immediately after the salen complex was injected for 10 to 14 days.

The bar magnet was applied for a two-week growth period to the mouse tail tendon of 150 mm or less so that the magnetic field intensity becomes the maximum intensity at the site where melanoma extension is anticipated. Twelve days after the initial injection of the salen complex, the melanoma extension was evaluated by evaluating the melanoma stained site.

Figure 10:
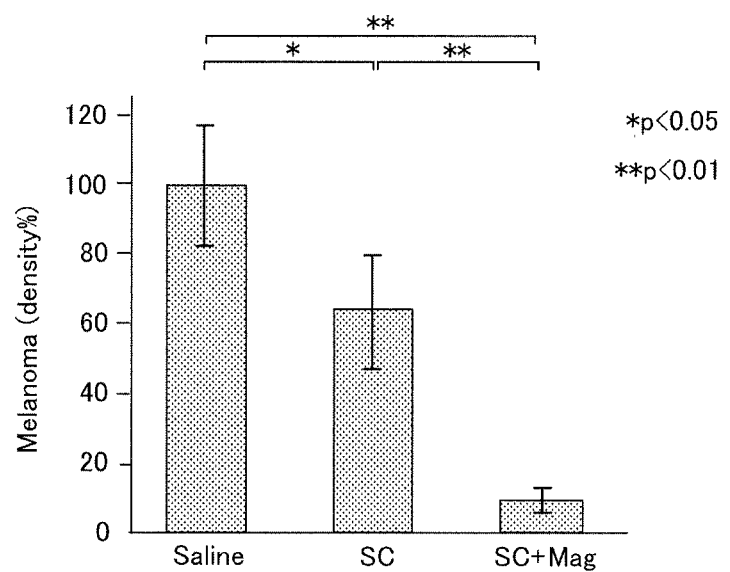
FIG. 10 is a graph showing the effect of melanoma expansion.

As shown in FIG. 10, the melanoma expansion was the greatest (100±17.2%) with a saline water group (saline) in which saline water was injected in substitute for the salen complex.

Meanwhile, the melanoma expansion gradually decreased with the SC group in which the salen complex was injected without applying the magnetic field (63.68±16.3%). Meanwhile, with the SC+Mag group in which the salen complex was injected while applying the magnetic field (n=7 to 10), most of the melanoma had disappeared (9.05±3.42%).

Figure 11:
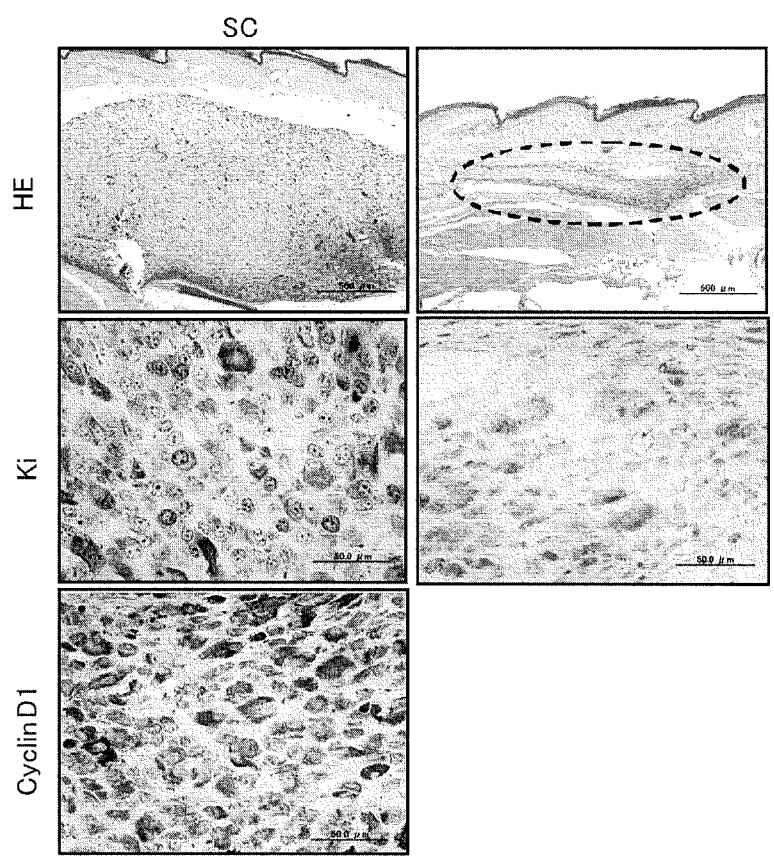
FIG. 11 shows the results of the histological experiment.

As shown in FIG. 11, a histological experiment was conducted by using an anti-Ki-67 antibody and anti-Cyclin D1 antibody as a tumor growth marker of the tissue portion based on the hematoxylin-eosin stain and the immune tissue stain. Consequently, the tumor expansion of the melanoma decreased in the case (SC) of injecting the salen complex, and it was discovered that the tumor expansion of the melanoma mostly disappeared when combined with the application of the magnetic field to the salen complex.

Figure 12:
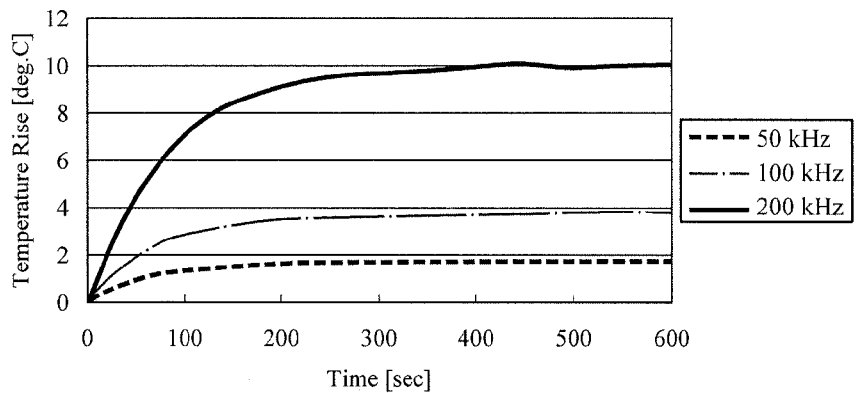
FIG. 12 is a graph showing the temperature rise when an alternating magnetic field is applied to a drug.
Figure 12:
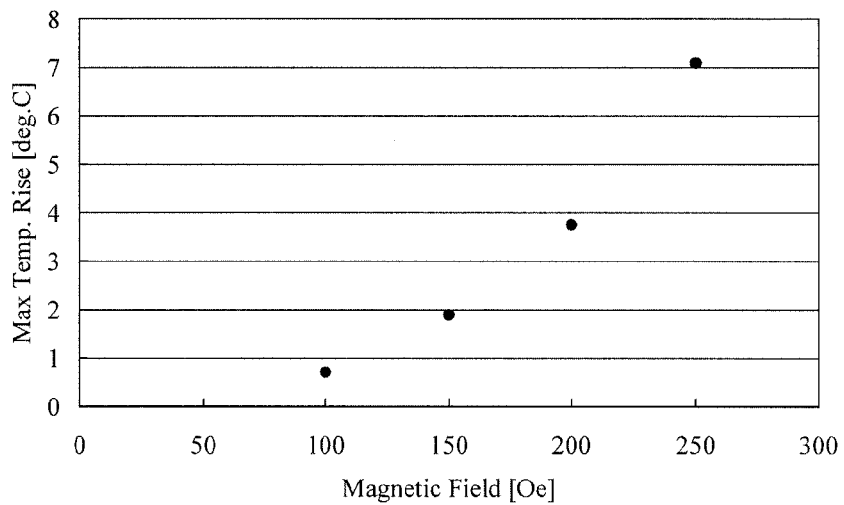
Figure 12:
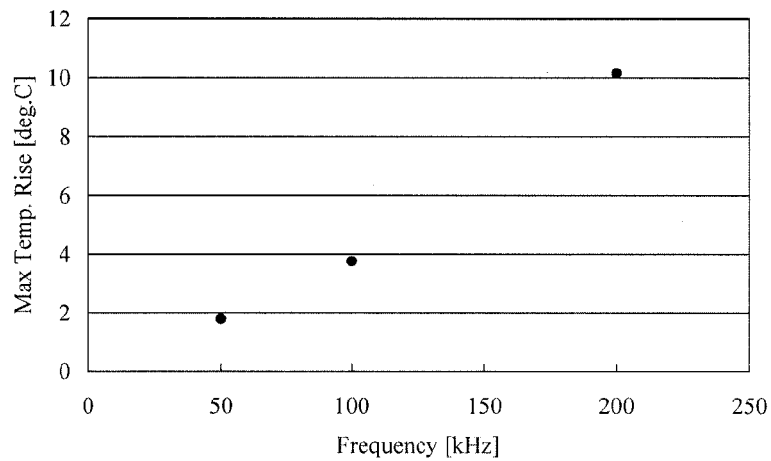

Moreover, when an alternating magnetic field with a magnetic field intensity of 200 Oe (oersted) and a frequency of 50 kHz to 200 KHz was applied to the drug, the temperature of the drug rose from 2° C. to 10° C. (FIG. 12). When converting this to the temperature during internal administration, the temperature corresponds to 39° C. to 47° C., and it was confirmed that this is a temperature range capable of killing and wounding the cancer cells.

Example 7

Figure 13:
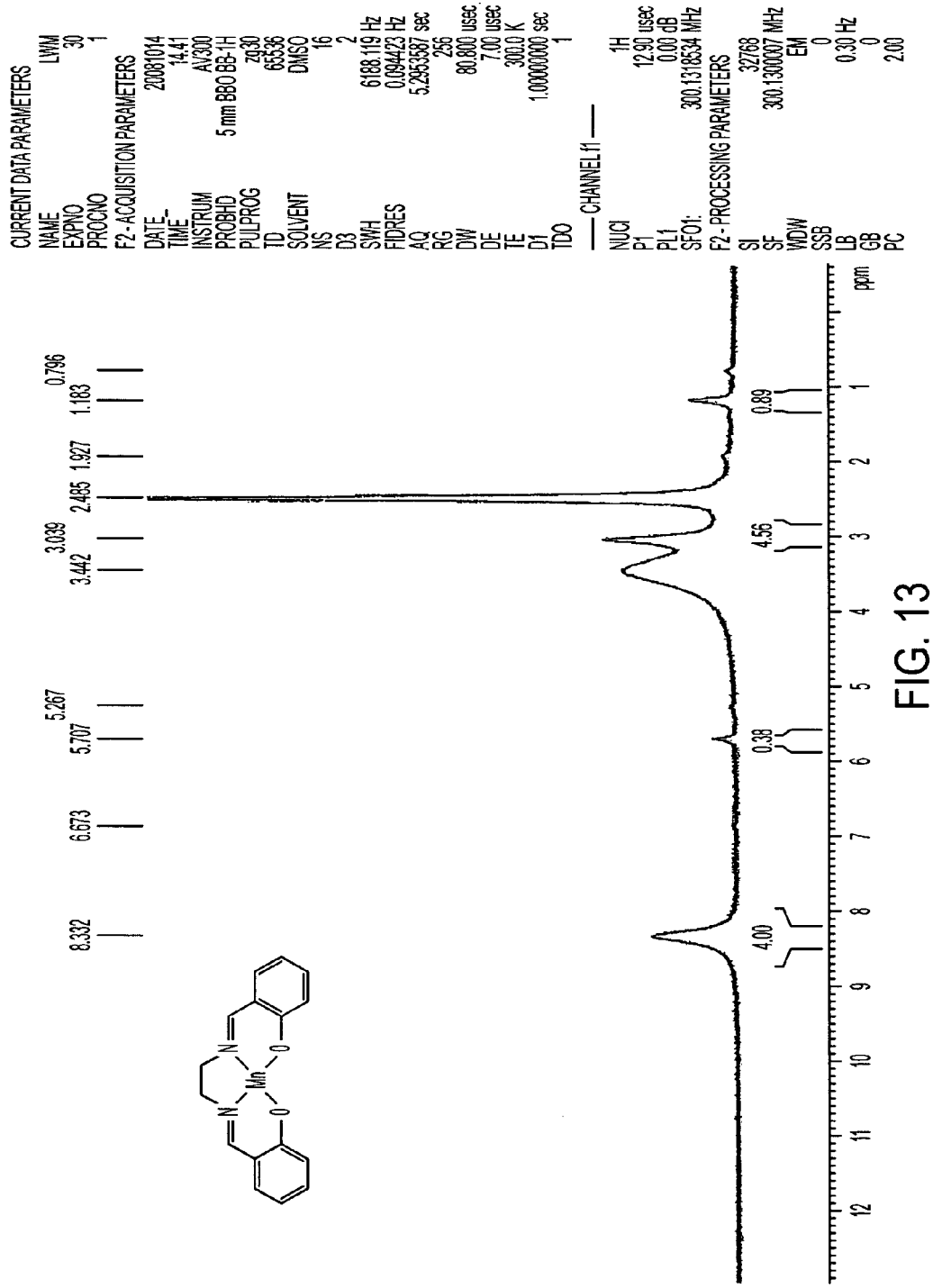
FIG. 13 is a graph showing the NMR peak of the Mn-salen.
Figure 14:
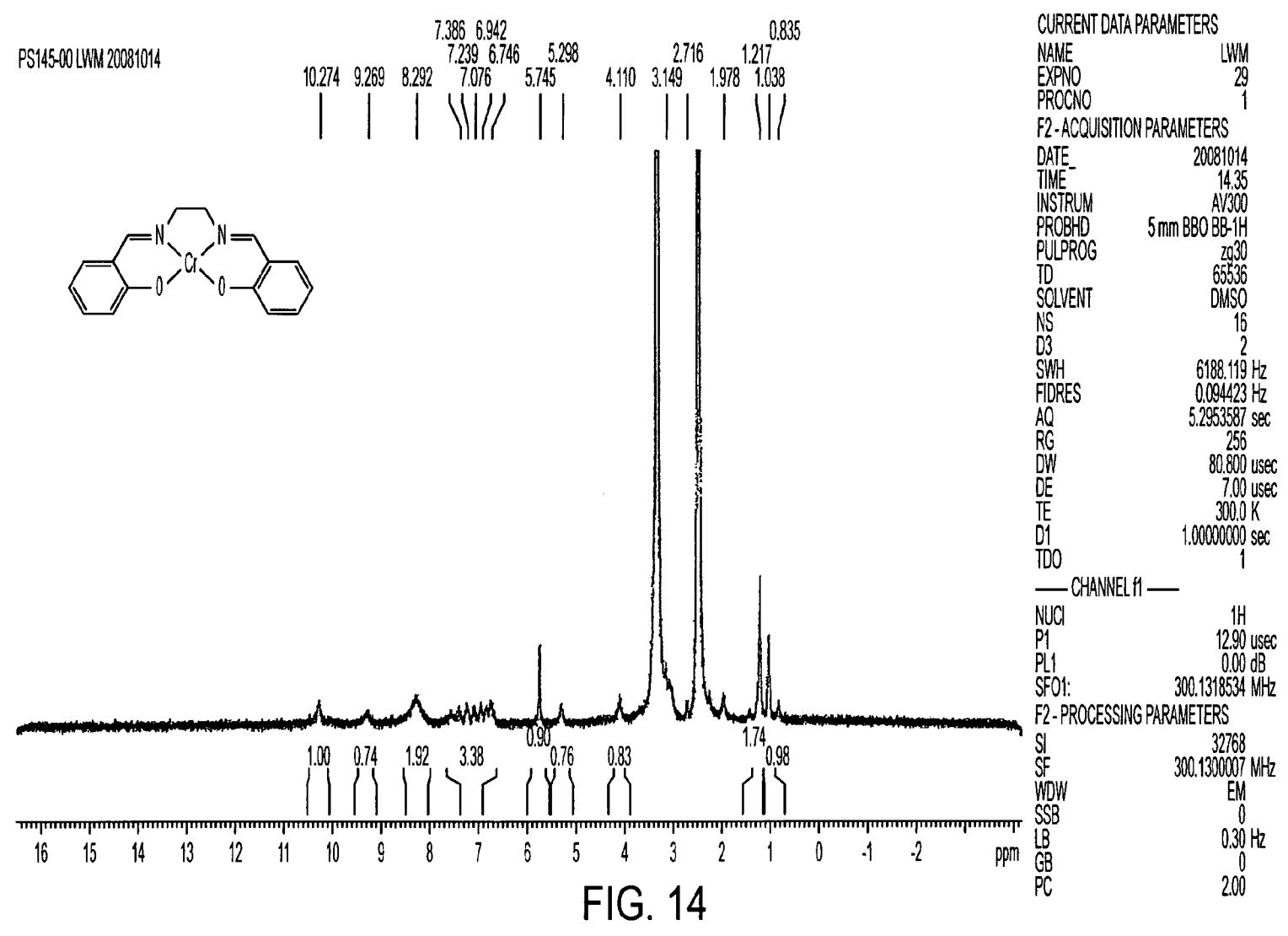
Figure 15:
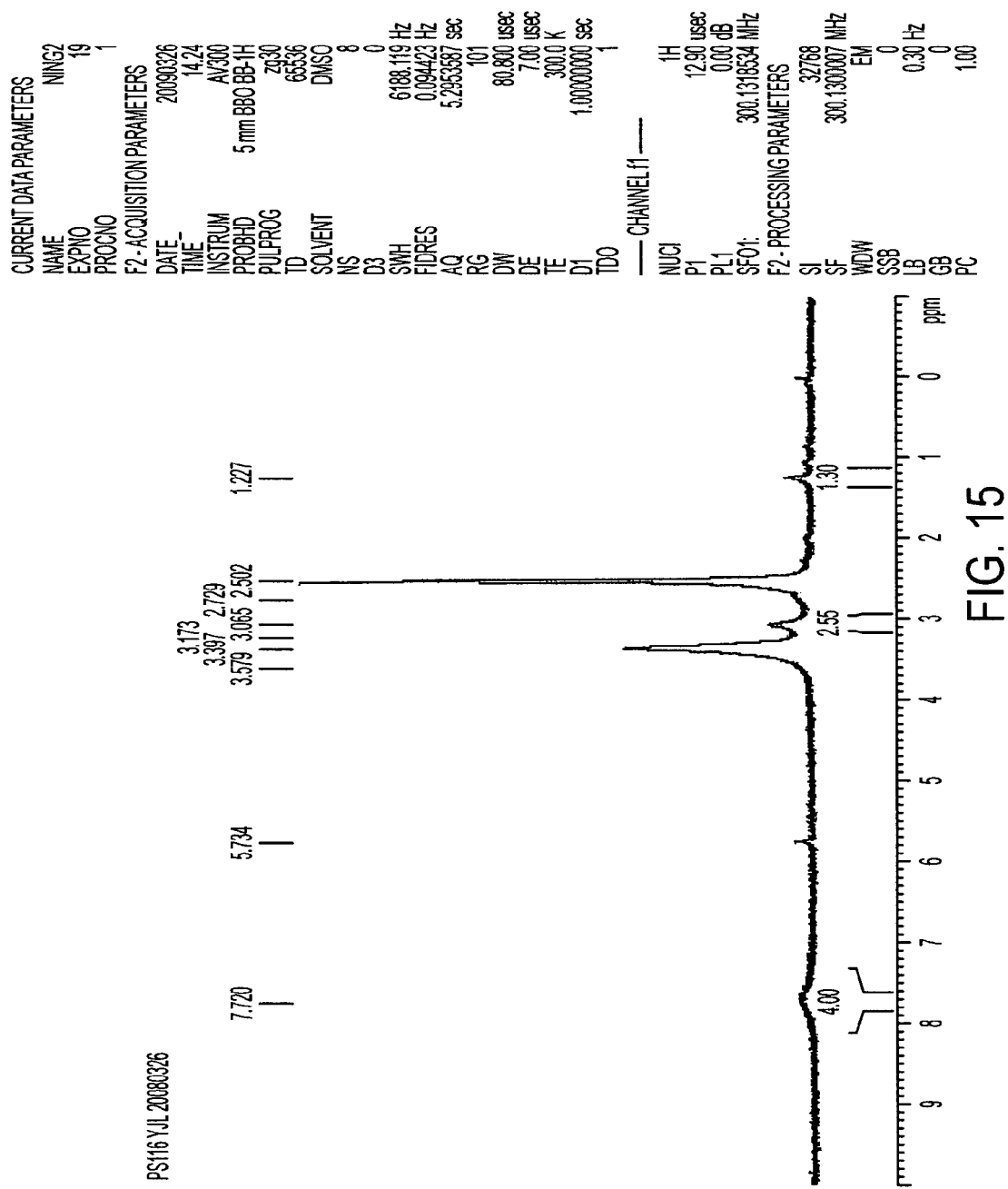
FIG. 15 is a graph showing the NMR peak of the Fe-salen.
Figure 16:
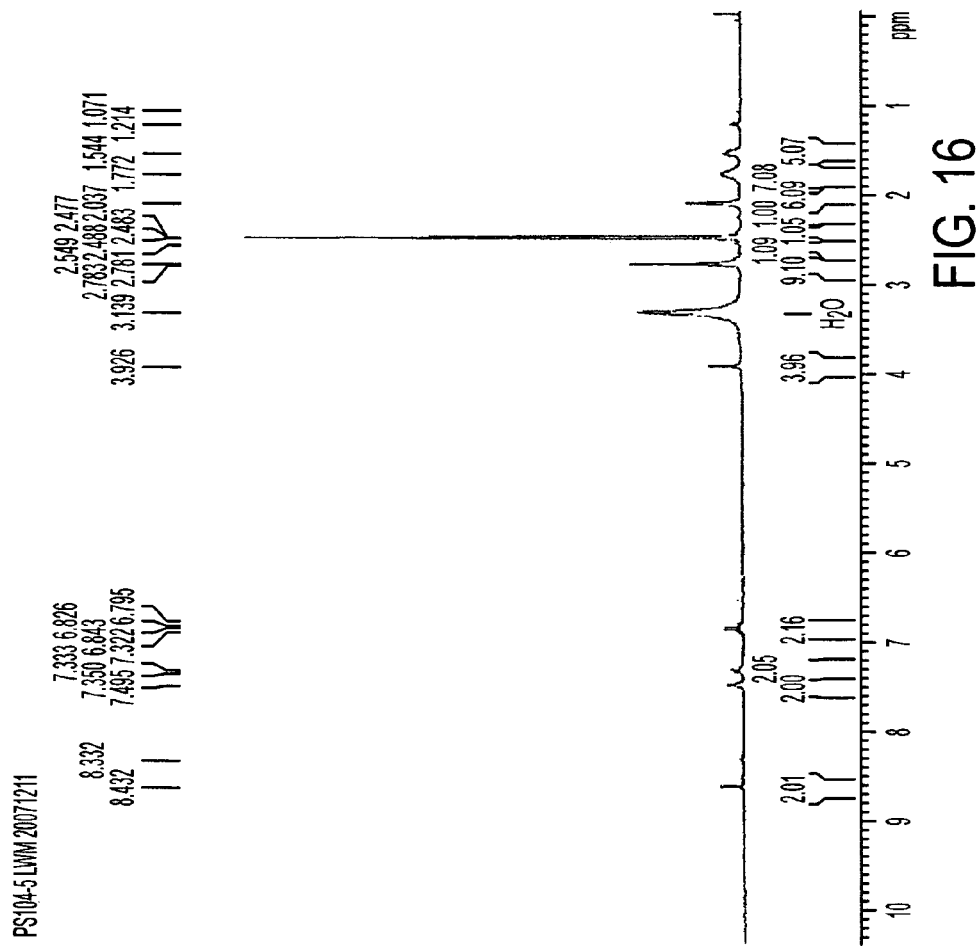
FIG. 16 is a graph showing the peak of the salen ligand.

FIG. 13 shows the NMR peak of the Mn-salen, FIG. 14 shows the NMR peak of the Cr-salen, FIG. 15 shows the peak of the Fe-salen, and FIG. 16 shows the peak of the salen ligand. Since the Mn-salen, the Cr-salen, and the Fe-salen are magnetic substances, the nuclear spin signal that is detected with NMR resonated with the signal of the electron spin that emerged for the magnetic substance, and the peak became broad.

For example, the Mn-salen as a magnetic substance shows a peak of 2 ppm or more at the 3.442 ppm, 3.039 ppm, 2.405 ppm, the Cr-salen shows a peak of 2 ppm or more at 2.716 ppm, 3.149 ppm, and the Fe-salen shows a peak of 2 ppm or more at 2.502 ppm, 3.347 ppm. Meanwhile, the salen ligand which is not a magnetic substance has no peak with a width of 2 ppm or more.

Example 8

(1) Synthesis of Fe-Salen+Paclitaxel (Taxol)

The outline of the synthesis is as follows.

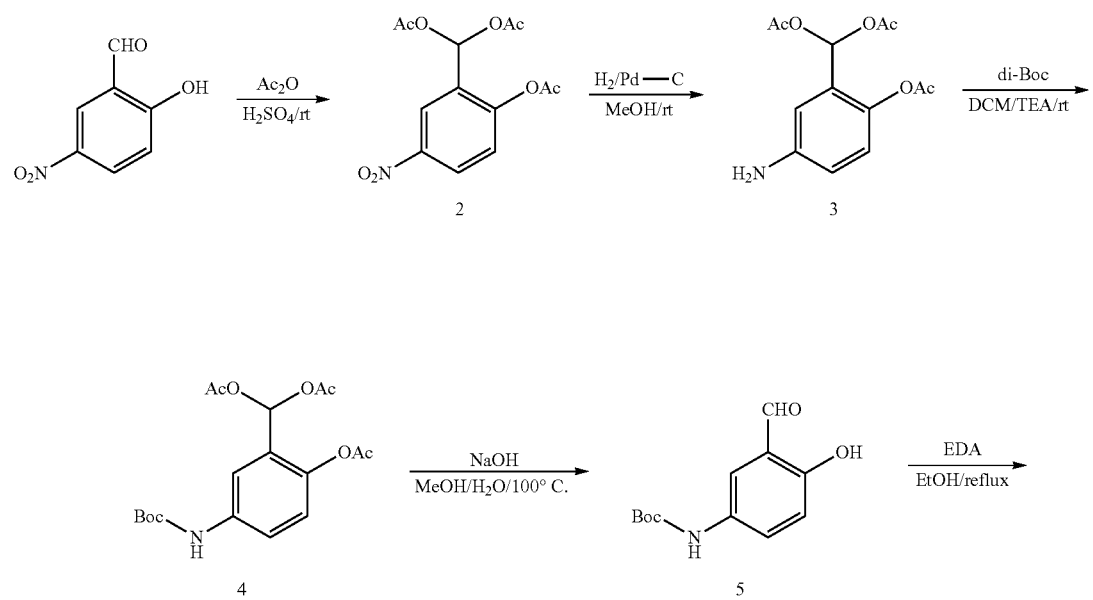

-continued
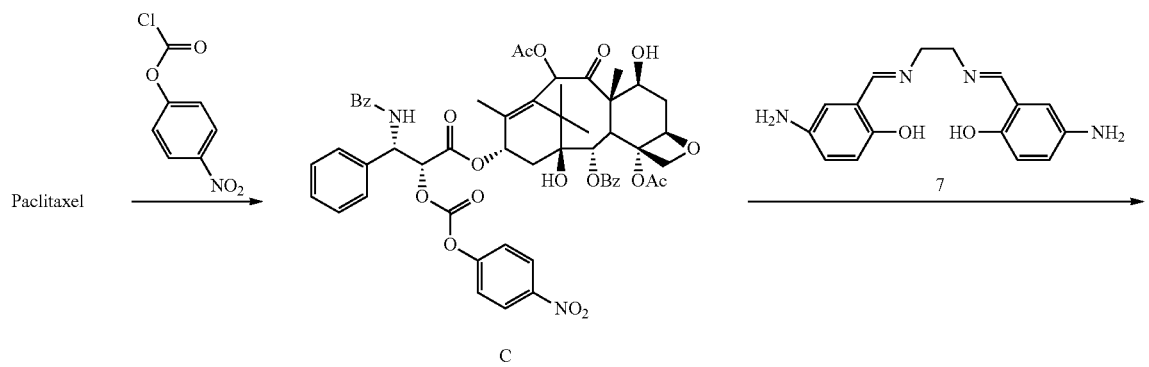
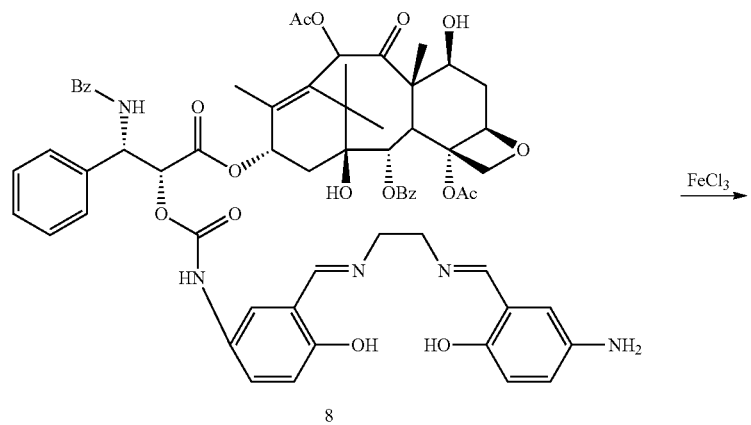
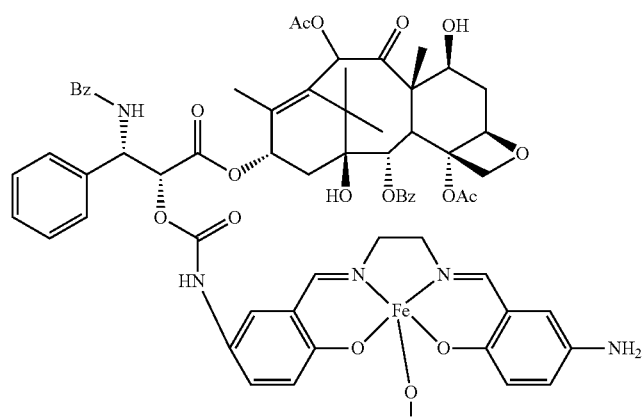

-continued

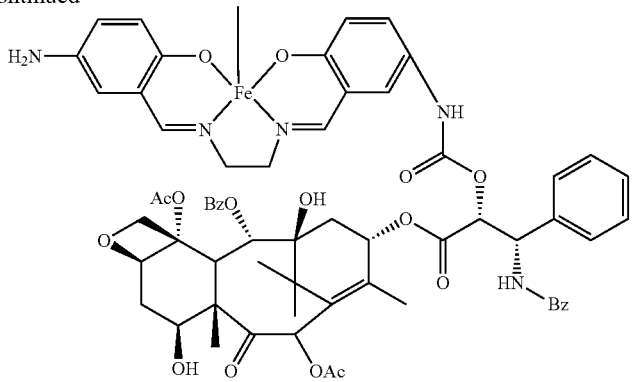

HHPS-133

Step 1

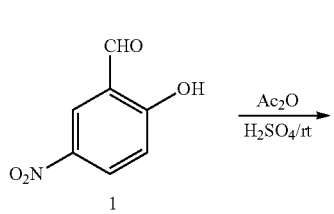 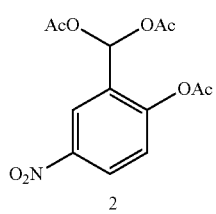

A compound 1, acetic anhydride, and H₂SO₄ were mixed for 1 hour at room temperature. The reaction during the mixing was confirmed with a TLC (Thin-Layer Chromatography). After confirming the details and performing recrystallization with ethyl acetate (EtOAc)/phosphatidyl ethanol amine (P.E.), a compound 2 was obtained. The compound 2 was confirmed by measuring the molecular weight with a mass spectrometry.

Step 2

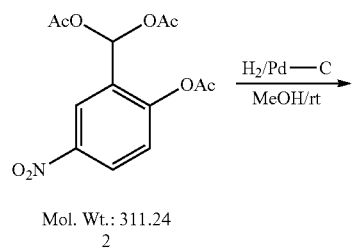 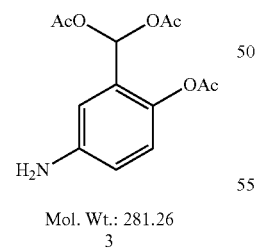

Mol. Wt.: 311.24
2

Mol. Wt.: 281.26
3

The compound 2 and carbon containing 10% of palladium were subject to hydrogenation treatment for 2 hours in methanol (MeOH) under a hydrogen atmosphere. As a result of filtering the obtained compound, a compound 3 was obtained. The compound 3 was confirmed by measuring the molecular weight with a mass spectrometry.

Step 3, 4

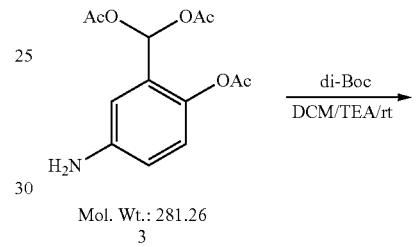

Mol. Wt.: 281.26
3

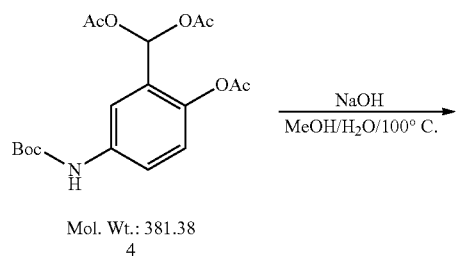

Mol. Wt.: 381.38
4

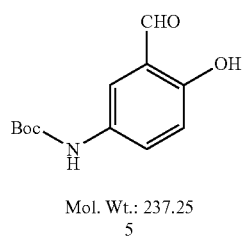

Mol. Wt.: 237.25
5

The compound 3 and di(tert-butyl) dicarbonate were formed into a solution in dichloromethane (DCM), and agitated overnight. After evaporating and reacting the solvent in a vacuum, and adhered oil was removed with methanol, NaOH aqueous solution was added, and the obtained solution was refluxed for 5 hours. After confirming the details, the raw material was refined based on flash chromatography using silica gel to obtain the compound 5.

Step 5

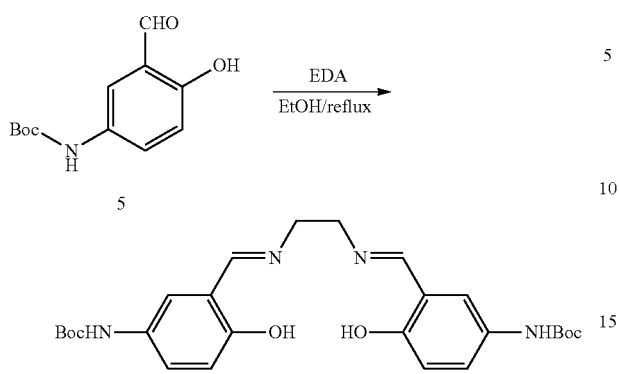

The solution of the compound 5 was created with EtOH, refluxed, and several drops of ethylenediamine was added in a warm bath. After adding ethylenediamine, the product was refluxed and mixed for 0.5 hours. As a result of filtering the product, a compound 6 as a ligand with a thin, yellow spiculate Shiff group was obtained.

Step 6

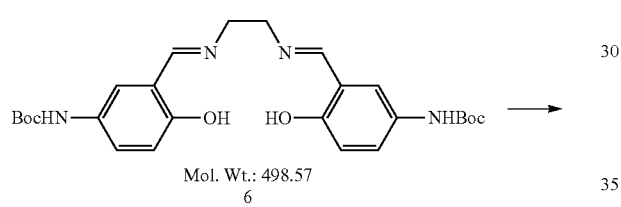

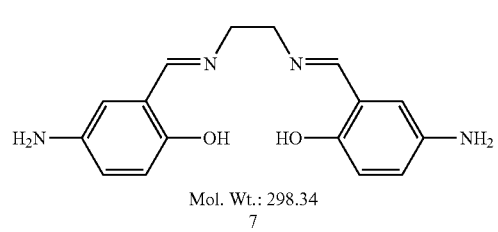

In order to create a solution of the compound 6 with dichloromethane (DCM), a solution obtained by placing hydrochloric acid to ether was added. The solution was agitated for 5 hours at room temperature, and filtered and washed with DCM and ether to obtain a compound 7. The compound 7 was confirmed with $^1$HNMR.

Step 7

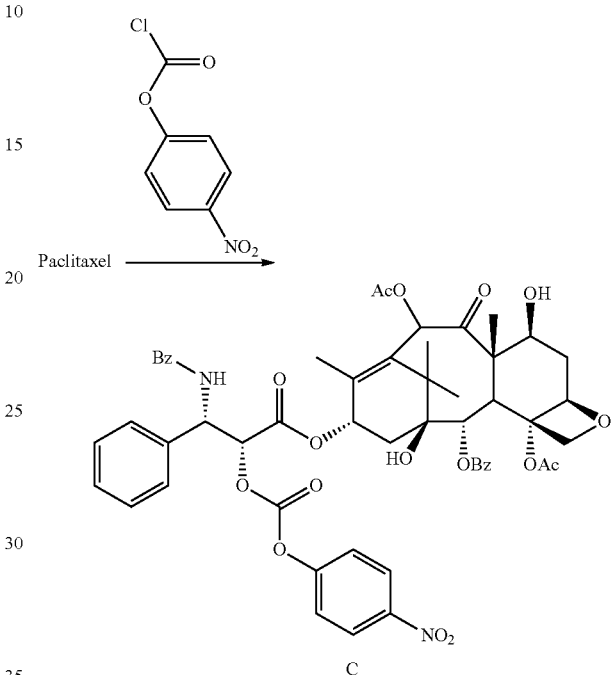

Several drops of chloroformic acid 4-nitrophenyl dissolved in DCM was added to Paclitaxel dissolved in DCM. The solution was agitated for 3 hours at −50° C. After the reaction, the solvent was vaporized. As a result of refining the obtained solid matter with flash chromatography using silica gel, a compound C was obtained with a yield of 68%. This compound was confirmed with mass spectrometry.

Step 8, 9

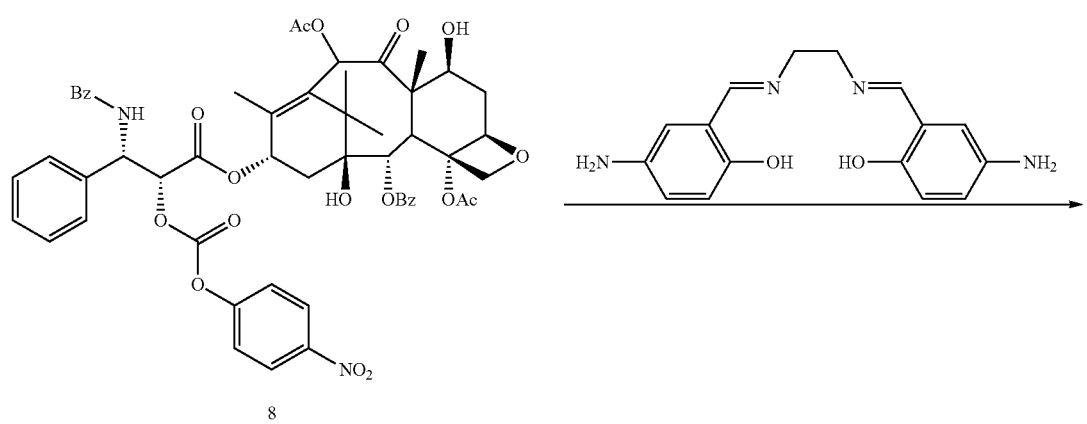

-continued
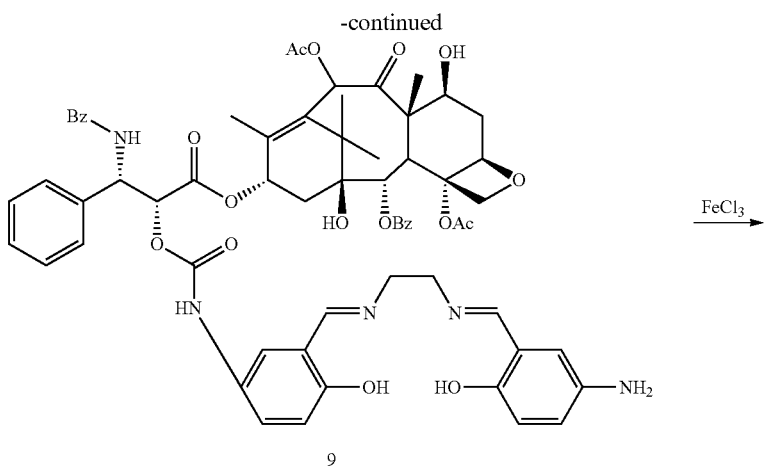
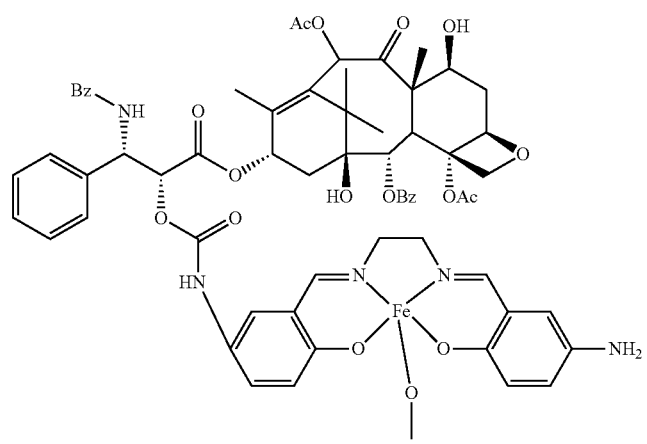
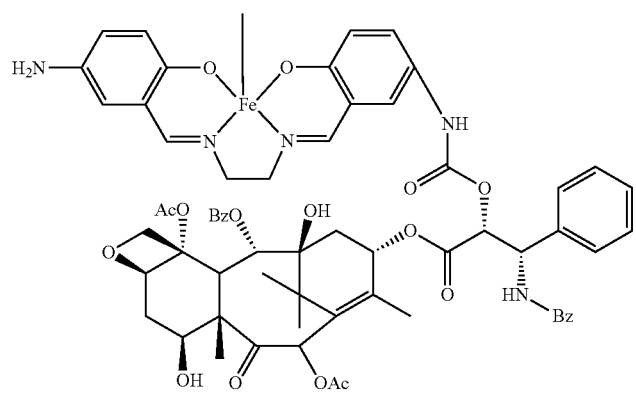

The compound 7 was added to a solution obtained by adding the compound 8 and K₂CO₃ to DMF (N, N-dimethylformamide). The mixed solution was agitated for 3 hours at −20° C., and the reacted solution was thereafter filter and concentrated. The obtained raw material was dissolved in methanol and FeCl₃ was added thereto. After the addition of FeCl₃, the obtained mixed solution was agitated once again for 30 minutes.

Figure 17:
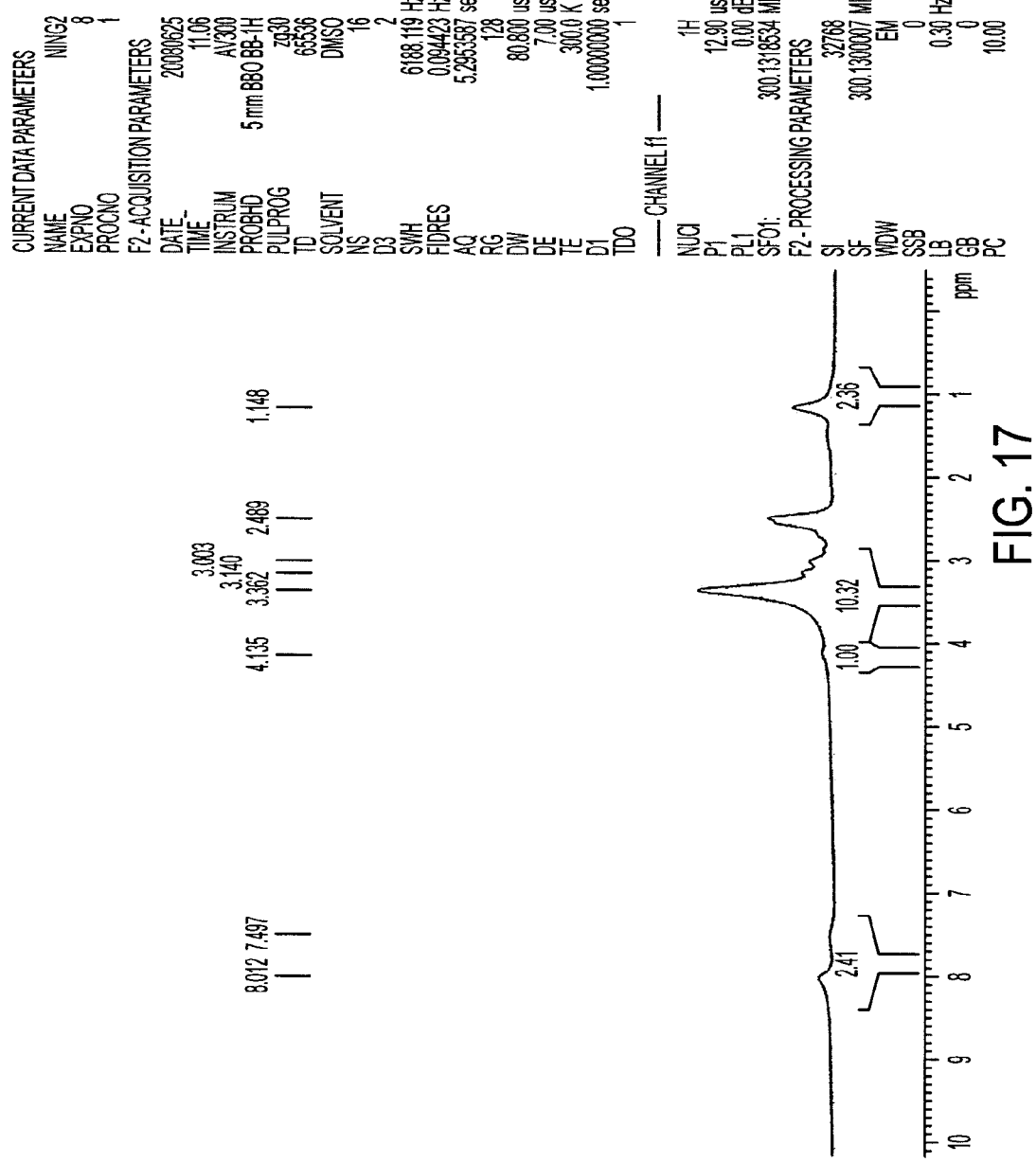
FIG. 17 is a graph showing the NMR measurement results of the compound in which Paclitaxel (Taxol) is bound with the Fe-salen.
Figure 18:
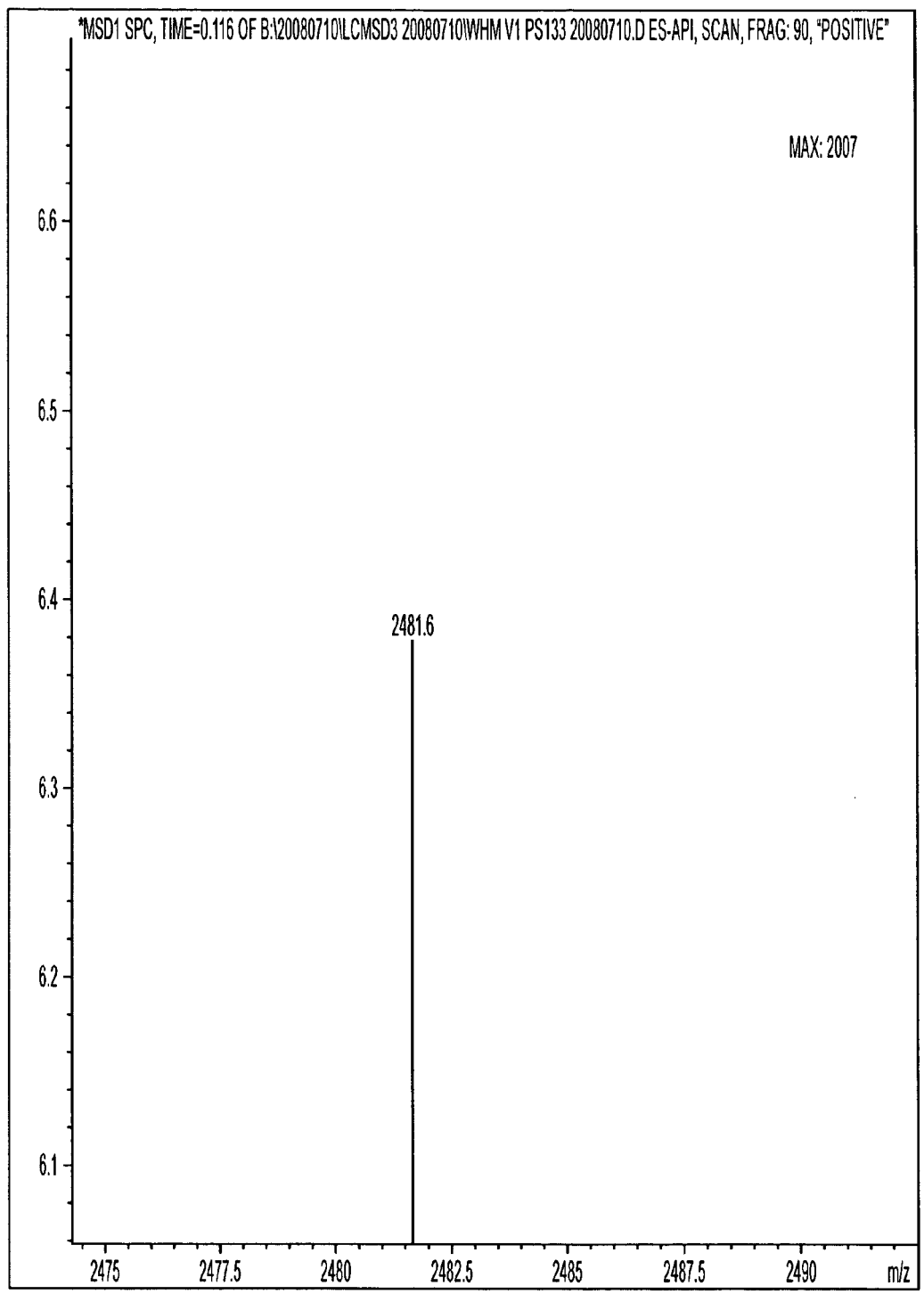
FIG. 18 is the mass spectrometry results of the foregoing compound.

The obtained solvent vaporized in a vacuum and a solid raw material was thereby obtained. The obtained solid raw material was recrystallized using a mixed solution of methanol and diethyl ether, whereby brown solid matter was obtained. Based on measurement with mass spectrometry, it was confirmed that it was the target compound. FIG. 17 shows the NMR measurement results. In addition, the mass spectrometry results are shown in FIG. 18.

Example 9

Synthesis of Compound in which Lipid-Lowering Agent (Gemfibrozil) was Bound to Dimeric Fe-Salen Complex

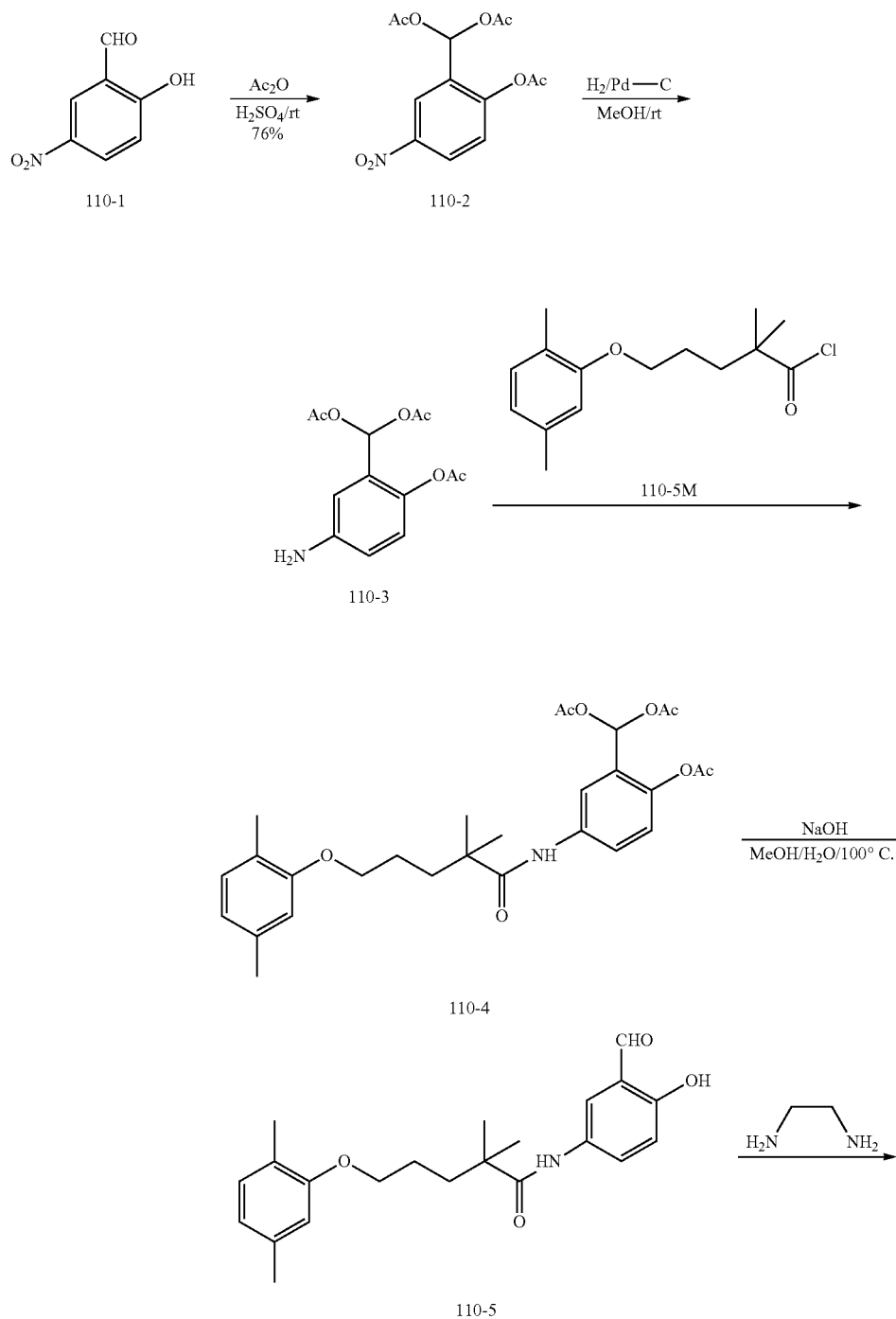

-continued
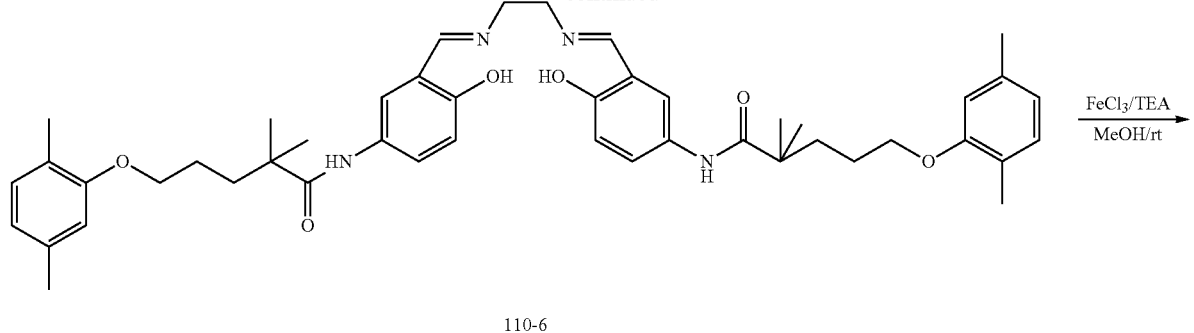
110-6
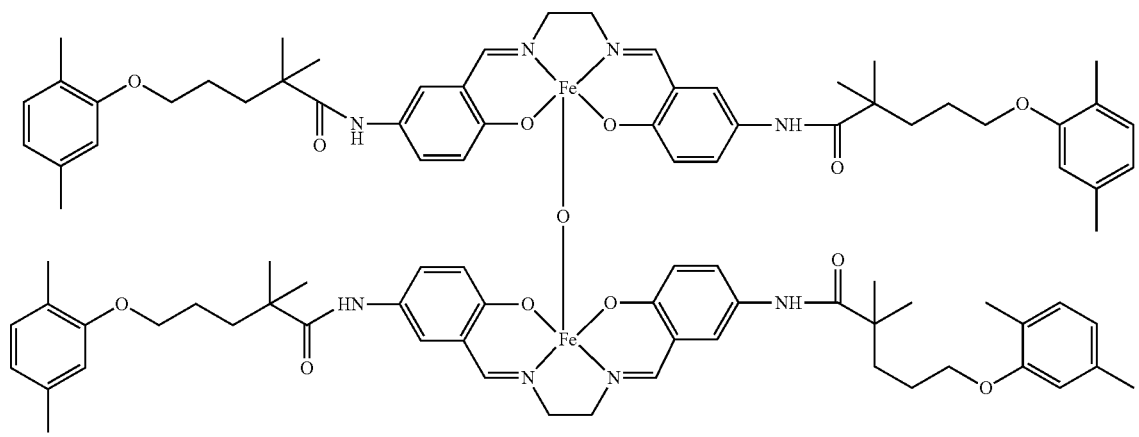
HHPS-110
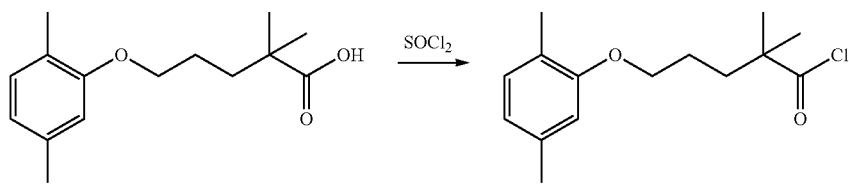
Step 1 to Step 4 of the synthesis process are the same as Example 8, and the reaction of Step 6 below was subsequently performed.
Step 6:
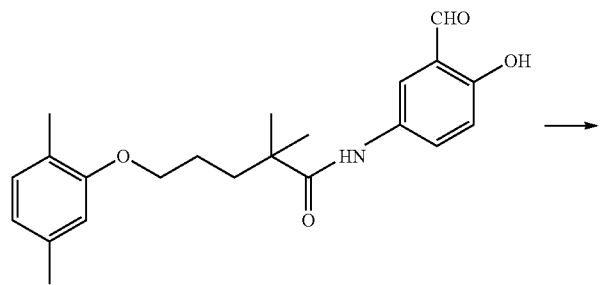
110-5

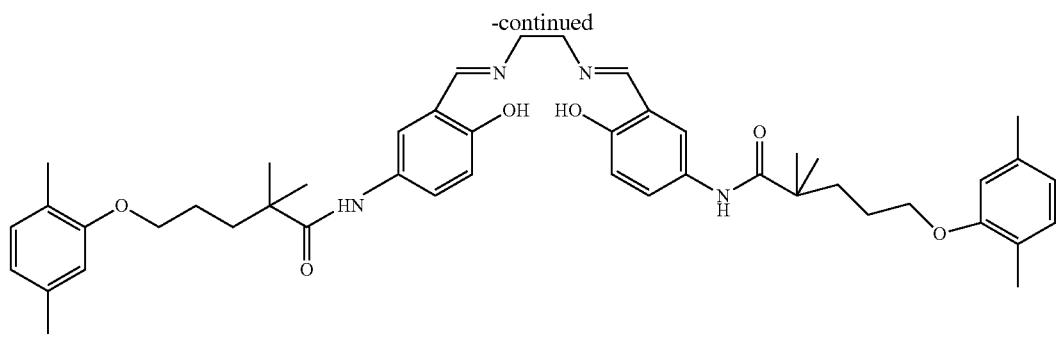

110-6

The compound 110-5 was dissolved in ethyl alcohol (EtOH) and refluxed while being heated, and several drops of a solution of ethylenediamine was added during the reflux. After the foregoing addition, the mixture was once again refluxed and agitated for 0.5 hours. Subsequently, the obtained precipitate was filtered with a filter and collected, whereby a compound 110-6 as a ligand with a thin, yellow spiculate crystal-shaped Shiff group was obtained.

Step 7.

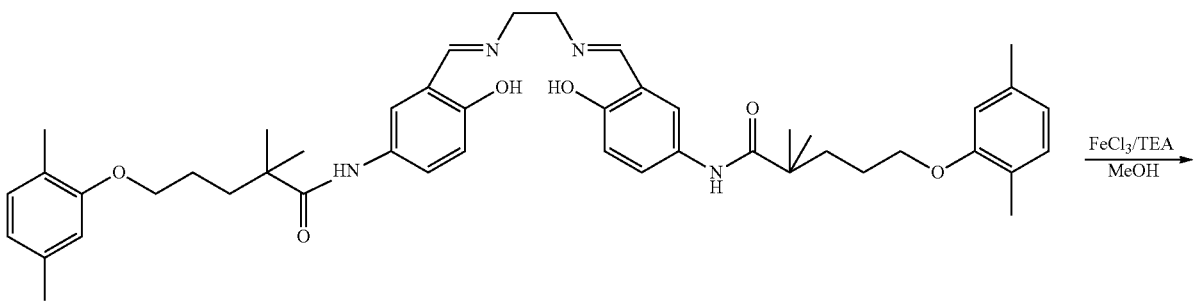

110-6

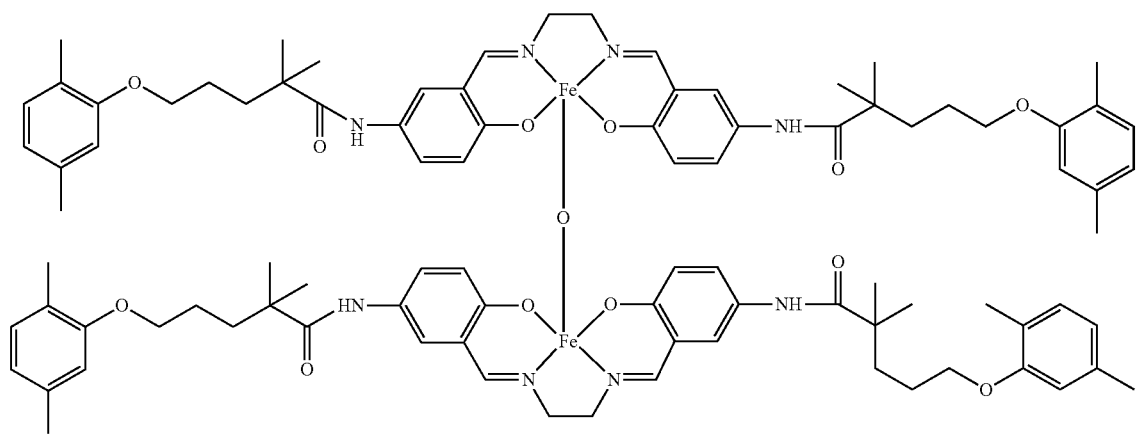

HHPS-110

Figure 19:
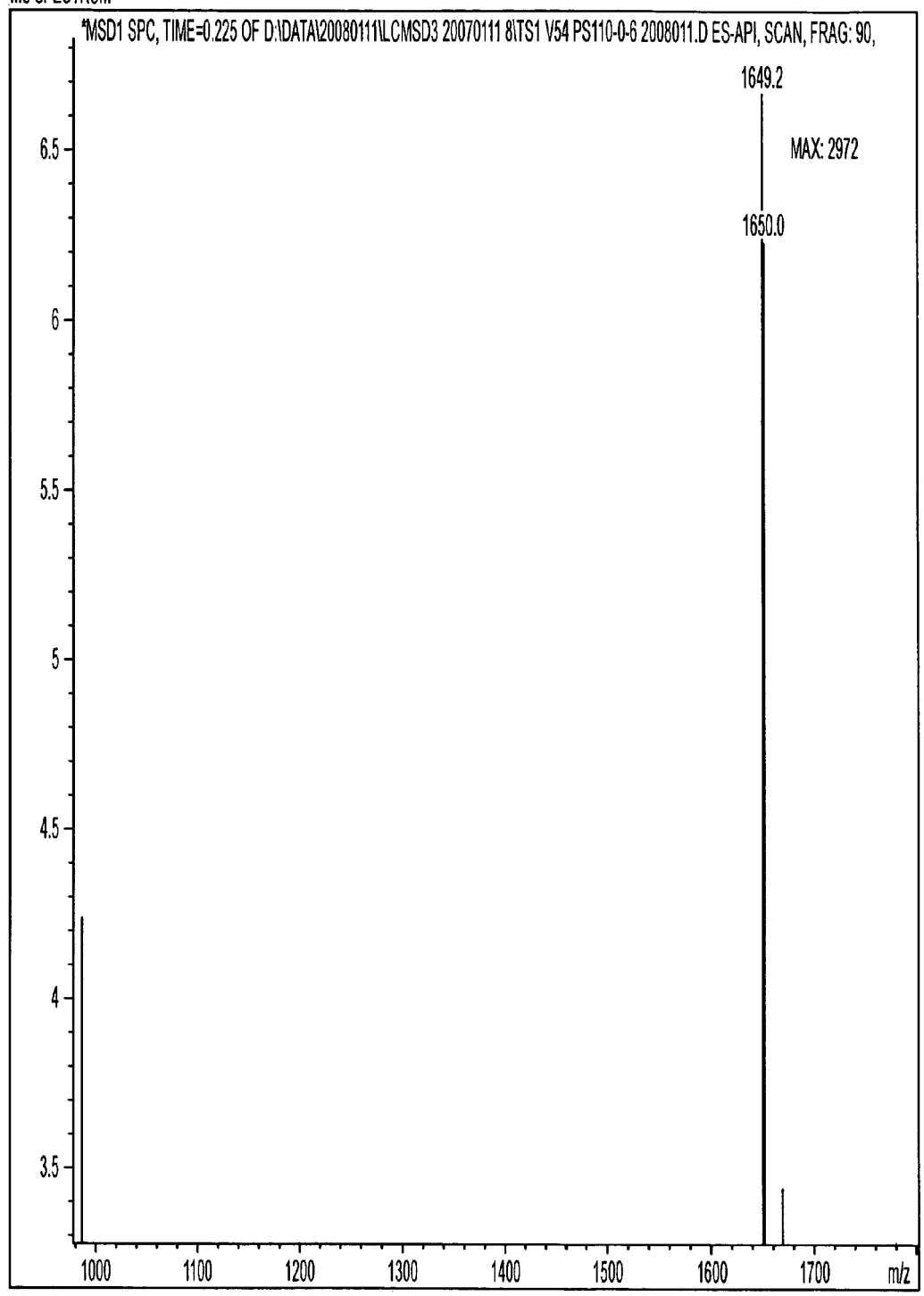
FIG. 19 is a graph showing the NMR measurement results of the compound in which a lipid-lowering agent (Gemfibrozil) is bound with the dimeric Fe-salen complex.

FeCl₃ dissolved in triethylamine (TEA) was added to the product (110-6) dissolved in methanol. After the foregoing addition, the obtained mixture was further agitated for 30 minutes. The solvent was vaporized in a vacuum to obtain the product. The obtained product was recrystallized with methanol and diethyl ether, whereby 1 gram of a brown target compound was obtained. The target compound was confirmed as having a molecular weight of 1649 with mass spectrometry (LC-MS). FIG. 19 shows the results thereof.

Example 10

Synthesis of Compound in which a Lipid-Lowering Agent (Gemfibrozil) was Bound with an Fe-Salen Complex

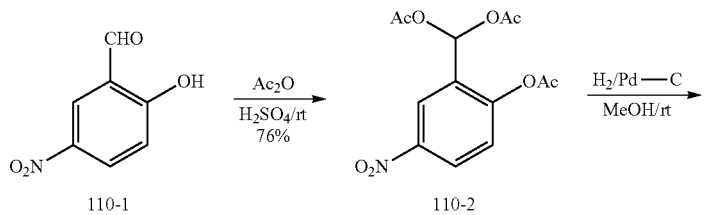

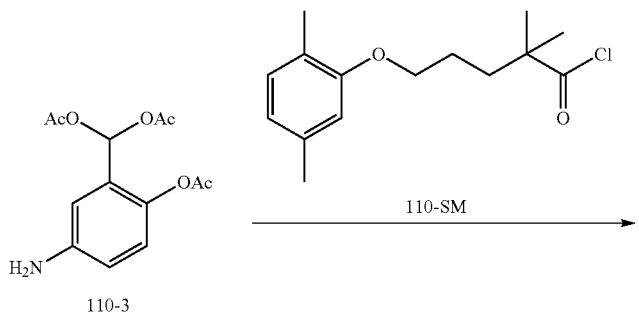

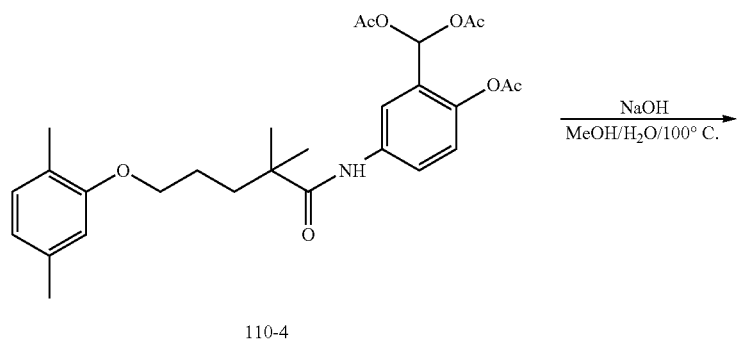

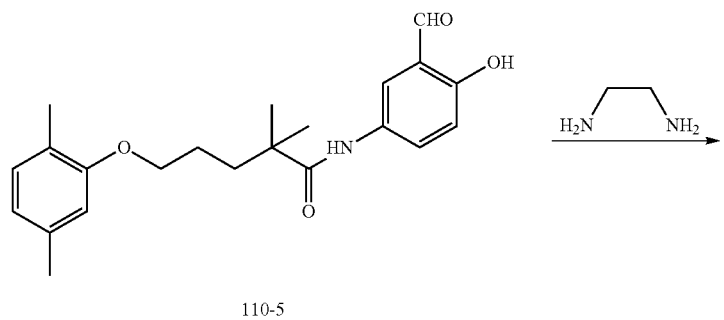

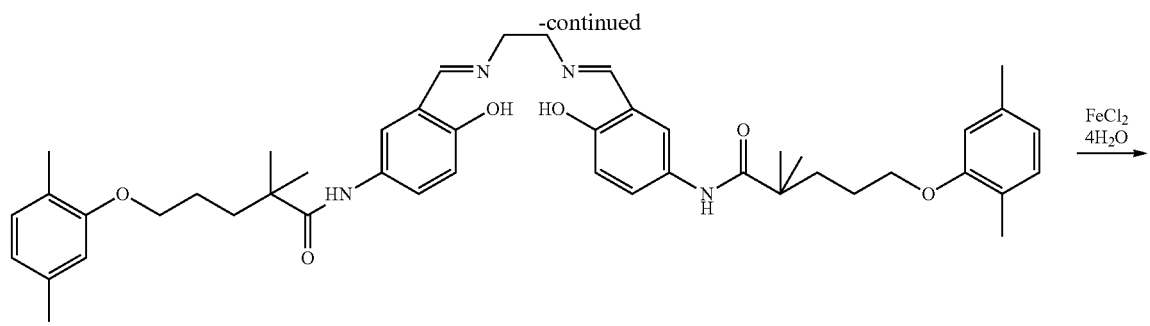
110-6
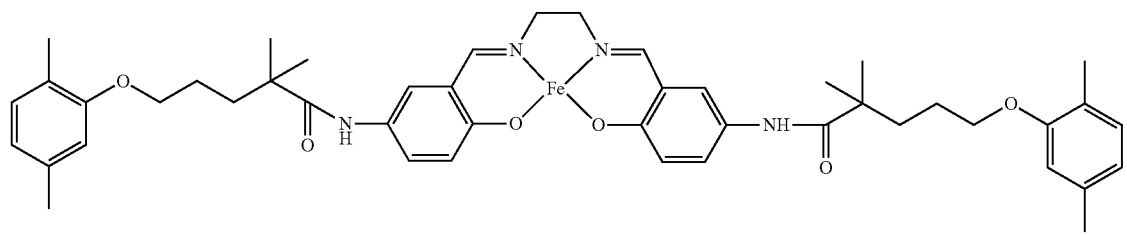
HHPH-114
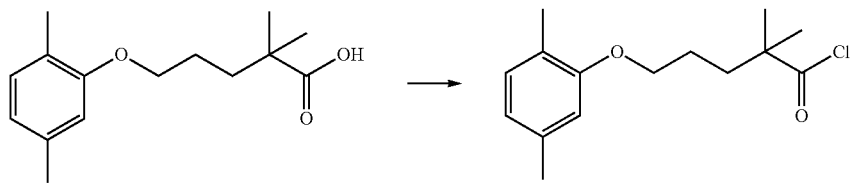
Gemfibrozil → 110-SM
Step 1 to Step 6 are the same as Example 8, and Step 8 below was subsequently performed.
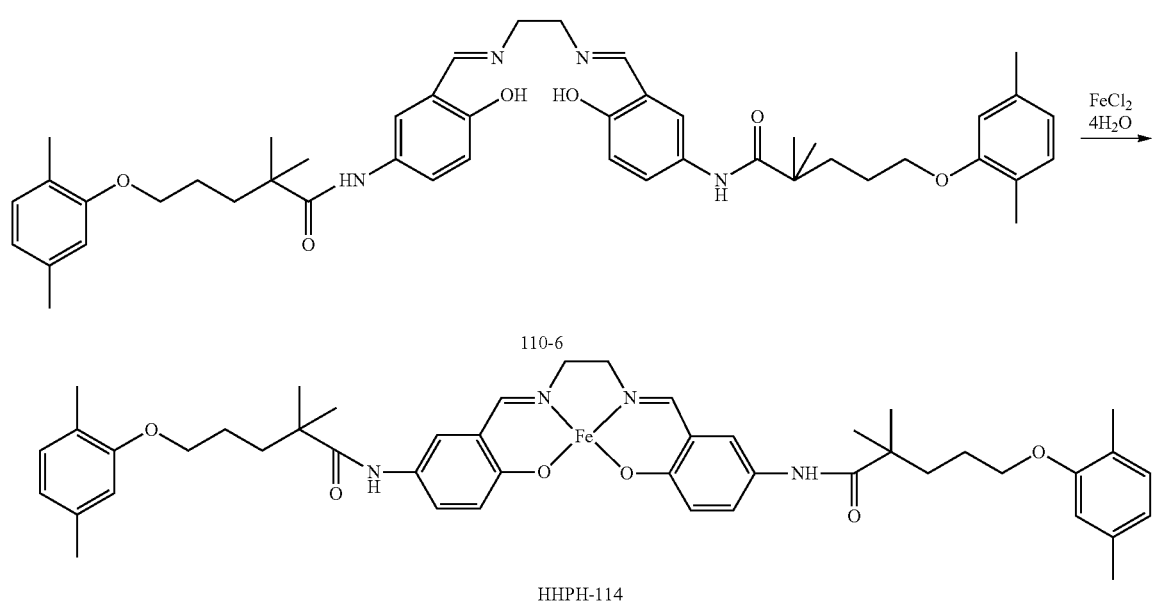
110-6
HHPH-114

Figure 20:
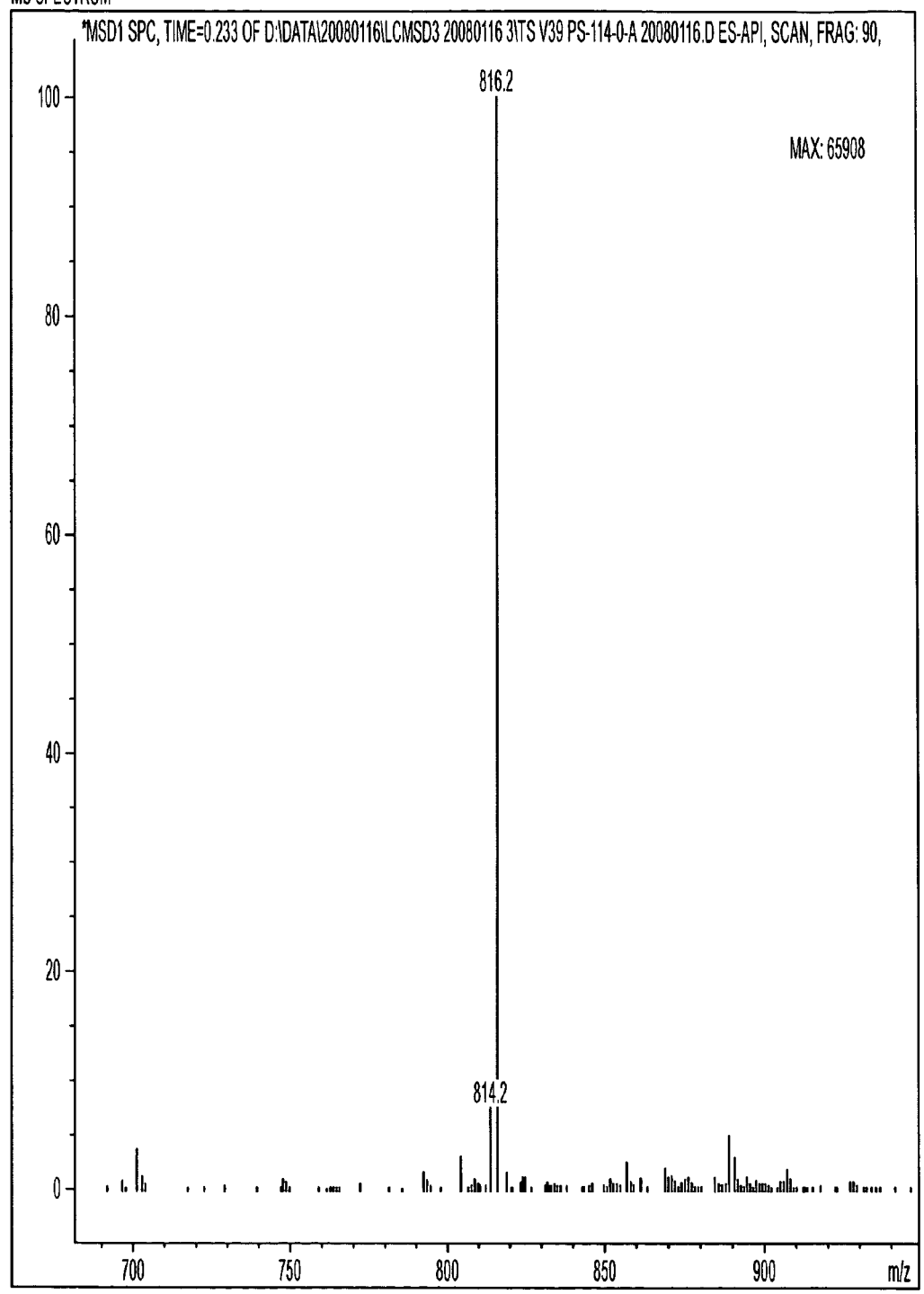
FIG. 20 is the mass spectrometry results of the foregoing compound.

$FeCl_2.4H_2O$ was added to the product (110-6). After the foregoing addition, the obtained mixture was further agitated for 30 minutes. The solvent was vaporized in a vacuum to obtain the product. The obtained product was recrystallized with methanol and diethyl ether, whereby 1 gram of a brown target compound was obtained. The target compound was confirmed as having a molecular weight of 816 with mass spectrometry (LC-MS). FIG. 20 shows the results thereof.

Example 10

Medicinal Effect of Compound in which Taxol was Bound with Fe-Salen

The compound in which Taxol was bound with the Fe-salen of Chemical Formula (1) was sprinkled on a culture medium in an amount that where such compound can be visually confirmed to be drawn to the superconducting magnet (compact solenoid magnet) of 4.7 tesla (T) manufactured by Niki Glass in a state where the rat L6 cells are confluent at 30%, and a photograph of the state of the culture medium after 48 hours was taken.

Shown is a state where the bar magnet was caused to come in contact with a square flask as the culture medium of the rat L6 cells. Subsequently, a photograph was taken from one end to the other end of the bottom face of the square flask after 48 hours, and the number of cells was calculated. At the proximal from the magnet, the compound obtained by binding Taxol with the Fe-salen is gravitated and increases the concentration of the compound, and it is evident that the number of cells is extremely lower than the distal based on the DNA inhibition effect. Consequently, the drug can be concentrated at the diseased site or tissues as the individual target based on the system of the present invention comprising the drug with magnetic properties and a magnetism generating means.

Example 11

Medicinal Effect of Compound in which a Lipid-Lowering Agent (Gemfibrozil) was Bound with Fe-Salen Gemfibrozil (Hyperlipoproteinemia Remedy, Blood Cholesterol Level-Lowering Agent which Lowers the Level of Triglyceride in the Blood)

The compound in which a lipid-lowering agent (Gemfibrozil) was bound with the Fe-salen of Chemical Formula (1) was sprinkled on a culture medium in an amount that where such compound can be visually confirmed to be drawn to the superconducting magnet (compact solenoid magnet) of 4.7 tesla (T) manufactured by Niki Glass in a state where the rat L6 cells are confluent at 30%, and a photograph of the state of the culture medium after 48 hours was taken.

Shown is a state where the bar magnet was caused to come in contact with a square flask as the culture medium of the rat L6 cells. Subsequently, a photograph was taken from one end to the other end of the bottom face of the square flask after 48 hours, and the number of cells was calculated. At the proximal from the magnet, the compound obtained by binding the lipid-lowering agent (Gemfibrozil) with the Fe-salen is gravitated and increases the concentration of the compound, and it is evident that the number of cells is extremely lower than the distal based on the DNA inhibition effect of the iron complex.

Consequently, the drug can be concentrated at the diseased site or tissues as the individual target based on the system of the present invention comprising the drug with magnetic properties and a magnetism generating means.

Example 12

Medicinal Effect of Compound in which a Lipid-Lowering Agent (Gemfibrozil) was Bound with Dimeric Fe-Salen Gemfibrozil (Hyperlipoproteinemia Remedy, Blood Cholesterol Level-Lowering Agent which Lowers the Level of Triglyceride in the Blood)

The compound in which a lipid-lowering agent (Gemfibrozil) was bound with the dimeric Fe-salen of Chemical Formula (1) was sprinkled on a culture medium in an amount that where such compound can be visually confirmed to be drawn to the superconducting magnet (compact solenoid magnet) of 4.7 tesla (T) manufactured by Niki Glass in a state where the rat L6 cells are confluent at 30%, and a photograph of the state of the culture medium after 48 hours was taken.

Shown is a state where the bar magnet was caused to come in contact with a square flask as the culture medium of the rat L6 cells. Subsequently, a photograph was taken from one end to the other end of the bottom face of the square flask after 48 hours, and the number of cells was calculated. At the proximal from the magnet, the compound obtained by binding the lipid-lowering agent (Gemfibrozil) with the dimeric Fe-salen is gravitated and increases the concentration of the compound, and it is evident that the number of cells is extremely lower than the distal based on the DNA inhibition effect of the iron complex. Consequently, the drug can be concentrated at the diseased site or tissues as the individual target based on the system of the present invention comprising the drug with magnetic properties and a magnetism generating means.

Example 13

Movement of electrons of the compound to be bound with the metal salen complex can be obtained based on the first-principle calculation.

A system for realizing this computer simulation comprises well-known hardware resources as a computer; that is, it comprises a memory, an arithmetic unit comprising an arithmetic circuit such as a CPU, and a display means for outputting the arithmetic results.

The memory comprises data for identifying the existing organic compound or three-dimensional structure, and a software program for realizing the computer simulation.

This software is able to add, change or delete the side chain of the respective compounds, bridge predetermined side chains, calculate the high area of the foregoing spin/charge density, and decide the spin/charge density as the overall structure. As this program, for example, a commercially available product (Dmol3 manufactured by Accelrys) can be used.

The user inputs the location of adding the side chain in the compound, or selects the side chain to be changed or deleted, and uses a support program of the memory and designates the location where a bridge is to be formed into the arithmetic unit. Upon receiving the input of these values, the arithmetic unit computes the spin/charge density and outputs the results to the display screen. Moreover, by the user adding the structure data of existing compounds to the computer system, the user can obtain the spin/charge density of known compounds.

The charge transfer of those in which a different compound was bound with the metal salen complex can be obtained by integrating the obtained upward and downward spin/charge density with a three-dimensional space. The letters e, b in Chemical Formula (I) and e, b, k, h, or e, h in Chemical Formula II show the calculation results of the charge transfer in each of the following tables. Minus shows the increase of electrons while plus shows the decrease of electrons.

TABLE 1

| Metal salen complex (Chemical Formula I) | Compounds to be bound | |
|---|---|---|
| Charge transfer | Compound name | Charge transfer |
| −031 | Ibuprofen Chemical Formula (1) | +0.31 |
| −0.31 | Mefenamic acid Chemical Formula (2) | +0.31 |
| −0.32 | Pefloxacin Chemical Formula (3) | +0.32 |
| −0.31 | Gemfibrozil Chemical Formula (4) | +0.31 |
| −0.32 | Rhodamine Chemical Formula (5) | +0.32 |
| −0.35 | Estrogen Chemical Formula (6) | +0.35 |
| −0.35 | Estrogen Chemical Formula (7) | +0.35 |
| −0.34 | Taxol Chemical Formula (8) | +0.34 |
| −0.28 | Glycine Chemical Formula (9) | +0.28 |
| −0.28 | Alanine Chemical Formula (10) | +0.28 |
| −0.27 | Arginine Chemical Formula (11) | +0.27 |
| −0.27 | Asparagine Chemical Formula (12) | +0.27 |
| −0.25 | Aspartic acid Chemical Formula (13) | +0.25 |
| −0.26 | Cysteine Chemical Formula (14) | +0.26 |
| −0.26 | Glutamic acid Chemical Formula (15) | +0.26 |
| −0.25 | Histidine Chemical Formula (16) | +0.25 |
| −0.27 | Isoleucine Chemical Formula (17) | +0.27 |
| −0.26 | Leucine Chemical Formula (18) | +0.26 |
| −0.24 | Lysine Chemical Formula (19) | +0.24 |
| −0.28 | Methionine Chemical Formula (20) | +0.28 |
| −0.29 | Phenyl Alanine Chemical Formula (21) | +0.29 |
| −0.26 | Proline Chemical Formula (22) | +0.26 |
| −0.26 | Serine Chemical Formula (23) | +0.26 |
| −0.25 | Threonine Chemical Formula (24) | +0.25 |
| −0.28 | Tryptophan Chemical Formula (25) | +0.28 |
| −0.29 | Tyrosine Chemical Formula (26) | +0.29 |
| −0.25 | Valine Chemical Formula (27) | +0.25 |

TABLE 2

| Metal salen complex (Chemical Formula I) | Compounds to be bound | |
|---|---|---|
| Charge transfer | Compound name | Charge transfer |
| −0.33 | Ifosfamide | +0.33 |
| −0.34 | Cyclophosphamide | +0.34 |
| −0.32 | Dacarbazine | +0.32 |
| −0.33 | Busulfan | +0.33 |
| −0.33 | Melphalan | +0.33 |
| −0.28 | Ranimustine | +0.28 |
| −0.30 | Estramustine sodium phosphate Chemical Formula | +0.30 |
| −0.31 | Nimustine hydrochloride | +0.31 |
| −0.39 | Docetaxel hydrate | +0.39 |
| −0.38 | Vincristine sulfate | +0.38 |
| −0.38 | Vinblastine sulfate | +0.38 |

TABLE 2-continued

| Metal salen complex (Chemical Formula I) | Compounds to be bound | |
|---|---|---|
| Charge transfer | Compound name | Charge transfer |
| −0.23 | Epirubicin hydrochloride | +0.23 |
| −0.33 | Vinorelbine ditartrate | +0.33 |
| −0.29 | Vindesine sulfate | +0.29 |
| −0.25 | Oxaliplatin | +0.25 |
| −0.22 | Carboplatin | +0.22 |
| −0.23 | Cisplatin | +0.23 |
| −0.24 | Nedaplatin | +0.24 |

TABLE 3

| Metal salen complex (Chemical Formula I) | Compounds to be bound | |
|---|---|---|
| Charge transfer | Compound name | Charge transfer |
| −0.19 | Anastorozole | +0.19 |
| −0.18 | Afema | +0.18 |
| −0.28 | Exemestane | +0.28 |
| −0.13 | Toremifene citrate | +0.13 |
| −0.23 | Bicalutamide | +0.23 |
| −0.39 | Flutamide | +0.39 |
| −0.22 | Mepitiostane | +0.22 |
| −0.30 | Estramustine sodium phosphate | +0.30 |
| −0.31 | Medroxyprogesterone acetate | +0.31 |
| −0.23 | Tamibarotene | +0.23 |
| −0.22 | Gefitinib | +0.22 |
| −0.24 | Tretinoin | +0.24 |
| −0.27 | Imatinib mesylate | +0.27 |
| −0.27 | Etoposide | +0.27 |
| −0.25 | Sobuzoxane | +0.25 |
| −0.22 | Irinotecan hydrochloride | +0.22 |
| −0.23 | Nogitecan hydrochloride | +0.23 |

TABLE 4

| Metal salen complex (Chemical Formula I) | Compounds to be bound | |
|---|---|---|
| Charge transfer | Compound name | Charge transfer |
| −0.33 | Ubenimex | +0.33 |
| −0.31 | Sizofiran | +0.31 |
| −0.28 | Lentinan | +0.28 |
| −0.33 | Ifosfamide | +0.33 |
| −0.34 | Cyclophosphamide | +0.34 |
| −0.32 | Dacarbazine | +0.32 |
| −0.33 | Busulfan | +0.33 |
| −0.33 | Melphalan | +0.33 |
| −0.28 | Ranimustine | +0.28 |
| −0.30 | Estramustine sodium phosphate | +0.30 |
| −0.31 | Nimustine hydrochloride | +0.31 |

TABLE 5

Metal salen complex (Chemical Formula I) — Compounds to be bound

| Charge transfer | Compound name | Charge transfer |
|---|---|---|
| −0.23 | Enocitabin Chemical Formula (3) | +0.23 |
| −0.24 | Capecitabine Chemical Formula (4) | +0.24 |
| −0.22 | Camofur Chemical Formula (5) | +0.22 |
| −0.23 | Gimeracil Chemical Formula (6) | +0.23 |
| −0.33 | Oteracil potassium Chemical Formula (7) | +0.33 |
| −0.28 | Cytarabine Chemical Formula (8) | +0.28 |
| −0.30 | Cytarabine Ocphosphate Chemical Formula (9) | +0.30 |
| −0.31 | Tegafur Chemical Formula (10) | +0.31 |
| −0.30 | Doxifluridine Chemical Formula (11) | +0.30 |
| −0.32 | Hydroxycarbamide Chemical Formula (12) | +0.32 |
| −0.33 | Fluorouracil Chemical Formula (13) | +0.33 |
| −0.35 | Mercaptopurine hydrate Chemical Formula (14) | +0.35 |
| −0.33 | Fludarabine phosphate Chemical Formula (15) | +0.33 |
| −0.34 | Gemcitabine hydrochloride Chemical Formula (16) | +0.34 |
| −0.33 | Actinomycin D | +0.33 |
| −0.24 | Aclarubicin hydrochloride | +0.24 |
| −0.32 | Idarubicin hydrochloride | +0.32 |
| −0.23 | Epirubicin hydrochloride | +0.23 |
| −0.33 | Zinostatin stimalamer | +0.33 |
| −0.29 | Daunorubicin hydrochloride | +0.29 |
| −0.30 | Doxorubicin hydrochloride | +0.30 |
| −0.31 | Bleomycin hydrochloride | +0.31 |
| −0.19 | Peplomycin hydrochloride | +0.19 |
| −0.30 | Mitomycin C | +0.30 |
| −0.32 | Amrubicin hydrochloride | +0.32 |
| −0.33 | Pirarubicine hydrochloride | +0.33 |

TABLE 6

Metal salen complex (Chemical Formula II) — Compounds to be bound

| Charge transfer | Compound name | Charge transfer |
|---|---|---|
| −0.23 | Enocitabin | +0.23 |
| −0.24 | Capecitabine | +0.24 |
| −0.22 | Camofur | +0.22 |
| −0.23 | Gimeracil | +0.23 |
| −0.33 | Oteracil potassium | +0.33 |
| −0.28 | Cytarabine | +0.28 |
| −0.30 | Cytarabine Ocphosphate | +0.30 |
| −0.31 | Tegafur | +0.31 |
| −0.30 | Doxifluridine | +0.30 |
| −0.32 | Hydroxycarbamide | +0.32 |
| −0.33 | Fluorouracil | +0.33 |
| −0.35 | Mercaptopurine hydrate | +0.35 |
| −0.33 | Fludarabine phosphate | +0.33 |
| −0.34 | Gemcitabine hydrochloride | +0.34 |
| −0.33 | Actinomycin D | +0.33 |
| −0.24 | Aclarubicin hydrochloride | +0.24 |
| −0.32 | Idarubicin hydrochloride | +0.32 |
| −0.23 | Epirubicin hydrochloride | +0.23 |
| −0.33 | Zinostatin stimalamer | +0.33 |
| −0.29 | Daunorubicin hydrochloride | +0.29 |
| −0.30 | Doxorubicin hydrochloride | +0.30 |
| −0.31 | Bleomycin hydrochloride | +0.31 |
| −0.19 | Peplomycin hydrochloride | +0.19 |
| −0.30 | Mitomycin C | +0.30 |
| −0.32 | Amrubicin hydrochloride | +0.32 |
| −0.33 | Pirarubicine hydrochloride | +0.33 |

TABLE 7

Metal salen complex (Chemical Formula II) — Compounds to be bound

| Charge transfer | Compound name | Charge transfer |
|---|---|---|
| −0.39 | Docetaxel hydrate | +0.39 |
| −0.38 | Vincristine sulfate | +0.38 |
| −0.38 | Vinblastine sulfate | +0.38 |
| −0.23 | Epirubicin hydrochloride | +0.23 |
| −0.33 | Vinorelbine ditartrate | +0.33 |
| −0.29 | Vindesine sulfate | +0.29 |
| −0.25 | Oxaliplatin | +0.25 |
| −022 | Carboplatin | +0.22 |
| −0.23 | Cisplatin | +0.23 |
| −0.24 | Nedaplatin | +0.24 |
| −0.19 | Anastorozole | +0.19 |
| −0.18 | Afema | +0.18 |
| −0.28 | Exemestane | +0.28 |
| −0.13 | Toremifene citrate | +0.13 |
| −0.23 | Bicalutamide | +0.23 |
| −0.39 | Flutamide | +0.39 |
| −0.22 | Mepitiostane | +0.22 |
| −0.30 | Estramustine sodium phosphate | +0.30 |
| −0.31 | Medroxyprogesterone acetate | +0.31 |

TABLE 8

Metal salen complex (Chemical Formula II) — Compounds to be bound

| Charge transfer | Compound name | Charge transfer |
|---|---|---|
| −0.23 | Tamibarotene | +0.23 |
| −0.22 | Gefitinib | +0.22 |
| −0.24 | Tretinoin | +0.24 |
| −0.27 | Imatinib mesylate | +0.27 |
| −0.27 | Etoposide | +0.27 |
| −0.25 | Sobuzoxane | +0.25 |
| −0.22 | Irinotecan hydrochloride | +0.22 |
| −0.23 | Nogitecan hydrochloride | +0.23 |
| −0.33 | Ubenimex | +0.33 |
| −0.31 | Sizofiran | +0.31 |
| −0.28 | Lentinan | +0.28 |

TABLE 9

Metal salen complex (Chemical Formula I) — Compounds to be bound

| Charge transfer | Compound name | Charge transfer |
|---|---|---|
| −0.22 | Lidocaine | +0.22 |
| −0.25 | Ethyl aminobenzoate | +0.25 |
| −0.25 | Oxybuprocaine hydrochloride | +0.25 |
| −0.24 | Oxethazaine | +0.24 |
| −0.23 | Dibucaine | +0.23 |
| −0.28 | Ethyl p-Piperidinoacetylaminobenzoate | +0.28 |
| −0.25 | Procaine | +0.25 |
| −0.23 | Mepivacaine | +0.23 |
| −0.24 | Diethylaminoethyl p-Butylaminobenzoate hydrochloride | +0.24 |
| −0.26 | Bupivacaine hydrochloride | +0.26 |
| −0.24 | Ropivacaine hydrochloride hydrate | +0.24 |
| −0.12 | Lidocaine | +0.12 |
| −0.15 | Ethyl aminobenzoate | +0.15 |
| −0.15 | Oxybuprocaine hydrochloride | +0.15 |

TABLE 9-continued

| Metal salen complex (Chemical Formula I) | Compounds to be bound | |
|---|---|---|
| Charge transfer | Compound name | Charge transfer |
| −0.14 | Oxethazaine | +0.14 |
| −0.13 | Dibucaine | +0.13 |
| −0.18 | Ethyl p-Piperidinoacetylaminobenzoate | +0.18 |
| −0.15 | Procaine | +0.15 |
| −0.13 | Mepivacaine | +0.13 |
| −0.14 | Diethylaminoethyl p-Butylaminobenzoate hydrochloride | +0.14 |
| −0.16 | Bupivacaine hydrochloride | +0.16 |
| −0.14 | Ropivacaine hydrochloride hydrate | +0.14 |

TABLE 10

| Metal salen complex (Chemical Formula I) | Compounds to be bound | |
|---|---|---|
| Charge transfer | Compound name | Charge transfer |
| −0.32 | Leuprorelin Chemical Formula (3) | +0.32 |
| −0.35 | Methotrexate Chemical Formula (4) | +0.35 |
| −0.35 | Novantrone Chemical Formula (5) | +0.35 |
| −0.34 | Photofrin Chemical Formula (6) | +0.34 |
| −0.33 | Photofrin Chemical Formula (7) | +0.33 |
| −0.28 | Mylotarg Chemical Formula (8) | +0.28 |

What is claimed is:

1. An auto magnetism-imparting metal salen complex molecule represented by formula (IV):

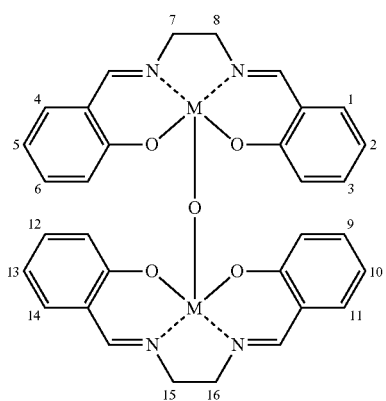

(IV)

wherein M is selected from Fe, Cr, Mn, Co, Ni, Mo, Ru, Rh, Pd, W, Re, Os, Ir, Pt, Nd, Sm, Eu and Gd, and wherein medicinal molecules are bonded via an amide group to locations 5 and 10 or locations 2 and 13, and the medicinal molecules are independently selected from:

paclitaxel, gemfibrozil,

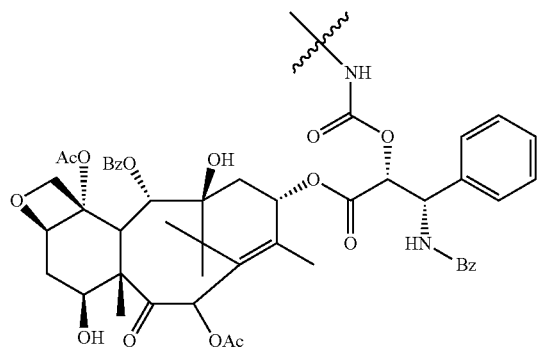

wherein Ac is an acetyl group and Bz is a benzoyl group,

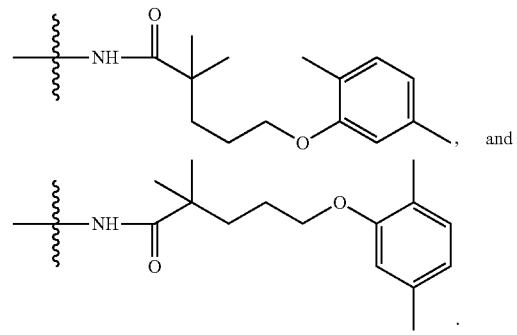

and

2. The auto magnetism-imparting metal salen complex molecule according to claim 1, wherein at least one of the medicinal molecules is paclitaxel.

3. The auto magnetism-imparting metal salen complex molecule according to claim 1, wherein at least one of the medicinal molecules is gemfibrozil.

4. An auto magnetism-imparting metal salen complex molecule represented by
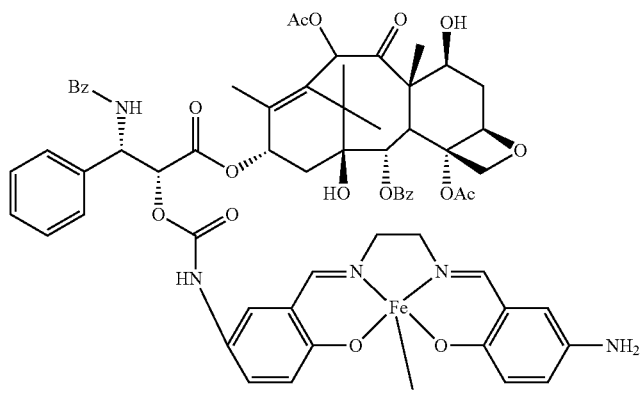
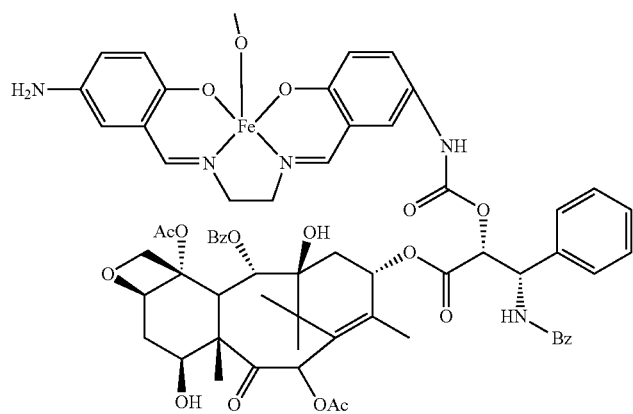
wherein Ac is an acetyl group and Bz is a benzoyl group.
5. An auto magnetism-imparting metal salen complex molecule represented by
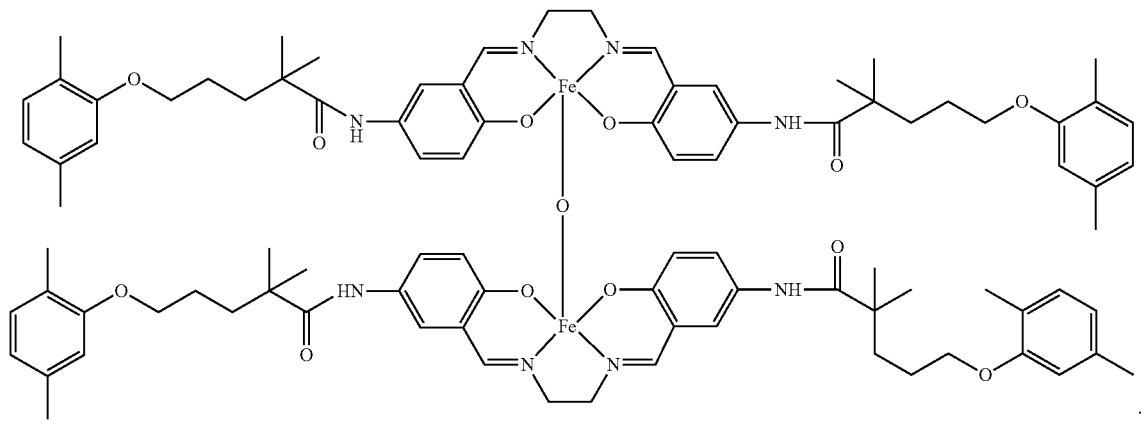
* * * * *